US011905560B2

(12) United States Patent
Chao-Shern

(10) Patent No.: US 11,905,560 B2
(45) Date of Patent: Feb. 20, 2024

(54) METHODS FOR MULTIPLEX DETECTION OF ALLELES ASSOCIATED WITH CORNEAL DYSTROPHY

(71) Applicant: Avellino Lab USA, Inc., Menlo Park, CA (US)

(72) Inventor: Connie Chao-Shern, Menlo Park, CA (US)

(73) Assignee: Avellino Lab USA, Inc.

( * ) Notice: Subject to any disclaimer, the term of this patent is extended or adjusted under 35 U.S.C. 154(b) by 227 days.

(21) Appl. No.: 16/604,310

(22) PCT Filed: Apr. 10, 2018

(86) PCT No.: PCT/US2018/026962
§ 371 (c)(1),
(2) Date: Oct. 10, 2019

(87) PCT Pub. No.: WO2018/191304
PCT Pub. Date: Oct. 18, 2018

(65) Prior Publication Data
US 2020/0040397 A1  Feb. 6, 2020

Related U.S. Application Data

(60) Provisional application No. 62/624,660, filed on Jan. 31, 2018, provisional application No. 62/624,661, (Continued)

(51) Int. Cl.
*C12Q 1/6883* (2018.01)
*C12Q 1/6827* (2018.01)
*G01N 33/58* (2006.01)

(52) U.S. Cl.
CPC ......... *C12Q 1/6883* (2013.01); *C12Q 1/6827* (2013.01); *G01N 33/582* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| 5,962,332 A | 10/1999 | Singer et al. |
| 11,525,160 B2 | 12/2022 | Chao-Shern et al. |

(Continued)

FOREIGN PATENT DOCUMENTS

| CN | 105899681 A | 8/2016 |
| JP | 2009523442 A | 6/2009 |

(Continued)

OTHER PUBLICATIONS

Lakshminarayanan, R. et al. The Ocular Surface 12(4):234 (Oct. 2014). (Year: 2014).*

(Continued)

*Primary Examiner* — Diana B Johannsen
(74) *Attorney, Agent, or Firm* — Morgan, Lewis & Bockius LLP

(57) ABSTRACT

The present disclosure provides a method for detecting corneal dystrophy in a subject, comprising a reaction mixture, the reaction mixture comprising one or more labeled probes comprising a mutant TGFBI nucleotide sequence; the reaction mixture further comprises at least one amplification primer pair for amplifying a TGFBI gene sequence from a biological sample from the subject; and detecting one, two, three, four, five or six mutations selected from the group consisting of G623D, M502V, R124S, A546D, H572R, and H626R mutations in TGFBI gene, wherein the detecting comprises detecting the one or more mutations using the labeled detection probes. Further provided is a reaction kit comprising the reaction mixture.

4 Claims, 12 Drawing Sheets
Specification includes a Sequence Listing.

Related U.S. Application Data filed on Jan. 31, 2018, provisional application No. 62/573,537, filed on Oct. 17, 2017, provisional application No. 62/483,588, filed on Apr. 10, 2017.

(56) References Cited

U.S. PATENT DOCUMENTS

| | | |
|---|---|---|
| 2009/0305394 A1 | 12/2009 | Lee et al. |
| 2012/0208196 A1 | 8/2012 | Hirai et al. |
| 2013/0302811 A1 | 11/2013 | Lee et al. |
| 2014/0243222 A1 | 8/2014 | Lee et al. |

FOREIGN PATENT DOCUMENTS

| | | |
|---|---|---|
| JP | 2012067097 A | 4/2012 |
| JP | 2013502215 A | 1/2013 |
| JP | 2013542723 A | 11/2013 |
| KR | 20110116832 A | 10/2011 |
| KR | 20120022219 A | 3/2012 |

OTHER PUBLICATIONS

Yoo, S. et al. Proceedings of the 2007 Frontiers in the Convergency of Bioscience and Information Technologies, pp. 69-74 (Oct. 2007). (Year: 2007).*

Niel-Butschi, F. et al. Molecular Vision 17:1192 (May 2011). (Year: 2011).*

Evans et al., "Genotype-Phenotype Correlation for TGFBI Corneal Dystrophies Identifies p.(G623D) as a Novel Cause of Epithelial Basement Membrane Dystrophy," Investigative Ophthalmology & Visual Science, 57: 5407-5414 (2016).

Zeng et al., "TGFBI Gene Mutation Analysis of Clinically Diagnosed Granular Corneal Dystrophy Patients Prior to PTK: A Pilot Study from Eastern China," Scientific Reports, 7: 596 (2017).

International Search Report issued in corresponding International Patent Application No. PCT/US2018/026962 dated Jul. 11, 2018.

Written Opinion issued in corresponding International Patent Application No. PCT/US2018/026962 dated Jul. 11, 2018.

Avellino Lab USA, Inc., EP18784486, Supplementary European Search Report, dated Apr. 20, 2021, 11 pgs.

Avellino Lab USA, Inc., JP2019555594, Decision to Grant a Patent, dated Jun. 6, 2023, 8 pgs.

Avellino Lab USA, Inc., JP2019555594, Notice of Reasons for Refusal, dated Apr. 18, 2023, 4 pgs.

Avellino Lab USA, Inc., CN201880033645.1, Notice of Reasons for Refusal, dated Nov. 1, 2022, 7 pgs.

Ariela Gordon-Shaag et al., "The Genetic and Environmental Factors for Keratoconus", Human Genetic Diseases, BioMed Research International, vol. 2015, Article ID 795738, Received Oct. 9, 2014; Revised Jan. 8, 2015; Accepted Jan. 9, 2015, 20 pages.

* cited by examiner

← England: G6234D; R124S; H40..

name
England: G6234D; R124S; H403Q; R124C; R124H; GCD;

description
Ethnicity: English; Iranian (H403Q); Bangladeshi (R124C)
G623D: 5
R124S: 6
H403Q: 1 (Keratoconus)
R124C: 3
R124H: 6
GCD: 1

Figure 3.

| Mutations | Reported Case Numbers |
|---|---|
| Five most common mutations in the current genetic test panel | |
| R124C<br>Lattice Corneal Dystrophy type 1 | 372 |
| R555W<br>Granular Corneal Dystrophy type 1 | 338 |
| R124H<br>Granular Corneal Dystrophy type 2 | 325 |
| R124L<br>Reis-Buckler corneal dystrophy | 110 |
| R555Q<br>Thiel-Behnke corneal dystrophy | 75 |
| Six additional mutations in the expended test panel | |
| H626R<br>Lattice Corneal Dystrophy subtype I/IIIA | 117 |
| A546D<br>Variant Lattice Corneal Dystrophy | 48 |
| H572R<br>Lattice Corneal Dystrophy subtype 1 | 34 |
| G623D<br>Variant Reis-Buckler Corneal Dystrophy | 26 |
| R124S<br>Subtype Granular Corneal Dystrophy type 1 | 18 |
| M502V<br>Variant Corneal Dystrophy and Variant Thiel-Behnke Corneal Dystrophy | 4 |

Figure 4.

| UCL/Moorfields % detection of 91 UK ethnically diverse cohort with 68 TGFBI CDs | | | | | | |
|---|---|---|---|---|---|---|
| Clinical Diagnosis | Case # | Case % | TGFBI Mutation | Mutation # | Mutation % | Comments |
| Lattice Corneal Dystrophy | 24 | 35% | R124C | 19 | 28% | |
| | | | V625D | 1 | 1% | Asian |
| | | | H626R* | 2 | 3% | |
| | | | A620D | 1 | 1% | Asian |
| | | | G623D* | 1 | 1% | |
| Granular Corneal Dystrophy 1 | 21 | 31% | R555W | 13 | 19% | |
| Granular Corneal Dystrophy 2 | | | R124H | 8 | 12% | |
| TB/RB CD | 23 | 34$ | R555Q | 20 | 29% | |
| | | | R124L | 1 | 1% | |
| | | | G623D* | 2 | 3% | |
| Total TGFBI CD | 68 | | Universal Test | 61 | 90% | |
| | | | Additional 6 SNPs* | 5 | 7% | |
| | | | Total 11 SNPs | 66 | 97% | |

Figure 5A.

| Codon number | Position | dbSNP (19 total) | LT Assay ID | Target sequence |
|---|---|---|---|---|
| R124S | 135382095 | rs1219909210 | ANMFXKJ | ACGAGACCCTGGAGTCGTTGGATCCACCACCACTCAGCTGTACAC GGAC(C/A)GCACGGAGAAGTGAGGCCTGAGATGGAGGGCCC GGCAGCTTCACCATC SEQ ID NO: 1 |
| A546D | 135392443 | rs267607109 | ANNKR6G | GACCCTCAAC CGGG AAG GAGTCTACACAGTC TTT GCT CCC ACAAATGAAG(C/A)CTTCCGAGCCTGCCACCAAGAGAACGGAG CAG ACT CTT GGGTAAAGACC SEQ ID NO: 2 |
| H572R | 135394815 | no | ANPRKRE | CTTGCCAACATCCTGAAATACC CCAAGGAACTTGCCAACATCCTGAAATACC(A/G)CATTGGTGATG AAATCCTGGTTAGCGGAGGCAT CGG GGC CCTGGTGCGGCTA SEQ ID NO: 3 |
| G623D | 135396587 | rs1219909215 | ANRWFCC | GAGTGTCAACAAGGAGCTGTTGCCGAGCTGACATCATGGCCA CAAATG(G/A)CGTGGTCCATGTCATCACCAATGTTCTGCA GCC TCC AGG TAAGTGTCGCA SEQ ID NO: 4 |
| H626R | 135396595 | no | ANTZ9V9 | (AAGGAGCCTGTTGCCGAGC) CTGACATCATGGCCACAAATGGCGTGGTCC(A/G)TGTCATCACCA ATGTTCTGCAGCCTCC AGG TAA GTG TCGCATCCCCACTGA SEQ ID NO: 5 |
| M502V | 135391462 | rs188677757 | ANRWFF6 | CACGACAAGAGGGGGAGGTACGGAGACCCTGTTCACGATGGACC GGGTGCTGACCCCCCA(A/G)TGGGGACTGTCATGGATGTCCTGA AGGGAGACA ATC GCT T TAGGTAATTA GTTCCATCCC SEQ ID NO: 6 |

Figure 5B. Version 1 (V1)

| Codon number | Primer Fwd | Primer Rev | VIC Probe (Norm) | FAM Probe (Mut) | ABY Probe (Norm) - NN complement | JUN Probe (Mut) HH compliment |
|---|---|---|---|---|---|---|
| R124S | CCACCACCACTCAGCTGTAC SEQ ID NO: 7 (Ver.1 Working with V1 VIC/FAM probes) | TCCATCTCAGGCCTCAGCT SEQ ID NO: 13 (Ver.1 Working with V1 VIC/FAM probes) | CTCCGTGCGGTCCGT SEQ ID NO: 19 (Ver.1 Working with V1 primers) | TCTCCGTGCTGTCCGT SEQ ID NO: 25 (Ver.1 Working with V1 primers) | | |
| A546D | TCT ACA CAG TCT TTG CTC CCA CA SEQ ID NO: 8 (Ver.1 Working with V1 VIC/FAM probes) | CTC CGT TCT CTT GGT GGC A SEQ ID NO: 14 (Ver.1 Working with V1 VIC/FAM probes) | CTC GGA AGG CTT CAT T SEQ ID NO: 20 (Ver.1 Working with V1 primers) | CTC GGA AGT CTT CAT T SEQ ID NO: 26 Ver.1 (Working with V1 primers) | CTT GGT GGC AGG GCT CGG AAG GCT TCA TTT GT SEQ ID NO: 31 (Ver.1 Not Working ) | CTT GGT GGC AGG GCT CGG AAG TCT TCA TTT GT SEQ ID NO: 34 (Ver.1 Not Working with any primers) |
| H572R | CCA AGG AAC TTG CCA ACA T SEQ ID NO: 9 (Ver.1 Working with V1 VIC/FAM probes) | CCT CCG CTA ACC AGG ATT TCA TC SEQ ID NO: 15 (Ver.1 Working with V1 VIC/FAM probes) | CCT GAA ATA CCA CAT TGG SEQ ID NO: 21 (Ver.1 Working with V1 primers) | CCT GAA ATA CCG CAT TGG SEQ ID NO: 27 (Ver.1 Working with V1 primers) | C TTG CCA ACA TCC TGA AAT ACC ACA TTG GTG AT SEQ ID NO: 32 (Ver.1 Not Working with any primers) | C TTG CCA ACA TCC TGA AAT ACC GCA TTG GTG AT SEQ ID NO: 35 (Ver.1 Not Working with any primers) |
| G623D | TTG CCG AGC CTG ACA TCA SEQ ID NO: 10 (Ver.1 Working with V1 VIC/FAM probes and ABY/JUN probes) | TGC AGA ACA TTG GTG ATG ACA TG SEQ ID NO: 16 (Ver.1 Working with V1 VIC/FAM probes and ABY/JUN probes) | CACAAATGGCGTGGT C SEQ ID NO: 22 (Ver.1 Working with V1 primers) | CCACAAATGACGTGGT C SEQ ID NO: 28 (Ver.1 Working with V1 primers) | CA TCA TGG CCA CAA ATG GCG TGG TCC ATG TC SEQ ID NO: 33 (Ver.1 Working with V1 primers) | CA TCA TGG CCA CAA ATG ACG TGG TCC ATG TC SEQ ID NO: 36 (Ver.1 Working with V1 primers) |

Figure 5B continued

| Codon number | Primer Fwd | Primer Rev | VIC Probe (Norm) | FAM Probe (Mut) | ABY Probe (Norm) - NN complement | JUN Probe (Mut) HH compliment |
|---|---|---|---|---|---|---|
| H626R | CTGACATCATGGCCACAAATGG SEQ ID NO: 11 (Ver.1 Working only with V1 VIC/FAM probes) | GGAGGCTGCAGAACATTGGT SEQ ID NO: 17 (Ver.1 Working only with V1 VIC/FAM probes) | CGTGGTCCATGTCATC SEQ ID NO: 23 (Ver.1 Working only with V1 primers) | TGGTCCGTGTCATC SEQ ID NO: 29 (Ver.1 Working only with V1 primers) | | |
| M502V | GGACCGG GTG CTG ACC SEQ ID NO: 12 (Ver.1 Working only with V1 VIC/FAM probes) | CTCCCTTCAGGACATCCA SEQ ID NO: 18 (Ver.1 Working only with V1 VIC/FAM probes) | TGACAGTCCCCATTGGG SEQ ID NO: 24 (Ver.1 Working only with V1 primers) – used in multiplexing experiments with G623D | TGACAGTCCCCACTGGG SEQ ID NO: 30 (Ver. 1 Working only with V1 primers) - used in multiplexing experiments with G623D | | |

Figure 5C. Version 2 (V2)

| Codon number | Primer Fwd | Primer Rev | VIC Probe (Norm) | FAM Probe (Mut) | ABY Probe (Norm) - NN complement | JUN Probe (Mut) HH compliment |
|---|---|---|---|---|---|---|
| R124S | GACCCTGGAGTCGTTGGATC SEQ ID NO: 37 (Ver. 2 Not Working with V2 VIC/FAM probes) | CCCGGCAGCTTCACCATC SEQ ID NO: 43 (Ver. 2 Not Working with V2 VIC/FAM probes) | CGACTTCTCCGTGCGGT CCGT GTACAG SEQ ID NO: 49 (Ver. 2 Not Working) | CGACTTCGACTT TCTCCGTGCTGTC CGT GTACAG GTACAG SEQ ID NO: 53 (Ver. 2 Not Working) | | |
| A546D | CGGGAAGGAGTCTACACAG TCTTT SEQ ID NO: 38 (Ver. 2 Not Working with V1 or V2 ABY/JUN probes) | AAGAGTCTGCTCCGTTCTCT T SEQ ID NO: 44 (Ver. 2 Not Working with V1 or V2 ABY/JUN probes) | | | AGGGCTCGGAAGGCTTC ATT SEQ ID NO: 56 (Ver. 2 Not Working with V1 Primers) | AGGGCTCGGAAGTCTTC ATT SEQ ID NO: 59 (Ver. 2 Not Working with V1 primers) |
| H572R | TGAAATACCCCAAGGAACT TG SEQ ID NO: 39 (Ver. 2 Not Working with V1 probes) | GCCCCGATGCCTCCGCTAAC CAGG SEQ ID NO: 45 (Ver. 2 Not Working with V1 probes) | | | ACATCCTGAAATACCACA TTGG SEQ ID NO: 57 (Ver. 2 Working with V2 primers) | ACATCCTGAAATACCGCA TTGG SEQ ID NO: 60 (Ver. 2 Working with V2 primers) |
| G623D | AGGAGCCTGTTGCCGAGC SEQ ID NO: 40 (Ver. 2 Not Working with V1 or V2 probes) | CCTGGAGGCTGCAGAACAT TGGTG SEQ ID NO: 46 (Ver. 2 Not Working with V1 or V2 probes) | | | CACAAATG GCGTGGTC SEQ ID NO: 58 (Ver. 2 Not Working with V1 or V2 primers) | CACAAATGACGTGGTC SEQ ID NO: 61 (Ver. 2 Not Working with V1 or V2 primers) |

Figure 5C continued

| Codon number | Primer Fwd | Primer Rev | VIC Probe (Norm) | FAM Probe (Mut) | ABY Probe (Norm) - NN compliment | JUN Probe (Mut) HH compliment |
|---|---|---|---|---|---|---|
| H626R | TTGCCGAGCCTGACATCATGGC SEQ ID NO: 41 (Ver. 2 Working with V2 probes) | CACTTACCTGGAGGCGCAGA SEQ ID NO: 47 (Ver. 2 Working with V2 probes) | TGGCGTGGTCCATGTC SEQ ID NO: 50 (Ver. 2 Working with V2 primers) | TGGCGTGGTCCGTGTC SEQ ID NO: 54 (Ver. 2 Working with V2 primers) | | |
| M502V | GTTCACGATGGACCGG SEQ ID NO: 42 (Ver. 2 Not Working with V2 probes) | AGCGATTGTCTCCCTTCA SEQ ID NO: 48 (Ver. 2 Not Working with V2 probes) | TCCCCATTGGGGGGGT SEQ ID NO: 52 (Ver. 2 Not Working with V2 primers) | TCCCCACTGGGGGGGT SEQ ID NO: 55 (Ver. 2 Not Working with V2 primers) | | |

Figure 6A. G623D discrimination plot from the multiplexing experiment from Example 4.
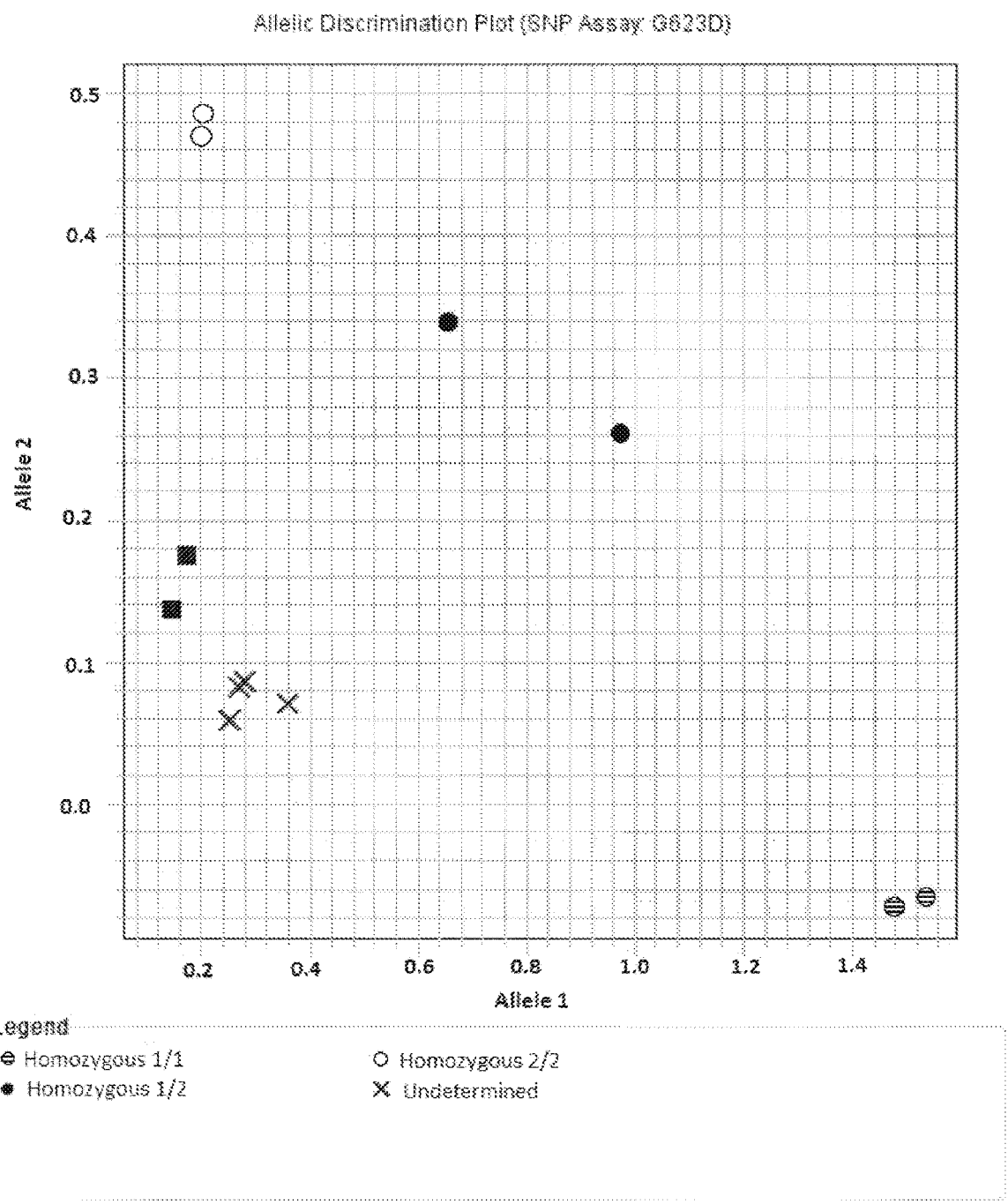

Figure 6B. M502V discrimination plot from the multiplexing experiment from Example 4.
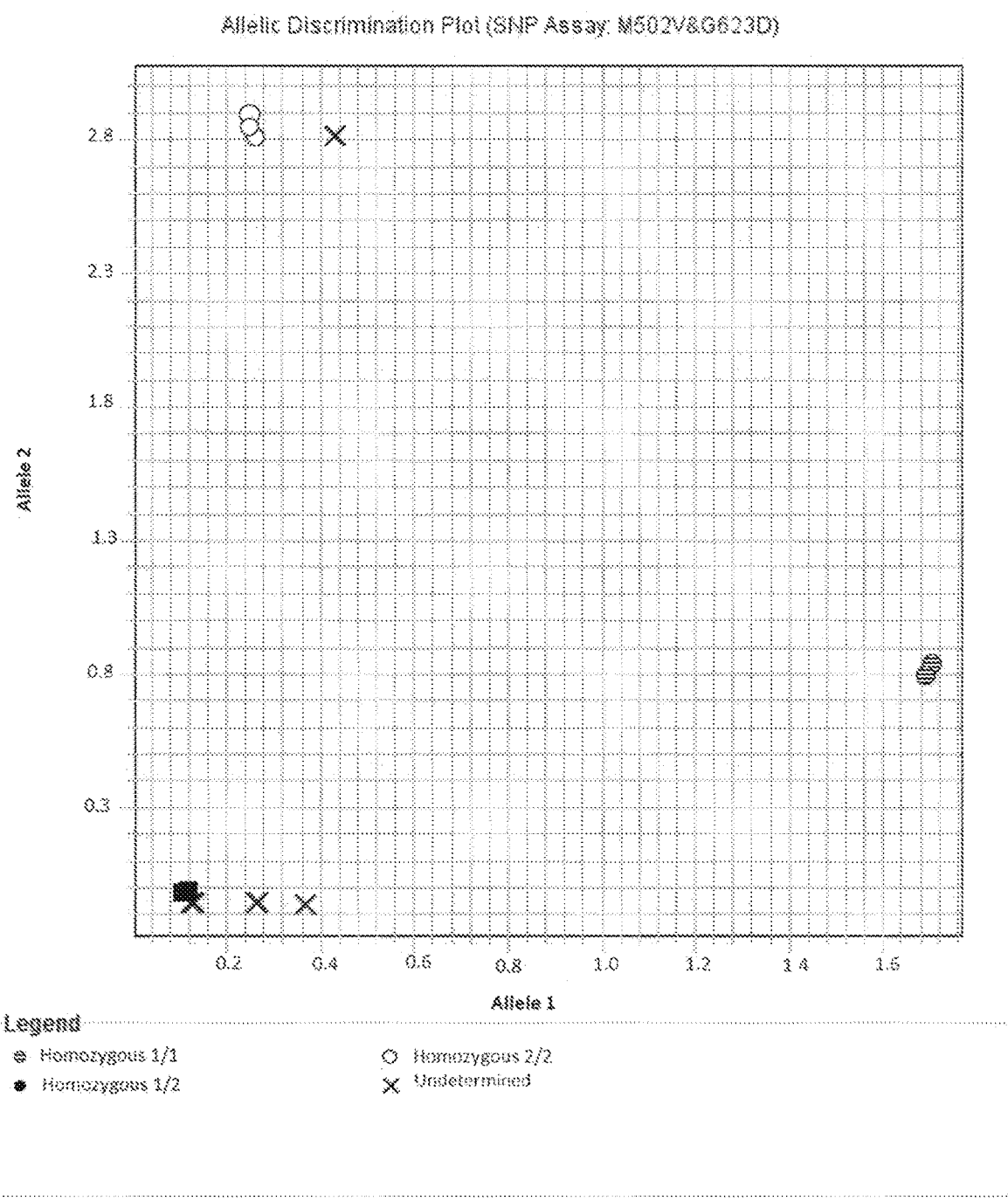

SEQUENCE LISTING

<160> NUMBER OF SEQ ID NOS: 62

<210> SEQ ID NO 1
<211> LENGTH: 100
<212> TYPE: DNA
<213> ORGANISM: Artificial Sequence
<220> FEATURE:
<223> OTHER INFORMATION: R124S Target sequence
<220> FEATURE:
<221> NAME/KEY: misc_feature
<222> LOCATION: (50)..(50)
<223> OTHER INFORMATION: n is c or a

<400> SEQUENCE: 1
acgagaccct ggagtcgttg gatccaccac cactcagctg tacacggacn gcacggagaa     60
gctgaggcct gagatggagg ggcccggcag cttcaccatc                          100

<210> SEQ ID NO 2
<211> LENGTH: 101
<212> TYPE: DNA
<213> ORGANISM: Artificial Sequence
<220> FEATURE:
<223> OTHER INFORMATION: A546D Target sequence
<220> FEATURE:
<221> NAME/KEY: misc_feature
<222> LOCATION: (51)..(51)
<223> OTHER INFORMATION: n is c or a

<400> SEQUENCE: 2
gaccctcaac cgggaaggag tctacacagt ctttgctccc acaaatgaag ncttccgagc     60
cctgccacca agagaacgga gcagactctt gggtaaagac c                        101

<210> SEQ ID NO 3
<211> LENGTH: 105
<212> TYPE: DNA
<213> ORGANISM: Artificial Sequence
<220> FEATURE:
<223> OTHER INFORMATION: H572R Target sequence
<220> FEATURE:
<221> NAME/KEY: misc_feature
<222> LOCATION: (53)..(53)
<223> OTHER INFORMATION: n is a or g

<400> SEQUENCE: 3
cttgccaaca tcctgaaata ccccaaggaa cttgccaaca tcctgaaata ccncattggt     60
gatgaaatcc tggttagcgg aggcatcggg gccctggtgc ggcta                    105

<210> SEQ ID NO 4
<211> LENGTH: 101
<212> TYPE: DNA
<213> ORGANISM: Artificial Sequence
<220> FEATURE:
<223> OTHER INFORMATION: G623D Target sequence
<220> FEATURE:
<221> NAME/KEY: misc_feature
<222> LOCATION: (51)..(51)
<223> OTHER INFORMATION: n is g or a

<400> SEQUENCE: 4
gagtgtcaac aaggagcctg ttgccgagcc tgacatcatg gccacaaatg ncgtggtcca     60
tgtcatcacc aatgttctgc agcctccagg taagtgtcgc a                        101

<210> SEQ ID NO 5
<211> LENGTH: 101
<212> TYPE: DNA
<213> ORGANISM: Artificial Sequence
<220> FEATURE:
<223> OTHER INFORMATION: H626R Target sequence
<220> FEATURE:
<221> NAME/KEY: misc_feature
<222> LOCATION: (50)..(50)
<223> OTHER INFORMATION: n is a or g

<400> SEQUENCE: 5
aaggagcctg ttgccgagcc tgacatcatg gccacaaatg gcgtggtccn tgtcatcacc    60
aatgttctgc agcctccagg taagtgtcgc atccccactg a                       101

<210> SEQ ID NO 6
<211> LENGTH: 121
<212> TYPE: DNA
<213> ORGANISM: Artificial Sequence
<220> FEATURE:
<223> OTHER INFORMATION: M502V Target sequence
<220> FEATURE:
<221> NAME/KEY: misc_feature
<222> LOCATION: (61)..(61)
<223> OTHER INFORMATION: n is a or g

<400> SEQUENCE: 6
cacgacaaga gggggaggta cgggaccctg ttcacgatgg accgggtgct gacccccca     60 ntggggactg tcatggatgt cctgaaggga gacaatcgct ttaggtaatt agttccatcc   120
c                                                                  121

<210> SEQ ID NO 7
<211> LENGTH: 20
<212> TYPE: DNA
<213> ORGANISM: Artificial Sequence
<220> FEATURE:
<223> OTHER INFORMATION: R124S Primer Fwd

<400> SEQUENCE: 7
ccaccaccac tcagctgtac                                               20

<210> SEQ ID NO 8
<211> LENGTH: 23
<212> TYPE: DNA
<213> ORGANISM: Artificial Sequence
<220> FEATURE:
<223> OTHER INFORMATION: A546D Primer Fwd

<400> SEQUENCE: 8
tctacacagt ctttgctccc aca                                           23

<210> SEQ ID NO 9
<211> LENGTH: 19
<212> TYPE: DNA
<213> ORGANISM: Artificial Sequence
<220> FEATURE:
<223> OTHER INFORMATION: H572R Primer Fwd

<400> SEQUENCE: 9
ccaaggaact tgccaacat                                                19

<210> SEQ ID NO 10
<211> LENGTH: 18
<212> TYPE: DNA
<213> ORGANISM: Artificial Sequence
<220> FEATURE:
<223> OTHER INFORMATION: G623D Primer Fwd

<400> SEQUENCE: 10
ttgccgagcc tgacatca                                              18

<210> SEQ ID NO 11
<211> LENGTH: 22
<212> TYPE: DNA
<213> ORGANISM: Artificial Sequence
<220> FEATURE:
<223> OTHER INFORMATION: H626R Primer Fwd

<400> SEQUENCE: 11
ctgacatcat ggccacaaat gg                                         22

<210> SEQ ID NO 12
<211> LENGTH: 16
<212> TYPE: DNA
<213> ORGANISM: Artificial Sequence
<220> FEATURE:
<223> OTHER INFORMATION: M502V Primer Fwd

<400> SEQUENCE: 12
ggaccgggtg ctgacc                                                16

<210> SEQ ID NO 13
<211> LENGTH: 19
<212> TYPE: DNA
<213> ORGANISM: Artificial Sequence
<220> FEATURE:
<223> OTHER INFORMATION: R124S Primer Rev

<400> SEQUENCE: 13
tccatctcag gcctcagct                                             19

<210> SEQ ID NO 14
<211> LENGTH: 19
<212> TYPE: DNA
<213> ORGANISM: Artificial Sequence
<220> FEATURE:
<223> OTHER INFORMATION: A546D Primer Rev

<400> SEQUENCE: 14
ctccgttctc ttggtggca                                             19

<210> SEQ ID NO 15
<211> LENGTH: 23
<212> TYPE: DNA
<213> ORGANISM: Artificial Sequence
<220> FEATURE:
<223> OTHER INFORMATION: H572R Primer Rev

<400> SEQUENCE: 15
cctccgctaa ccaggatttc atc                                        23

<210> SEQ ID NO 16
<211> LENGTH: 23
<212> TYPE: DNA
<213> ORGANISM: Artificial Sequence
<220> FEATURE:
<223> OTHER INFORMATION: G623D Primer Rev

<400> SEQUENCE: 16
tgcagaacat tggtgatgac atg                                        23

<210> SEQ ID NO 17
<211> LENGTH: 20
<212> TYPE: DNA
<213> ORGANISM: Artificial Sequence

```
<220> FEATURE:
<223> OTHER INFORMATION: H626R Primer Rev

<400> SEQUENCE: 17
ggaggctgca gaacattggt                                                    20

<210> SEQ ID NO 18
<211> LENGTH: 18
<212> TYPE: DNA
<213> ORGANISM: Artificial Sequence
<220> FEATURE:
<223> OTHER INFORMATION: M502V Primer Rev

<400> SEQUENCE: 18
ctcccttcag gacatcca                                                      18

<210> SEQ ID NO 19
<211> LENGTH: 15
<212> TYPE: DNA
<213> ORGANISM: Artificial Sequence
<220> FEATURE:
<223> OTHER INFORMATION: R124S VIC Probe (Norm)

<400> SEQUENCE: 19
ctccgtgcgg tccgt                                                         15

<210> SEQ ID NO 20
<211> LENGTH: 16
<212> TYPE: DNA
<213> ORGANISM: Artificial Sequence
<220> FEATURE:
<223> OTHER INFORMATION: A546D VIC Probe (Norm)

<400> SEQUENCE: 20
ctcggaaggc ttcatt                                                        16

<210> SEQ ID NO 21
<211> LENGTH: 18
<212> TYPE: DNA
<213> ORGANISM: Artificial Sequence
<220> FEATURE:
<223> OTHER INFORMATION: H572R VIC Probe (Norm)

<400> SEQUENCE: 21
cctgaaatac cacattgg                                                      18

<210> SEQ ID NO 22
<211> LENGTH: 16
<212> TYPE: DNA
<213> ORGANISM: Artificial Sequence
<220> FEATURE:
<223> OTHER INFORMATION: G623D VIC Probe (Norm)

<400> SEQUENCE: 22
cacaaatggc gtggtc                                                        16

<210> SEQ ID NO 23
<211> LENGTH: 16
<212> TYPE: DNA
<213> ORGANISM: Artificial Sequence
<220> FEATURE:
<223> OTHER INFORMATION: H626R VIC Probe (Norm)

<400> SEQUENCE: 23
cgtggtccat gtcatc                                                        16
```

<210> SEQ ID NO 24
<211> LENGTH: 17
<212> TYPE: DNA
<213> ORGANISM: Artificial Sequence
<220> FEATURE:
<223> OTHER INFORMATION: M502V VIC Probe (Norm)

<400> SEQUENCE: 24
tgacagtccc cattggg                                                17

<210> SEQ ID NO 25
<211> LENGTH: 16
<212> TYPE: DNA
<213> ORGANISM: Artificial Sequence
<220> FEATURE:
<223> OTHER INFORMATION: R124S FAM Probe (Mut)

<400> SEQUENCE: 25
tctccgtgct gtccgt                                                 16

<210> SEQ ID NO 26
<211> LENGTH: 16
<212> TYPE: DNA
<213> ORGANISM: Artificial Sequence
<220> FEATURE:
<223> OTHER INFORMATION: A546D FAM Probe (Mut)

<400> SEQUENCE: 26
ctcggaagtc ttcatt                                                 16

<210> SEQ ID NO 27
<211> LENGTH: 18
<212> TYPE: DNA
<213> ORGANISM: Artificial Sequence
<220> FEATURE:
<223> OTHER INFORMATION: H572R FAM Probe (Mut)

<400> SEQUENCE: 27
cctgaaatac cgcattgg                                               18

<210> SEQ ID NO 28
<211> LENGTH: 17
<212> TYPE: DNA
<213> ORGANISM: Artificial Sequence
<220> FEATURE:
<223> OTHER INFORMATION: G623D FAM Probe (Mut)

<400> SEQUENCE: 28
ccacaaatga cgtggtc                                                17

<210> SEQ ID NO 29
<211> LENGTH: 14
<212> TYPE: DNA
<213> ORGANISM: Artificial Sequence
<220> FEATURE:
<223> OTHER INFORMATION: H626R FAM Probe (Mut)

<400> SEQUENCE: 29
tggtccgtgt catc                                                   14

<210> SEQ ID NO 30
<211> LENGTH: 17
<212> TYPE: DNA
<213> ORGANISM: Artificial Sequence
<220> FEATURE:
<223> OTHER INFORMATION: M502V FAM Probe (Mut)

```
<400> SEQUENCE: 30
tgacagtccc cactggg                                                    17

<210> SEQ ID NO 31
<211> LENGTH: 32
<212> TYPE: DNA
<213> ORGANISM: Artificial Sequence
<220> FEATURE:
<223> OTHER INFORMATION: A546D ABY Probe (Norm) - NN complement

<400> SEQUENCE: 31
cttggtggca gggctcggaa ggcttcattt gt                                   32

<210> SEQ ID NO 32
<211> LENGTH: 33
<212> TYPE: DNA
<213> ORGANISM: Artificial Sequence
<220> FEATURE:
<223> OTHER INFORMATION: H572R ABY Probe (Norm) - NN complement

<400> SEQUENCE: 32
cttgccaaca tcctgaaata ccacattggt gat                                  33

<210> SEQ ID NO 33
<211> LENGTH: 31
<212> TYPE: DNA
<213> ORGANISM: Artificial Sequence
<220> FEATURE:
<223> OTHER INFORMATION: G623D ABY Probe (Norm) - NN complement

<400> SEQUENCE: 33
catcatggcc acaaatggcg tggtccatgt c                                    31

<210> SEQ ID NO 34
<211> LENGTH: 32
<212> TYPE: DNA
<213> ORGANISM: Artificial Sequence
<220> FEATURE:
<223> OTHER INFORMATION: A546D JUN Probe (Mut) HH compliment

<400> SEQUENCE: 34
cttggtggca gggctcggaa gtcttcattt gt                                   32

<210> SEQ ID NO 35
<211> LENGTH: 33
<212> TYPE: DNA
<213> ORGANISM: Artificial Sequence
<220> FEATURE:
<223> OTHER INFORMATION: H572R JUN Probe (Mut) HH compliment

<400> SEQUENCE: 35
cttgccaaca tcctgaaata ccgcattggt gat                                  33

<210> SEQ ID NO 36
<211> LENGTH: 31
<212> TYPE: DNA
<213> ORGANISM: Artificial Sequence
<220> FEATURE:
<223> OTHER INFORMATION: G623D JUN Probe (Mut) HH compliment

<400> SEQUENCE: 36
catcatggcc acaaatgacg tggtccatgt c                                    31

<210> SEQ ID NO 37
```

```
<211> LENGTH: 20
<212> TYPE: DNA
<213> ORGANISM: Artificial Sequence
<220> FEATURE:
<223> OTHER INFORMATION: R124S Primer Fwd

<400> SEQUENCE: 37
gaccctggag tcgttggatc                                          20

<210> SEQ ID NO 38
<211> LENGTH: 24
<212> TYPE: DNA
<213> ORGANISM: Artificial Sequence
<220> FEATURE:
<223> OTHER INFORMATION: A546D Primer Fwd

<400> SEQUENCE: 38
cgggaaggag tctacacagt cttt                                     24

<210> SEQ ID NO 39
<211> LENGTH: 21
<212> TYPE: DNA
<213> ORGANISM: Artificial Sequence
<220> FEATURE:
<223> OTHER INFORMATION: H572R Primer Fwd

<400> SEQUENCE: 39
tgaaataccc caaggaactt g                                        21

<210> SEQ ID NO 40
<211> LENGTH: 18
<212> TYPE: DNA
<213> ORGANISM: Artificial Sequence
<220> FEATURE:
<223> OTHER INFORMATION: G623D Primer Fwd

<400> SEQUENCE: 40
aggagcctgt tgccgagc                                            18

<210> SEQ ID NO 41
<211> LENGTH: 22
<212> TYPE: DNA
<213> ORGANISM: Artificial Sequence
<220> FEATURE:
<223> OTHER INFORMATION: H626R Primer Fwd

<400> SEQUENCE: 41
ttgccgagcc tgacatcatg gc                                       22

<210> SEQ ID NO 42
<211> LENGTH: 16
<212> TYPE: DNA
<213> ORGANISM: Artificial Sequence
<220> FEATURE:
<223> OTHER INFORMATION: M502V Primer Fwd

<400> SEQUENCE: 42
gttcacgatg gaccgg                                              16

<210> SEQ ID NO 43
<211> LENGTH: 18
<212> TYPE: DNA
<213> ORGANISM: Artificial Sequence
<220> FEATURE:
<223> OTHER INFORMATION: R124S Primer Rev

<400> SEQUENCE: 43
```
cccggcagct tcaccatc                                                         18

<210> SEQ ID NO 44
<211> LENGTH: 21
<212> TYPE: DNA
<213> ORGANISM: Artificial Sequence
<220> FEATURE:
<223> OTHER INFORMATION: A546D Primer Rev

<400> SEQUENCE: 44
aagagtctgc tccgttctct t                                                     21

<210> SEQ ID NO 45
<211> LENGTH: 24
<212> TYPE: DNA
<213> ORGANISM: Artificial Sequence
<220> FEATURE:
<223> OTHER INFORMATION: H572R Primer Rev

<400> SEQUENCE: 45
gccccgatgc ctccgctaac cagg                                                  24

<210> SEQ ID NO 46
<211> LENGTH: 24
<212> TYPE: DNA
<213> ORGANISM: Artificial Sequence
<220> FEATURE:
<223> OTHER INFORMATION: G623D Primer Rev

<400> SEQUENCE: 46
cctggaggct gcagaacatt ggtg                                                  24

<210> SEQ ID NO 47
<211> LENGTH: 20
<212> TYPE: DNA
<213> ORGANISM: Artificial Sequence
<220> FEATURE:
<223> OTHER INFORMATION: H626R Primer Rev

<400> SEQUENCE: 47
cacttacctg gaggcgcaga                                                       20

<210> SEQ ID NO 48
<211> LENGTH: 18
<212> TYPE: DNA
<213> ORGANISM: Artificial Sequence
<220> FEATURE:
<223> OTHER INFORMATION: M502V Primer Rev

<400> SEQUENCE: 48
agcgattgtc tcccttca                                                         18

<210> SEQ ID NO 49
<211> LENGTH: 27
<212> TYPE: DNA
<213> ORGANISM: Artificial Sequence
<220> FEATURE:
<223> OTHER INFORMATION: R124S VIC Probe (Norm)

<400> SEQUENCE: 49
cgacttctcc gtgcggtccg tgtacag                                               27

<210> SEQ ID NO 50
<211> LENGTH: 16
<212> TYPE: DNA

```
<213> ORGANISM: Artificial Sequence
<220> FEATURE:
<223> OTHER INFORMATION: H626R VIC Probe (Norm)

<400> SEQUENCE: 50
tggcgtggtc catgtc                                              16

<210> SEQ ID NO 51
<211> LENGTH: 17
<212> TYPE: DNA
<213> ORGANISM: Artificial Sequence
<220> FEATURE:
<223> OTHER INFORMATION: M502V VIC Probe (Norm)

<400> SEQUENCE: 51
tccccattgg gggggt                                              17

<210> SEQ ID NO 52
<211> LENGTH: 40
<212> TYPE: DNA
<213> ORGANISM: Artificial Sequence
<220> FEATURE:
<223> OTHER INFORMATION: R124S FAM Probe (Mut)

<400> SEQUENCE: 52
cgacttcgac tttctccgtg ctgtccgtgt acaggtacag                    40

<210> SEQ ID NO 53
<211> LENGTH: 16
<212> TYPE: DNA
<213> ORGANISM: Artificial Sequence
<220> FEATURE:
<223> OTHER INFORMATION: H626R FAM Probe (Mut)

<400> SEQUENCE: 53
tggcgtggtc cgtgtc                                              16

<210> SEQ ID NO 54
<211> LENGTH: 17
<212> TYPE: DNA
<213> ORGANISM: Artificial Sequence
<220> FEATURE:
<223> OTHER INFORMATION: M502V FAM Probe (Mut)

<400> SEQUENCE: 54
tccccactgg gggggt                                              17

<210> SEQ ID NO 55
<211> LENGTH: 20
<212> TYPE: DNA
<213> ORGANISM: Artificial Sequence
<220> FEATURE:
<223> OTHER INFORMATION: A546D ABY Probe (Norm) - NN complement

<400> SEQUENCE: 55
agggctcgga aggcttcatt                                          20

<210> SEQ ID NO 56
<211> LENGTH: 22
<212> TYPE: DNA
<213> ORGANISM: Artificial Sequence
<220> FEATURE:
<223> OTHER INFORMATION: H572R ABY Probe (Norm) - NN complement

<400> SEQUENCE: 56
acatcctgaa ataccacatt gg                                       22
```

<210> SEQ ID NO 57
<211> LENGTH: 16
<212> TYPE: DNA
<213> ORGANISM: Artificial Sequence
<220> FEATURE:
<223> OTHER INFORMATION: G623D ABY Probe (Norm) - NN complement

<400> SEQUENCE: 57
cacaaatggc gtggtc                                                    16

<210> SEQ ID NO 58
<211> LENGTH: 20
<212> TYPE: DNA
<213> ORGANISM: Artificial Sequence
<220> FEATURE:
<223> OTHER INFORMATION: A546D JUN Probe (Mut) HH compliment

<400> SEQUENCE: 58
agggctcgga agtcttcatt                                                20

<210> SEQ ID NO 59
<211> LENGTH: 22
<212> TYPE: DNA
<213> ORGANISM: Artificial Sequence
<220> FEATURE:
<223> OTHER INFORMATION: H572R JUN Probe (Mut) HH compliment

<400> SEQUENCE: 59
acatcctgaa ataccgcatt gg                                             22

<210> SEQ ID NO 60
<211> LENGTH: 16
<212> TYPE: DNA
<213> ORGANISM: Artificial Sequence
<220> FEATURE:
<223> OTHER INFORMATION: G623D JUN Probe (Mut) HH compliment

<400> SEQUENCE: 60
cacaaatgac gtggtc                                                    16

<210> SEQ ID NO 61
<211> LENGTH: 41924
<212> TYPE: DNA
<213> ORGANISM: Homo sapiens

<400> SEQUENCE: 61
agagggaaca gaagcatcta ggagagattt ggaaagaaca cctgcaggat cttggtgact     60
gattgcacgt gggggaccag agagcaggga caggcaaaac tgaatgcaag gtttccaacc    120
ttgagcggca ccacaggcaa gaatgaagaa atgaagaagg ggagctggac gaaagagcca    180
agggatttct gcattttgga atgaattgct gctgggtggt gtccatttcc ctgaaggcct    240
ttatcctacg tgcaagaaaa ctcgtgggaa gcagaggaaa ggcatgtgta agccaacaat    300
catctgtggg catccttcca ctaaagtatt tgaggtcagg caactaaagc aacctcaaaa    360
gtgcctctgg attcttctta gatattttag ctgagccaaa tcaatgaaac tctcatgaaa    420
aatcggtttc cctggaaaat gaattgggt tctaaccaac aagtagcatt tggcaggccc    480
tgattaagaa agccagtgtt tggagaagtt gtgaaaacag ccaagtcatt taagaaacta    540
aacactgggg cctaatgcca ttctagggct gcgacggctg ttctgttccc atcaattgca    600
gagcccgaag cctcaagttt gttttaagtt cctgccatta caaacctgtc gattatccca    660

-continued

```
gcctcccttg cgggctttga aaagagagaa gaatggaagg tgactgtggc caatttcccc    720
tccctgtcca gtgtgtggaa gacactgaat atgcaactac tgaccttgtg cctgggcatc    780
ttgaaggtct tccacaaagt gagctgggcc tcagcggaag atgagagttc ctctgtggtc    840
acttcactgg tacacatttt caggtgtatt tcgtttcttc catgcctaca taaattgaat    900
cctctgttaa ccacctctga gctcatagct atttaacatg accctgtagt cctgtgcata    960
caaatcacct tgggatctgg tgaaaatgca gattcagtgg gtcttgggag gttgggaggt   1020
tataagattc cacgtttctt catgagagct agaaaaaata aataaataaa taaaaaattt   1080
ttaaattttc cacatttcta atgaactctg gggttgtgct gatgatgctg ttttgcagat   1140
cacattttga gtggcaagac tgtggaaaat ccttgagaaa tcaatccaaa atcccctaaa   1200
tggtactaca atcacacctt aatgttagta aactgagatg tttcttacct ttatttgtaa   1260
catggaaaaa acaattactg tatatgaagt accattctaa gttctgtgtg ttacacaagg   1320
gatggcaatt tccccaaaa tttgattcac atcttttcat ttggatatct cttgccaaaa   1380
ctcacctttt tttctcccta gcaagtcttg gggagctgaa ttttaagagc tctttattta   1440
gctatatggt ggcctctgaa aatgattttg actgtatctt ctgtctccat gtatgcccaa   1500
gcatcaccag gaactttagg gagtaaggaa aaggcaggcc tggtgtcagc tgggctgcag   1560
atgccagctc tcccaccaac aggcccagaa ccagtttctt tcctaggttc ctttgtgaag   1620
aacttgttgg aactactaat ttatcatgat gcataaagct tgttgtcata ccctacagta   1680
ttattttcaa aacctgaatg ttttttggtga cctttcatgt gccacaaaat gtaaaagcag   1740 tcattttta aaaagtgctt gaaaaagtct agtaaagatt cttccaagca agcctcactt   1800
tctcctgttt agattgttta atctggaagg aaaaaattct ttctcaaatg cagggtttc    1860 tggtgctctg tgtttgcctg gttggctctg ggtcatctgg ggatggaggg tccctgctct   1920
tacctccagc agcatcactc ttgtctccaa agaagcagca acctcaggtg ggagaatggt   1980
tatactcaca gcattctgct tttcatgttt gaaagagggg atgggtggtg gggcatggat   2040
gtgggatttt aaaaaaatat ctaaaccata aataaagtat tactgcaatc tctttactga   2100
gctcatggaa aaactcaagt catcgaatgt tagttttgca gactgcagaa gtgaggtcca   2160
gtgaacttgc ttgacttgcc ctaaatcttg ctagagagag agctggaacc agatggcagg   2220
gctcctggcc tcttacatac aaggagcatt tttcctagaa actgcaatgc agccaaattc   2280
tactggtctc aggggaaact tgttctggga gtcagcctga gcttgaatcc ctttgggttc   2340
ttcccattat cctatgccaa gcagtcatgc tgaaaccgag aaatgttttg ctttcaataa   2400
atgaaatgag cattttcaga taattatttc tgtagttgct caaaactatc atattgtttc   2460
attgaaccct actatataga acaatgactg gggagaggta ataataataa tagcaatgca   2520
tatttattgg ccatttttact tgaattgtat catgtaatct agtttagagt cctgtgaggt   2580
aggttttatt atcctctcta tgaggttgaa taacttgccc aagaccacac agctaggaag   2640
tagaaagact ggtatttgaa cccatcttct ccttttcttc ccttcctcc tcctcctctc    2700 ttccaacacc tgctcccaag gaagctcatc cagtgcatga ctttagctac cacctgctcg   2760
tagtggtgac tcaaatctgc atctccaatc ctcataccta tcctgagctc aagacctttg   2820
aatatagctc cctcctgtcc atccctcctg gaaatgcagg tggcttgttc acacataatg   2880
tgaacacaaa tggagcactc tcctcacaca cccaaatgtg caccttcacc agcgtgccca   2940
gcacaggcat cccttcctgc cagctatgag cctcgaggtt agctctactc cccctcccta   3000
accctgcatg cccaaggggt ttccaagtct aatcaatgct accactaaaa tctcccatac   3060
```

```
acctgttccc tcctctccac tagcttgatc actcccatg caggccctca gttgctttat   3120
gctctcagta ggccctcctc cagtgcccac actctctccc ttctccttcc caccttcttt   3180
ctaccagagt tctaacctct ccaagccccg cttgtctttt tctttccctg gctgccatcc   3240
taactcgccc cttccttct cagacaagct tctacatgct actcatctct ccatcaaacc   3300
accatattcg ggctttggcc atctgctctc cacagccaag tccccagtgg cctctctgct   3360
tctgacacag tgaaagccat tcagatctgt cttgttggca gcattcctca ctttgagcag   3420
cgccctccta ctaggatacc cctccttgac tacaaccca cattctctac ttcctgggct   3480
cttctgtcac tggaggatga ctcccaggtg tgaatcttca tcccgcgtcc ctcactcaag   3540
cccccgatcc tcatatccag ctttatcctc atgggatgct tcaccaggat gagtcataag   3600
cacctcagac tcagggtgtc ccaaaccact catctacctg gcaagcctgc actctgcatg   3660
tgcctcattc tgaacatggc accatcacct gctgcaatgt ccagaccaca aacaccctac   3720
aatatccttg actctccttt ctccccttct ccctgtatac agactccaaa ttctattgag   3780
actattacct cctacacccc tcacatttgc ccagccttcc ccatctctgc tctaccacc    3840 atagttcaag ctctcccatg gtcccttcct ggttacctgt tcttcttgcc tccttaagcc   3900
tctcatgaca ctggccatgt cacttgcctc cacccatcac ccgctaggct cttagctgga   3960
gtctgggccc tgctaccttc ctcccctttct tccctaccct tgactccacc tccctgtgct   4020
tcagccaacc agataacttg agtttcgtga atgcatgcct cagtttacct gattaactca   4080
ttttcatctt tcaggcctca gagcaggtat caccctgtca gggccaggtg cctcttctta   4140
gctcccaaag ccccagctac tcttcatgga acatcattgg cttgggctac ggatcttccc   4200
aaattggagc tttttcacaa agggcttagg tctcactcat tctattaatc catctgtgtc   4260
tccccagggc tagcagtgcc aagtaactga caggtgatta atagatgctt gggtaagtat   4320 cacctctttta ccatgtgaca atttgtttac ctgccttgag ctcctccagg gcaggactct   4380
tgcctttgca gaatctatct ggcaggtact gttgcagaga tgtttactga agaagggaat   4440
gaattagtac caaggtgagg accccacccct tccccacggg ctccaaaagc agcttagagc   4500
ccaacaaaac ctgccccaca ttttttggcgt ttctgtggat cacacgattt actcatctgt   4560
ctttcaatga gcatgacagg tggggtgggg gtggagggat tagagattga ggagctgggg   4620
agggtggtca gctcctgggg tgcagaaaca agtctgatgg gccatggtgt ctgggaatc    4680 agcactgcct cccctcaccc ctccctgcag tgttttgtag cctcaagatc agtgagggaa   4740
tcttcgggcc cccagcatgc aggaccgaag cccccgagac agctgtccct cagtcccaag   4800
gtccccattt ggaagcagcc acaggaggcc taagggacct ataccttgg tttgaggaag    4860 actgtggcga gggagagagg gagggagggc tggcagtgag ggcaagggct gggaaaactg   4920
agcacgggca cagtgcggga gcgggtgggt gcccagggca gccaggggcg cacgggttgg   4980
gaggcgccag gcgccccgcc ctccttgcac gggccggccc agcttccccg ccctggcgt    5040 ccgctccctc ccgctcgcag cttacttaac ctggcccggg cggcggaggc gctctcactt   5100
ccctggagcc gccgcttgc ccgtcggtcg ctagctcgct cggtgcgcgt cgtcccgctc    5160
catggcgctc ttcgtgcggc tgctggctct cgccctggct ctggcctgg gccccgccgc    5220 gaccctggcg ggtcccgcca agtcgcccta ccagctggtg ctgcagcaca gcaggctccg   5280
gggccgccag cacgggtaag ccgagccgcc tggccagggg ctgcggaagg tcaggtagtc   5340
ggggctcgga gcgcaagccg ctgggggcat tgaactgggc tggggcgcca gggacaaag    5400
```

```
cccgaactaa aaaccttgca gcatggagcg ctcggacacc agccctgcac gcggtggaag   5460
gagagaggga gggaggtgga ggaccatgga gggaaagcgg gaggccgccg ctttgtagaa   5520
gggagtgggg aagtggacca gagactttcg acgcaggcca agagcctgag acggacagcg   5580
cttccagctt ctcctcccag ccactgcaga aaggggggaaa tggcaactct ttggccataa   5640
tcaccgtggg agggtgccaa gggcaaagcc cacccagcag tacacctatt ccaacccagc   5700
caggcccccg gccagcgact ccagacaaga acctgggcca cacacggtgg cagcatctaa   5760
ggtgccccag gctcctgtgc tcctggccag gccctgcact cagacactgc tggcacccga   5820
cactgctctc tgggtacagc aagggcaatg tggcacttct tgtcctgccc gatgaagagc   5880
aggagaatgc actgggccct cacacacact gttcaaatgg ggaaactgag tcctgagtgg   5940
ttccactttc ccacagtcct gaagtgtgca ctggagccag gattggagtc tgtcttaaag   6000
taatagctgg gtttgtaaat gtaggacact atcattgcag gaattccttt gagaccctga   6060
agatgtgttg gctttaggag acaaactcaa gcagaaggtc tggtctgata gtggccctaa   6120
tactgaccca ggcagaggca ggcaacattt ctacctcaaa aaccaggcca tacctgcgtc   6180
acaaataccc aggctttgct gcagcttcca gcctacctgg ttgcaccaac ttcttttttca   6240
taactaggta aaactatata tgagtagaat cttgtagtga ctcctcagag gaagcctaaa   6300
taccatcggg gtctggcgtt cacacccaca agcaatgccc aaacctccaa gagactgggc   6360
agatctgtgc tcaaatcaaa actcattgtt gggggtgata gagttgactt cacaggccct   6420
gaaagtcttg gctccttgca ctaggagtgc tctgggtacg ggtacaggct gcccccttgta   6480
gggcatagtt gctcttgttt cctctacttg tggcttatg gtctaggcct ttcaggagtt   6540
tggggctctg gcggagaggg cctgctggga gcacatctgg ccaccctgca gagtgaaatc   6600
aaaccaggcc tggctgcaac ctcaacaccc tcctggaaag aggagaatac tgggggatatc   6660
ctggggtctt tctggaagtg ggagaatcag ctttgacttg ggcagtgtgc agaatagagt   6720
gaggggggat gtcagaaaga tgagagggat atgaggcctc aacatcaaaa tgcaagcacc   6780
tggcattttt attatctctg cccacctctc cgttggtctc tctgcctttc ctgccaatga   6840
attgtgttat gtttgggtgc ctcaatttgc ctaggagggt tctatttctt ctgtatcttc   6900
gccactaagt caggagaaga tccttatagc atgccctgca acagtgtcac ctgtaagggc   6960
atctctctgc acagccacag tgaaggatcc tcaaaggtat tgagggcttt ccatcaagag   7020
ccatctttac agcaaacctc tttcccttca gagcccagaa gagtgctgac cagctggaaa   7080
acagggtttt tttcttaaat gcagatgctc ttgattatga gttccagata ttagatcaac   7140
ttccccacca taccctgca ggcaaagcct cttaattagc ttcctgcagc acagctggaa   7200
aggcctattg taatctgtga tgggcagagt aatctaagaa gtcacaggag caccctgtc    7260
ccagtagaat ctggatgcgc aggcacatga accatggcaa aatggttgca ggcacagttg   7320
tatttactct gatctaactg tccctgttaa tgccacaggg ctgcctggcc tggcacacag   7380
ggctgtggcg ccttgtgcaa atggataacg ttgttctagc tccagccttt cattcaaagt   7440
gaaaactgtt agaaagggaa ggaaaacttt gctatttaa ggaattgtag cgtgctgcct   7500
gatatgaagg aagaaataac agctgtgcct tgcttgtgcg cagcactcga ttgccgcttt   7560
tgctttcgac ctcaccacaa cacagtgaga tctactgttc atgttcccat tttacaggag   7620
gtgaaactgc agcttagtga ggtagagagt gacttagttc agacacagaa tgctgttggg   7680
agagtaataa ctatgatatg gtctcttgac tcccagctat atctgtgttg ctataggaa    7740
ggggaaaaat aatactgaaa gagaagtaaa aatacaatca cacttccaaa catcaaccac   7800
```

```
caaaaactga actgaatttc ctgaagcact tggttttcaa atctaagctg aacatcaatg    7860
ctgttattct tgaggcccag aagcaacttg ctcatttcaa ttaagcttca gcatgaactt    7920
cctatgtaca cagcccaccc acactccccg atgtgagaag gagagggtca cagccgcccc    7980
cagcctctgc tgctgccaca aggacagcag cagtggaaac attcagcaaa ggaatgttgg    8040
agccacatcc acaagagact cactgaagat tcgccaaacg cctacggaaa gtggcaggga    8100
attcattgac agtaattgtt tcctgcttga tcagattgaa gagcttctgg gattctgtaa    8160
caataaatag gaccgggggc tggagtatgg ccagcaagga ctcttcaggg gttattcagg    8220
gactgtctaa cctgtgaatc ctaggcagca aacagaaacc aggtattcag aaatctggag    8280
gatttggtca ggcccagcta ggactaggga ggcatgggcc tctgctggct gtggtccctt    8340
ctccagcctt cacttctctt gtccctagat ccttacatgg attcattaat gctcattgtc    8400
cctcctgggc ccactcactt tcacctgttg aacaaaaaac tggccaagag gtgacagtca    8460
tatcaccgca aagagacag ggcagagaaa tgaaggggca gaatggactc ccacccaaaa    8520
gcctgactct gaatatttga gaattgttca agttcctgca gaggaatcat gatggggaca    8580
gtaggtgtag tttttactgc aatattggtg tcttcttaac aaatacgctg cacatcaagt    8640
gatgtctgtg atggcattc ttaaagtaac agggaaattg atgttaaaga aatacttcat    8700
cctttgggtg atacctgaag ttctctgagc ttggaggtct tgtgaaagcc ctcagtattg    8760
tttgttttat ttgctttcct ctgacttgtg attcagtcag atgcatgcct gcctctggct    8820
caggaagatc aaccctctcc tgactgacca cgcctctcct gactgaccac gtagcacagc    8880
agcttccttt ccctaggggc tcctaatgaa gctttcacaa tcacctggcc tgagcacagt    8940
ttgggtcagg acttggtata cttgaaaaaa acatgcaaaa ccaaaatcct gtggttctgg    9000
aaaaggcttc ttagcagaac ccccagacat ttacactctg cttttcaca gggtccctga    9060 ggattctttg gatctgggta gtttgggag cagtatttc aacaagttca tttcgtgctc    9120
cttctacacc ctgcctggat gctaggcccc atctagaatg tgaacaacag aacaaggcag    9180
aacacttgtc ctcaaggttc tgttgagtgt tagatgcaga aagagacac ccccacctc    9240 cccgcatcac ttacaggaat tctgtttgga acccaacatc aaataaggac cgtatccact    9300
gtcagaggat gggaagcagc atgtcatctg ggacattgga gaaaggctcc tgggggaagt    9360
gggacttgag ctgtgatcta agtaatgaac aactgagagt taaatgggag agcatcccct    9420
atcagggtcc tgagagcaac cagccatggt ttaaaccagc tataaagcct cgggtttata    9480
ggatagacag taacaatggc ttgtctttgg gagccaagca gctggtccag gcatgcagag    9540
catgtctgta tggagagctg cctgagagat gcttttgttt acacttatca attgcccatg    9600
tcaaagaagg atatgtacat gaagttacat cagtatgtaa gagagatttt aacaattttt    9660 gcagggaag ctttcatggg ggctgatggg aatctaggta aacagaacca agtctaaac    9720 ccaagatatc cccagtacca agactgaaat gactctctcc tctatctcta gaaagttcca    9780
gtgacccaag gaggcaaaca cgatgggagt cattaaagtg gggtggacgt gctgatcatc    9840
ttcctaattc tgctgctttt gttttcagcc ccaacgtgtg tgctgtgcag aaggttattg    9900
gcactaatag gaagtacttc accaactgca agcagtggta ccaaaggaaa atctgtggca    9960
aatcaacgtg agtatctgta accagccagg agaccaagct gtatgcacgc tggctgcagt   10020
tccccagggc ctgggccagc cttctagaag gtcaggttgc ctaaaaagcc atgaagatgc   10080
atgtgcgaac atgtctggga cctgcgtgct agggagtggc atttttagga agctggccaa   10140
```

-continued

```
ttttgttttg cattttaag gctgctgaca agacttggag acattttca gggctggttt    10200 gggtttgcaa gaaacatgaa acactgcgtg tgtgtgtgtg tgtgtgtgtt tctcaatcct    10260
cataaaataa tacagatatg cagtggagaa gccaccagca tgtgactctg gaaagaaag    10320 cccattggtg aatctgtact aaagaatgcc atccctatct tacagtccta aggtaaacac    10380
cccaaaaaga cttagagcac taaacatatg cagattatga gacagcatag catataatat    10440
ttgcacagac ttcctcattc aaaccctagc tctacctggg ccagtcgatt catctttaga    10500
accctccatt gctttacctg aaaagttcgt ataacaaaag gacccaccttt atggggttgt    10560 tacaaggatt gaatgaaata atgtacataa gagactgaat atggtgccca gcatatatca    10620
gtgctcaata aatgctagct actattatta ttatcaccct agatttgcaa atctagacca    10680
cacaagcaga agtaagagtg ccaacgggt gtggaccagt gtggttacaa tagggcttgt    10740
tgatgtctgt ttcagcaagg agggaggcag cttttacccc actgcccagc tccctggtgg    10800
aatcaggtgc atgttctaac aattctgggg aaacctaatc tgttttggca ctgtcaacag    10860
atctcaaagc tggctgtctc ctatagctag gaagatgtgt atgacaaatc tcctgagcca    10920
cttgtgaagg cctgaccttc ctcctgtctc catacataat gggatgatta agaaactcta    10980
agccactctc ttaagcactt tcaatgtta gggatttta agtttattgt tgtgacattg    11040
cttttgagca gacatctcct ccaatttaat agccaactga agaagagaa aatgctcttt    11100 ccttaaactg tatgtggaaa taatattcc aatgtgtgac cctgattatg ttaggcaatt    11160
agcaatccta atatgaattg agggaagttg ggattcatgg cacagctggg gagataccag    11220
cagtccctgg gagcctgtcc agggcaggtc catggcagct tgctccatgc ctgattgaca    11280
gcccagcctg caagctaaaa gttgagtgag ctaggaggac acactgccaa gattcagcta    11340
acagacaccc agcgatattc ttgctgctat gaacaaaagg agactatgca aattatacac    11400
cacccattct tccaggatgc ctgacttaaa aaataagaaa aaagatgggc cgggcacagt    11460
ggctcacgcc tgtaatccca cacttgggg aggccgaggt gggcggatca caaggtcagg    11520
agacagagac catcctggct aacatggtga acccgtct ctactaaaaaa atacaaaaaa    11580 tattagcggg cgtggtggcg ggcacctgta gtcccagcta ctcgggaggc tgaggcagga    11640
gaatggcgtg aacctgggag gcggagcttg cagtgagcca agatcgtgcc actgcagtcc    11700
agcctgggtg acagagtgag acaccgtctc aaaaaaaaaa aaaaaaaaag aaaagaaaac    11760
ctttagtact gattgatttt ttcccatgtg tgtatattat ctactcaaat taacaattaa    11820
ttacttaatt aaaacacaaag ccaggcctca cctaattgct tcttggaagg tgaccagagt    11880
gctagtgcca agcaaacaac tcttctatat ctcaagagcc ctgggcttca gagggccatc    11940
ttttttgtta attcaagttt ctctgaaaat ggagacccgt ttatgatgac aagctggcta    12000
cagggtagca tctgccacac tgtttcgggg gtgccgctgg gctgaagcat ttgcccagct    12060
agttaacaat agctcgataa cattccctat cagtgtccag gctgagaata ctgtcagtga    12120
tgagtcgcct tggctcttgt acctgtatct ttgtgtgcca ggacaaggca caagcaacag    12180
agctgtgtgt tgccaaaatg ttcctgatga gcaggtcaac ccctcgggg caggtttgga    12240 tatgataatg tggtgatgtg gtggcgcagc tcccttaccc agtgagcaca aggggagtcc    12300
tctaggaaaa ggaagaaatg tctggatgag gtggggagat ggggttcaga gtggactcag    12360
gcaaagcccg atgcccagtc ccagctgttg gcctagtctc acaaagccag aaggatatga    12420
catttacatt caactcttga atttgtggcc actgctttgg gcaacttcaa agagagaaaa    12480
tgaagataga aaaatattat ttgatataaa acttctagga caagagaggc ccttcctgga    12540
```

```
acattacatg tagtattagg aaggtggagc tgccctggaa aagatccaga gaactcagag    12600
agaggaagag gtggaaccca tctctgttct tgtagagagc tcagtaagag tggcttggca    12660
gggctcctgt gtacctgaga ccaagaccag tgaggaggct actgtctgac caccatacgg    12720
tcagaattca gtgccatggg tggtcaggtg gaaggggga aggactgtgc tggctggagt    12780
tgatgttatc ctggggaaag taggtcccta gatgccttta gttgagtgag gagcagactg    12840
ggaaatggga gcacagtagt ggttggggca aaaaggactg tctctgcatg aggtccatag    12900
gcagttggaa ttttctcagc aagactccag agaaggaggc tggagcagag gtgtatgttg    12960
ggatgaaaag gagtaaagta tcatggggga ggaggcagct caggttgtca agggtcaaga    13020
aaccagaagg agaatttcac cttggaagca gacaacgggt accaagcata caggggaata    13080
ctttgtggtg agaggtcaca cagagataca ggagccgacc tggtgagaca ggagcctgga    13140
gccacctgcc tgcttttgtg aggccccaga ctccactgct atcatcaggt gaagctctgt    13200
tgcctgcaca caaaagcttt tctgcattta caaagagaga agggcctgag tttctggtgc    13260
aatgcgtcaa gctgacatat ggactttatt acaggaagtg gttaccagtg ggtccctatt    13320
tagtggctgt tattgtgaat tttattgttc ggaaattcac tttagcattt atttcagatc    13380
ctaaatagca ccggagtgat acaatggcta atcaaacaaa gagggctgtg gggagcagac    13440
agtcagcatc cccctctgtg atttcaggcc ctggtttgat tagtagccat aaaattttt    13500 acgtgtggca ctttgagcaa aggtgcagga aattgtggtc aggaagcctg gctgcctctc    13560
gacaggcttc ctttgtgcta gccccaggga gaggaggcct atttaacagc caagtccaag    13620
ttgacatcat gggactggaa tagtcatagc aggagctcag acatcataaa cgtggcatag    13680
ggagggctgg tggaggagct agcgggtatg ggtggcagct attcattcca aaagtcttga    13740
aattgtttca cgagcaacac atttcacaag tgcgaagccc ttctctggag ccaagatgag    13800
ctggcagagc actcctgttt ctctagtagc aagtgttcct ttgcccaggg gcaaaaatat    13860
taatactcct tcagcactgc attaatgctt aaagatttaa cttttaaaga gatcagctgg    13920
tgcatggtcg agcttttcca tcagctggca gggcttttc agtaggtgtc cttctgggca    13980
gggcactggg gacagctgac gtgaaggtga agaagagctg tcgttttcct cccttatatc    14040 ccacaaccatt ggtcccaaga ggaaaaaaaa gaagatggtg agaagtcatc caagcagacc    14100 ccagaccat actagtgcct ccttcctgt ttcatatccc tgtgcagcca gctgggatct    14160
cttgaataat ctgctctggg ggcactgaga ttggacatac accaaacagc ggagatcgac    14220
caaacgcctc tgttgggcag tgtttcctga gggttctgtc ccattctgta aactaggagg    14280
ctgactagct gacaaggaat tttattctgt tgggtattta catgaaccta tgtgccacct    14340
ggggtaagac cctgtggtag gtagaaacat gacttcccaa aaatgtccac atcctaatct    14400
ctaattctgt aaatatattc ccttactgga aaaagagact ttgcaggtgt gattaaatta    14460
aggatcataa gagggagaga ttatccagga ttatttgatg agtctaatat aatcatcagg    14520
gtacttaaaa gagggaggca ggctgtgcct ggtggttcac gcctttaatc ccagcacttt    14580
gggagactga ggcgagcggg tcacgaggac aggagttgga gaccagcctg accaacatgg    14640
tgaaactccc cctctagtaa aaaaaaaaat acaaaaatta gccaggcatg gtggtacaca    14700
cctgtaatcc cagctactca ggaggctgag gcgggagaat tgcttgaacc caggaggcag    14760
aggttgtggt gagctgagat cgcaccactg ccctccagcc tggcaacag agcaagactc    14820 catctcaaaa aaaaaaaaag agggaggcag tgggatcaga gtcagagaag gcaacgtgat    14880
```

```
gatgaaagct gacatttgag tgatgcaacc acaagccaag gaatgcaggc agcttctcaa   14940
agctggaaag gacgagcaat ggattcttcc ctacagcctc tgtgaggaat gcagcctttg   15000
attttaaccc cataaggccg atttctgact ctagcctctg gaattgtaag ataatttgca   15060
tgatctcaag ccactaaatt tgtggtaatt tgtcacagaa agcaatggga agccaacaca   15120
ggccttattt gttgacttat agatgcattt ttctttattt caatgtactt ttatcaatgg   15180
tctcatgtag ggtattgctt tcaatgaaga tattaacata gtttcaactt taaggtttat   15240
atctggagtt tctttagaag cttcacaact gaccacttag taaacagtaa gcatctgtta   15300
agtgcttctc atatgtaagt tcattcaatt ctcacaatca cactataaga taaatatgat   15360
tattagccca tttacagatg aggagacagg ctcaaaagac ttttatgcaa cctggtcaaa   15420
gtcattcact ggtaagctga ggaggtctgt ccacttcctt ttgctgcccc caggggtat    15480 caagcctggc agttagtgtc agcgacttag gaggtgaaca agtgagcagg cctgtaggac   15540
ctggctaaac tgccccaggt ctctgtctac agcctcaaac ctgtggctgt gggtcccaga   15600
gacaaggcct cctcagcatc agagaaggat gcctttgtct cagggtcatc aaccttctcc   15660
aggttgctca cccctgctg taaagggat ccccaagacc gctcatcaga caaggagctt    15720
gggaactgag gagacacagt cagcctccag gagtgcccaa aatgccctca catgctgcat   15780
acagattgcc acaaataaag tacatccaca ttctgaagac tctgtcctca tcaccaacca   15840
ggctggcccc tggtgagggc tgtagtggtt gaggcctttg ttggtagaca gtaggttaaa   15900
gcaagccatg attttctatt gggaggcttc agaatcagct cagctgtgtt ccaagacca    15960 ggagggcaga aagcaaacca tcccaggcaa gcagtccatg ggccatgtca gatgtctaga   16020
cgttatgggt ctgtgtttgc tctgccattc ctctcggaaa ctatgatgcc ctgtatggtt   16080
taccttcagt cacaggtgac tggcctacag ggccattcct tgttccaacg acttctcgag   16140
tataattaat ccccaggcat ttacggccag agcagccggc caaatccgtg aagtgcagtg   16200
gttgttttaa attatattaa cttcttggaa acttatttta gggagagaaa actcagtact   16260
tctctctatc caatcttgag taaaaatgtt agaagggact ggtggagagc ctcccagaca   16320
tccctacaca tagactttgg gttgacatta tctcttttgca ccttccttga aactttcttc   16380
taaattaggt gccttcccta atttaggcac cttcccagta ctagtctgtg acctgttagg   16440
aaccaggcca cacagcagga gttgagtggc agggagtgag cattattgcc tgagctccgc   16500
ctcctgtcag atcagcagtg gcattagatt ctcatagcag tccgaatact attgtgaact   16560
gtgcgtgtaa gggatctagc ttgtgcattc cttatgagaa tctaatgccc gatggtctga   16620
gatggaagag tttcatacca aaaccacccc ttcccctgc caccatctgg ggaaatattg     16680
tctaccacga aactgatccc tggtgccaaa aaggttgggg accgctgtcc taagggatct   16740 gcttttctg acctgaggtt tttctttatt agactgtatc tggctgagga aagcctgaa    16800 gcctttaatc ggaacagctt tggctgatga gattagattc agaaaccaac agattggtct   16860
tttctatgca gggaagccta ggaactgggg ggctatggct gggaagcccc ctattgtttc   16920
catcctttcc tatgttcatc ctggaggaat ggcatcagac ccatgcctct gtgattgctc   16980
ccagcccatc caaccacagc atctatgttc tgcctgggac cagggccagg agcatggca    17040 cactgagctg agtataagga gagtggagca ggccactgcc agcccagaaa attttggtca   17100
aagttgcctg aaatcttctc agccttcgat tcacagctgc tctctgctgc tctggggcca   17160
tgcagaccag ttcagaaaag agttaatttg ttggggcagt tggaggcagg tggactgcca   17220
gctttgacac cttcccagcc cacaggctgc tgcactgggg ctgaaggcgt ggctaacccc   17280
```

```
tgcacaccta gagagtgaca gagatgccag actgggcagc aggaaggcaa gaggattaag    17340
agagagcttc ctggctgaaa gccacactcg gttaaccagg aaaaagccct tggcacgaga    17400
agactcagtg gcctgaggga ctgagccttg gttgttgggc atgtgctgca taagccatcc    17460
atgtgtgaca gtagagtgta gtccagccac tgtgggacat gggtgctgaa agaccacatg    17520
gagaggaaca gtgagtgctg acaagggcta gccttgatca ctttggagac accccctgtg    17580
tcttctagat gtcagacttt ccaaatctgt ctgctatcct ccaaacgtgc attttcaaga    17640
gcaatggaaa aaggattgga cttgatggaa tgcagcaaga gtcctaggtc tgttactacc    17700
tacctatgac cttaagaaac tccttcaccc ctcagaaccc ttacagcttt ctttctgatt    17760
ctatcctgag ttactctact ccaagctgag acttttctgc ttagatctat cccttcctcc    17820
taaaccccca acctccattt ctcctggtgt ctttctttac acacccctca gcatacacac    17880
acacctagcc acaggaacca atgagttaat atttgaggag ttggttttct tttgtcctca    17940
atgagatcct ggtgaggcca cttgagctgt tcagctccct tgcggtattt tggggatgga    18000
actcagaagc caacaatata gaaaaagagt ctttggccag ctttcccagg ggctccatgc    18060
catagagagt actgcacccg tgtgcacagg gggccctgac atgaggactt tgaggataac    18120
actattcctc caactctgct tcagcatctc catggatttt cacacagaca ctttaggaaa    18180
gaaactaagt ttgggggggac ttgacctaat cccacatcac agcccagta atacagccct    18240 ggaatttatc acagaaagcc tagaatccca tgcatatccc atgcatatgc atccctagtc    18300
ctatgggttc aaggcttgga gctctccctg gatttagctg ggaaaagttg gcagacagtt    18360
cttctctgtc ttctagaaat atggactaga atcgtgagtg tgagattgca agtaactttt    18420
aaaatcatct agtttaactt caccccattt catagaccaa gaaactgaga ccagagagag    18480
aaatggactt tcaagttcac cctgctagtt actgatggat cacaagtcaa atctcctgat    18540
tctagcactg tttctcttac accacaccac ctttgaaagt gtgtcaatca aatcttactt    18600
tagttgcaga ggatgacttt agtttctgaa gataaaattg tgagtcaatc aagatgagtc    18660
ccaagacaat agcctgttta gcccttataa gttcagggat gaaaggttag aaagaaacag    18720 gatgaagga ggactggaga aaaaaacaaa agaggaagga aggaggagga agcaaacagg    18780
aaaaaaaaag aatgtgcata gcttgtcact cctcagtcat ttcctgggag cccatttcta    18840
gcaaagtgac agctgcaact ccctggccac ctgagcatct tagctgatct gtctctgaaa    18900 cacccctgg agaacagatg aatcaggctt catcttcgct taactaagtc ttccctgaga    18960
cgactccatt taaatgaaca agagcaggat ttcctgggca cactgagagc accttccaga    19020
ggcccctcca gagccctaaa gcctgtattt cttccagtcg gcctgtttct ttcctggtga    19080
tgtcattaaa cgcccttga gagtcccaca gtgagcagtt ctgcggtaaa acccgctgca    19140
attaaagtct gagtcctttc ctgtctcaaa gggcatattc atatagaaga aggaaaagg    19200 aaggactggc tgtttgcatt tggttccagg cctgttgagt agaggtcgtg ctcactccac    19260
cgaaggtaca gggtagcctt cagcagaacc tggggatttg gttttaagca agtctttctt    19320
aggtgtgggc tttcagaaca cttccttcct tgcaatatta tttgaaattc tcagtgtttt    19380
agccgtcccc agaatattgg ttcgttaaag ctgtgtattt cagatctcca gacagtggtc    19440
actgtttgta tattttcaat ttcaaaccag aaaacaaaag ttcttattga ttactttttt    19500
tatttaaaaa ataaaagta agtatcttcg taagaggagc tttgttttaa ttttaaagtt    19560
taaaatttga ttgtgaagac agagaaaaac ttgatgattg tagatatatt cccctctttg    19620
```

```
gctattcaat cagagaacta gaaaatcatg agagatttaa tgaccactgc ctgatacaca   19680
tatgtgtttt acagatgagg aaactgagac ccagagagat gatgaaattg gctgaggatg   19740
gcccagctgg tcagtgaaag actcagagcc agagctggtg cagggctctt tctattcctt   19800
cctgttccct ttcaggaaca ctcaccatcg gctttcctgt gaataatgtt gagataaaat   19860
ccttggtgca ttatgttttc tagtcacaac attgactagg ctgccagagt cctctgttct   19920
cccagttggt tggctgtagg tgttggcagc cgccaggagc attctacaga acagaggagg   19980
agtgagactc tccttgctca ggaaaggcag acctatgact tagcaaataa ctcctaagag   20040
gagagtgttt cacccaccat tcctcttcct tggctgtgga ggcaacttag tggagagggg   20100
ccagatgacc tgtgaggaac agtgaagccc tgcctaacac aatgtatggt tgtcttgtta   20160
cagagtcatc agctacgagt gctgtcctgg atatgaaaag gtccctgggg agaagggctg   20220
tccagcaggt gaatgaatcc tccgggcctt gcctgttggt gtgggtggaa gggaatggtg   20280
ggagagagga gtacccacat aaaaggcagc agagtgtgaa tgggggcagt ggcacaagga   20340
catggcattc tccccacgtg cccactggcc ccaggctcta tgcgaggggc tgaggaatgg   20400
aagctggaaa cagcgcattt cctgagctgc tcctcctggc ctccttacca cactggtgga   20460
gtagactcca actgtggcct gtccatgccc ttcccagcag gcacaggctc aggctcaggc   20520
tcttggcctc tgcctctggc tgggagtgat tctaaacaca tccagcaggg tcagcctgat   20580
agcccatcag tttccgatca gctctgctag agagccgatg gatgtggga ggaggggtc    20640 actggtgggc tggcaacccc aagccatccc catctccctc tgtgtctaaa cttggcccctt  20700 tggagttcgg tagggagaag agccataggc caggtgggct cacccagagt cagcagagag   20760
tcccacaaat ggttgcactg ggcgaaagac agcatggcac ctgtgaattt tattagagct   20820 tttctttta tgctacacac aagtgactgt acaggggagt tagtattttg ttttaatttt   20880
gaaatagagt catcttttgg tatctgcggg ggattgattc taggacccat tctaggatgc   20940
catatcctca gatgttcaag tccctgatat aaagtggtat agtatttgca tgtaatctat   21000
gcatattctt ccatgtactt taaatcatct caagattact tataatacca aatataatgt   21060
aaatcctatg taagtagttg ttatacccctc ttttaaattt ttgtattatc ttttattgta   21120
tttcaaaaaa tatttttggt ccatgtttag ttgaatctgt gggtgaagaa cccacagata   21180
cgaagggcca actgtattgg ctatttttt agttaagaat gtgagactga ggccaggcgc   21240
agtggctcat gcctttgatt ccagcacttt gggaggccaa gagggacga tcacctgagc   21300 caagaattcg agaccagcag cccgtgcaac atagtgagac cttgtctctt aaagattgtg   21360
agactgggct gggcacggtg gctcacgcct gtaatcctag cactttggga ggccaaggca   21420
ggtggatcaa ctgaggtcag gagtttgaga tcagcctggc taacatagtg aaactctgtc   21480
tctactaaaa atacaaaaaa attagctggg tgtggtggtg ggcgcctata atcccagcta   21540
ctcaggaggc tgaggcagga gaatcgcttg tatccaggag gcggaggttg cagtgagctg   21600
agatagggcc gttgcactcc agcctgggca agaagagcaa aactccatct caaaaataaa   21660
taaataaata aataaataaa tcatgagact gagacataac aggaaggagg gcaatttggt   21720
tggttccaag gttcctagag tatgtgatgg gagaggttgg tgcgggtggg gccatggagg   21780
tactgactca agtggaggga caggtgggga aatgggatgg gaaaagaaga ttgaccttag   21840
aaggggagct caacctctga accctaattt cagaccttc aaaatgaata ttaagctcat   21900
tttggtctaa gaaacaaaaa acaaatgaac atgaaactca ttttggtctt ataaggtctg   21960
agaaacccct tctaaacttc aagctgcttt aagaaataac attttattac ctgcaaatac   22020
```

```
acacagtact ttggagattt ataatagtct cttattctaa tagaagccat tagggaacca   22080
gtttcaataa acaggtaaat ctgtaagact agtttgtaat taggatatct gtttccagtg   22140
tccattcctg cctctgttat ctaaatgtct gggaacaaga gctgtgctct gctgtgttta   22200
aaatgattaa aaatcaccaa ttagttgagt tcacgtagac aggcatttga cttattgagt   22260
tgttttaaga agactataac aagccttaag ccccccagaa acagcctgtc tttgggcttt   22320
cccacatgcc tcctcgtcct ctccacctgt agatgtaccg tgctctctgt cagagaaggg   22380
agggtgtggt tgggctggac cccagaggc catccctcct tctgtcttct gctcctgcag    22440
ccctaccact ctcaaacctt tacgagaccc tgggagtcgt tggatccacc accactcagc   22500
tgtacacgga ccgcacggag aagctgaggc ctgagatgga ggggcccggc agcttcacca   22560
tcttcgcccc tagcaacgag gcctgggcct ccttgccagc tgtgagatga cctccgtctg   22620
cccgggggac tcttatgggg aactgcctta cttccccgag gggtgggcat gatgaatggg   22680
agtctgcagt catttcctac tgtttcagga agctttctcc ttaacccctt agaaaaggct   22740
gtggaacttg agctaaaata tgtcttacca ggttgcgtct aatgcccccc gttccctact   22800
gggcagaaag acttgggtgc ttcctgagga gggatccttg gcagaagaga ggcctgggct   22860
cacgagggct gagaacatgt ttcccagagt tgcaaggacc catctcttaa acacagagtc   22920
tgcagcccct aactgacacc ctgtccttcc tcctaggaag tgctggactc cctggtcagc   22980
aatgtcaaca ttgagctgct caatgccctc cgctaccata tggtgggcag gcgagtcctg   23040
actgatgagc tgaaacacgg catgaccctc acctctatgt accagaattc caacatccag   23100
atccaccact atcctaatgg ggtaggggat ccccagccat actgcatggc ccttggtgca   23160
taatgaaccc atttctgttc catgtgtggg ctggtttctg gggtttaagc tgtagacaac   23220
ccaccctctt tgtgcctgct tctccttggg ccctctattc cacagcttgt ggaacccaca   23280
ttttgctact gtgtttgaaa acactgttt cctctcccgg ggctttggga ctatgcctct    23340
gttgtgttga ctgctcatcc ttgctgcttc tctgggcaga ttgtaactgt gaactgtgcc   23400
cggctgctga aagccgacca ccatgcaacc aacggggtgg tgcacctcat cgataaggtc   23460
atctccacca tcaccaacaa catccagcag atcattgaga tcgaggacac ctttgagacc   23520
cttcgggtaa gggactgccc tgggtggagg cccaggcttg ggacacattg cctcccaaga   23580
ggggcctagc aggaactctt ctgcaggaga ggtagaggat ggctcctgta ggggaacata   23640
gagcaggttc ccctgaatgc ccttgaacat ggagaattca ttgaccagac attcagcttg   23700
acctaacctg tgaaattctc catcttcttt ataaagtgtt cccttccttg cctccctgg    23760 aaaggtcagt ggtgtgtggc tgcagcagca cagtgtcctc tgagccctgg acctgcactg   23820
tggcttccag aggtggcagt tcccacatgg ggtactagaa taaatggcct atcaggctgt   23880
gtgtgctttg ggatcacatg tccccaccct aggaccctgg ttccaaccat acgcatgttc   23940
tcttggagcc cagaacagca gagaagccac cagtgtggac acagaagtca agggtctgat   24000
ttccagcctg gcttctgact gctctggggc cgcaggaata cggttccttc ccccatgccc   24060
agcaggcatt tgtcttacaa ctggagggga aggcatgttc ctcttggcaa ggactgctca   24120
ggaggaagtg gaggcaggct gccctgtcag ggttttttgcc ttgattcaag gagaacttcc   24180
taaccacaaa ggatacaagt gggagtgagg cggaccctcc ctagagatct ccaacacaga   24240
gagacaaaca cgctggggct ggctggcact gacaggcctc gcaggtgtgg atggctgtta   24300
gctgggagct tcgctgtcta agctcctctc ccatgctttt cttctgggtt gctcgaagga   24360
```

```
cggggggtctg caagaaaatg atgttcccac atagttggca gcacgtgaac agcaattgat    24420
ccctttgcat cacctcctct tactgtttag atttggtaaa tatttcttcc ttccctcttc    24480
tgaccctcca ttttgccgat cttttccttct tataacacat acttactagg tacctgctac    24540
ttcccgggtg ggcctatgtg ccaggagtat agaggtgaac aaggaaggca aagttctatt    24600
ctcagtagag ctaatactct atctggagag agacaacaaa caaatcaaca aggtagccag    24660
gggctgtgat aatttatgtc aagtgggcag gtaaatcggg agtgacagta gtgcaggag    24720 gattggaaag tcagggagtt ctctctggag gaggtggctt ttgatctgca gcctaaagga    24780
tgagaatggg tccattatac aaaatgctgg ggcaagagca cacccagtag aggggagagt    24840
aatagcaaag gctcagggca ggaagggcaa gggagaggcc agtgggtgag gtcacatgtg    24900
aagggcatac aatgggcaaa gacaaggcca gagtggccag gcccaatcct ccaggacttg    24960
cagacctggg aaagagtgca tctccatcct gggagcagca ggaaaccact caggccttta    25020
gaagatcctt ctggcagctg tgtagagaat gggtggtgtg atccttccat gcatgggctc    25080
atgtacgtga ttaccagtaa ctgtcgagtg acagtgtgag gagggctgca agccatgagt    25140
gtaggcacag cagacagact cacctttgtc tggcggtgag atggggtggg aagtgtgcca    25200
agttgacctc ccaaagaaat gatatttag tggaagaatg aatagaatca gagaagcaaa    25260
gtaagaggga agagcagaga ggacagcagg gacaaggact tgggggcagg aagaggaaag    25320
gcaggttaag gacatgaaag atggccaggc tggctggagc tcaggcccag caaggccccc    25380
tgggggccat ggtcatgggt gagcttgggt ttggcttctg ttttcgtctt gggcttctgt    25440
gaaagcctcg agcccttgcg gggaaccagt gaagctgtgt gtgcatcttc tgtggggagt    25500
gccagagtct tcaggagca ctccatcttc tctcctcccc acaggctgct gtggctgcat    25560
cagggctcaa cacgatgctt gaaggtaacg gccagtacac gcttttggcc ccgaccaatg    25620
aggccttcga gaagatccct agtgagactt tgaaccgtat cctgggcgac ccagaagccc    25680
tgagaggtga gcatccttg gctcctgctg ctgcctcatt tgtgcagcta gattgagccc    25740
aagacctgct ctggtccaag atgaacatac cacctgccat gaggtgaccc tcaggatatc    25800
cactgcagcc atgggctggg gtcatcctgt cctgttgctt cagctaaccg tgtctctagc    25860
agccacacta ctctgagggc tgactacaga atccagcagc ttttgtctgg gagagctgga    25920
ctgaagagag gcatagctgg agacccatag ctggccctgg ccagaaacag ggagagtgaa    25980
aggctggaat agccaaggcc agagcaaggc taataggtag agcaacagct tacaggtgtg    26040
ggggtggcag atactggcac ccttgaaatg gattcctcat gcccacgctt cactattctt    26100
ctctgtggct agggattta tggataaacc aaaattacag ttaaaaacca gccataggcc    26160
aggcacagtg actcacgcct ttaatatcag cactttggga ggacaaggtg ggcggatcac    26220
ctgagatctg gaatttgaga ccagcctggc caacatggcg aaaccccatc tctactaaaa    26280
atacaaaaat tagctgggca tggtggtggg cacctgtaat cccagttact caggggctga    26340
ggcaggagaa ccacttgaac ccaggaggtg gaggttgcag tgagccaagc ttgcaccact    26400
gcactccagc ctgggtgaca cagcgacact ccgtctcaag aaaaaaaaa aaaaaacag    26460 ttatagtagt caacttttga ctctccattt cagatttcgt catgccctcc tcaatgagct    26520
gctaagttag gcagtgcatt gattattgct gcaggagagg aaggaagga gctaacgtgt    26580 tttcacatgt tttcctttg gagatgagaa aggaggactc tgccttcccc ctaccctgcc    26640
cctttctact ccaggacctc tgaaaggcca tgagcacaaa gctgctgcct gagtcccctg    26700
aaatgcaggg tacgccccag gtctctgatg taccccacca cactttcct ctcaaacata    26760
```

```
ttccaggatc acttgatttc ttttgaatct atttaaaccc accgtgtcaa tgtgctatat    26820
aaaatgtcta atgcatttca gacaccctat acatctatac atttaaagtg ttctccttct    26880
atctgtgcag ggatgggaaa gggcatattt ctgaaagcac agatgggaag acgggatttg    26940
ttccgtgtcc aggtgattat ggtacctcta tgcgcctggc cggcactggg gacagaggcc    27000
atgaaaatga atacagcaca gcctttgcct ccaagaaact taagacctag tagaaatggc    27060
aggctttaaa acaggttgtt gggatctgat ttggtgagtg caatgacaga gatactcaca    27120
gcacaaaatg gggaatgagg gcgggcattg ggacacacat agccttaagg ggcccaaagg    27180
cttttagaac tgtattccct attaaaacat gatttgcaca gagcacattc tttgctttgg    27240
agacctcaga actccttact ataggccggg catggttata atcccagcac tttgggaagc    27300
caaggcgggc agatcacttg aggctgagag ttcaagacca gcctggccaa catggtaaaa    27360
ccccgtctct actaaaaata caaaaattag ctgggtgtgg tggtggccac ctgtaatccc    27420
agctactcag gaggctgagg taggagaatc acttgaacct gggaggcaga agttgcaata    27480
agcccagatc atgccactgc actccagcct gggcaacaaa gctagactct ctcaaaagaa    27540
aaaaacaaaa caaaacaaaa caaaacaaaa aaaactcctt attataaact gtaagaaaaa    27600
aaaggcccct acttcgtccc ttttgcaaat ctgccttttc ctactcacta accagctggt    27660
tcagagcaag gacactctgt ttggtgccat cgctgcagac tggaaggaag aggtccttgc    27720
cccacaccca acagtctcct gctgttaccg gcaggttggc aggcaggcag gcgagaagca    27780
gccagggctg gtggtgtgtc cagtttgaag actagtttcc agccctggcc ctgctcaccc    27840
tccaagtggc cctggcaggt tcctctacca catcgtggac ttcaccttcc ttctctaaga    27900
agctcaatcc ccaaggcctc attcccatag gccttctcac ccttttttctt tccctctggc    27960 tgaatgtggc cagcacgggc ttccaaggcc atcaactcgt ctgcagcagc cccatgcctt    28020
gcagggcctc agagcttcct cctgcctatg acagtgtggt tttggttccc acacttggga    28080
tcagattgaa actcgcctcc gtggtgagaa tatgggacat agagcctcgg tgaccttggt    28140
gagcagcagt ccaggccacc tgctcagcct ggggttgggg ggggctcctc ctccttgact    28200
ggtccttgca tttgcctcca tccagcctgt ctgggctctc cgaggcaatg gagaccagca    28260
ggagtcacga tgggtcagga gccccctttg ggcctcagcc ctgccctgcc ccctaaagta    28320
gcacttggat aagcaaataa attattatac ttactattta tgggtgtggt gaatgggatg    28380
gcaaaggcca agtcttactg atcaccaaac cttaagatat atcctggcag ctagtagacc    28440
cttgggctaa atgaacagaa aactggacaa ataaagtgta cacaaataac tcaaagctgt    28500
catttgtaca cttttcgtct tttcctacta cagtttacat ttttataaag gtgagtagat    28560
ttctaaaatc ccgtggtagg ctctcttgag tttttcttgt atccctgaag ttcagctaca    28620
aataagctaa tcactaacat tgttgagca tttactctgt tgtcaggccc cgtgccgagt    28680
gctttaggtt cagaatttca tgtcatcccc acagcagccc taggagatga atgcaattct    28740
tatgtccact tgactgataa ggaagttgag gttcaaagag gctaaatgac tctcccaggg    28800
tcccacagct ggaaagtggc cacagggccc cagctggttt tctagggcag caggcagaag    28860
gcgaggagga tctgggccct gtggtgcccc agcctcatct gagggtcctc atctgagaga    28920
acaggatcct cacagcatgg gcaggctgca agtggtccct gaggttatcg tggagtggac    28980
cctgacttga cctgagtctg tttgaccccc agacctgctg aacaaccaca tcttgaagtc    29040
agctatgtgt gctgaagcca tcgttgcggg gctgtctgta gagaccctgg agggcacgac    29100
```

```
actggaggtg ggctgcagcg gggacatgct cactatcaac gggaaggcga tcatctccaa   29160
taaagacatc ctagccacca acggggtgat ccactacatt gatgagctac tcatcccaga   29220
ctcaggtagg ccaggcctcc gggggccttg ccctgcctg gccaccatc tcttctgcca    29280 tcctttgtgg cggggagggg gaaattcaga gatctttggg cgacttccct gcctggaccc   29340
agctcacagc ttctcggcca ctgcaaatgt gtgggttgtg accagactga tgtgtcttga   29400
gcttcaggct tgcaagtgca gtggagaggc agtgggagc tattgaaggg gtctggggac    29460
agactcaatc acagaggcct ttcagaagat ctgcctgctg tgcatgggca agagggcca    29520 cttgctgacc tcagagcatg tgcttctca gtagtgccca agctgtccca tggtcactga    29580
cccagttaga atgactgaat ggactttggc ttgtgtctca ttaggaatcc tagccccatt   29640
ctagtcttcc agtgagatct gtccatgagt gaaggaatct cacaggaaaa aacaaaatgc   29700
ttctatgggt gtggttgctg gccttatcta caccacagaa gccatcacac agactgtctt   29760
tcttcccatt gttagaatgt gccctgacca agcagcccac agggcctggg acagaggctg   29820
atctctgcct aactgagctc acctctcctc cctctcctcc tgactggtta gattttctag   29880
gtgactgttc ccctgatgac acaagcccgc tgggccccag cagtgtttag aggggttgtt   29940
gactcacgag atgacattcc tgctgatgtg tgtcatgccc tggggtggat gaatgataaa   30000
tgaaaacagc gcttttaact tttgaaccca cttctccttt ccttgtagcc aagacactat   30060
ttgaattggc tgcagagtct gatgtgtcca cagccattga ccttttcaga caagccggcc   30120
tcggcaatca tctctctgga agtgagcggt tgaccctcct ggctcccctg aattctgtat   30180 tcaaggtaa catggggaag gcatcccctgt tagattgtcc ctggaggcag cttccccacc    30240
cctgtcacct ccacaacact ctccgattta cagcaccca tgggacatta gaacttccac     30300
tcagctcaac caaaagcaga tgtgacttca gcagaaactt cagaggctct gttgtttcat   30360
taggcagtgc agagaatgcc tttggggagc cgttcctcag aactcaagac ttgacatctg   30420
ggaggcagcc gttcctcaga actcaagact tgacatctgg gagagcagag cattcccttg   30480
cctttctatt tgcagggtca cttgccaatg tatagtcaag aggtcagagt gagggtacag   30540
ctgagctgca gccccaggaa ggcagagaag ggggccaagt tgtgtgcgtg cctgcccttc   30600
cctcttaggg caaaactcca aacacccttg attatctgga tcttctttaa ttctccatag   30660
aagataccag atgttaagga atattggcag cttcacttgg tttctcaatc cctgtttcca   30720
aactcaagga gggatgggct ttttcactgt atttatctct catcactctc ttcattgcag   30780
gagcacatct ctctggacct aaccatcacc ctttcttgta gatggaaccc ctccaattga   30840
tgcccataca aggaatttgc ttcggaacca cataattaaa gaccagctgg cctctaagta   30900
tctgtaccat ggacagaccc tggaaactct gggcggcaaa aaactgagag ttttttgttta   30960 tcgtaatgta agttctgggt cctaaatcat gctcctggga agctccttac tgtgggactt   31020
gtattagtgt aaaaaaaaat gtcctcaata agcaggagtt tgcatgagaa ctggttgctg    31080
acaaggaagg aaataatttc tggaaaatat agataacaaa atgagatcct gcagaaggat   31140
tggaatctct ttttctggag gcctttgaga ataaaccaca caattatcca acctgtattg    31200
tgaaggaata agtccttctt gaattcagga attaacacct gggaggaggg atggagttca    31260
gactctttct gagcttatga aagagaagc cccctaaact aaaatacagc cctccttggt     31320
ccaaaaggtg ccttctctct tctgctgtat cttctttgtt ttcaaaccca acagttaccc   31380
tggaaatcaa aaaggaagta caactcaaca tagctcttgc ctgggaccaa ccagcaccat   31440
ttggctaaag atggttatca tctgttaaac aaagaaataa ataaatgggt tcaacgtatt   31500
```

```
tatttcaaca ttgtcaatgg acctcatgtg taactgatat tctcattatg ggacctctgt  31560
gtgactttat tggggcctct ctaaccgttc tttccttaag gaagaccatt tattgtttta  31620
tttcctggag aaaatacatc attttatccc agccttaata acccatccca gtgtatactc  31680
cttcatcttc atggataatg accctgctac atgtctgaa caaatcagga ggcccctcgt  31740
ggaagtataa ccagtccttt cttctctgt ccctcttctg tgcagagcct ctgcattgag  31800
aacagctgca tcgcggccca cgacaagagg gggaggtacg ggaccctgtt cacgatggac  31860
cgggtgctga ccccccaat ggggactgtc atggatgtcc tgaagggaga caatcgcttt  31920
aggtaattag ttccatcccc gggtggagct tctgcccagt ggtcatgctg gagtgggatg  31980
tggggcccca gctatttgtc aagctttctt ctaccttggg gattcaatta acactagcag  32040
tgcactgctg cgaccttcca gacttgggat ggggaaaagg caagggtcgc cttgaaagct  32100
tacattggga agaagggtta cttctaagag tgtaatcttc acatgcatgg gaagcaggga  32160 gggggggacta cattttatg actgaagtgc aaggaaaaca tcaccctctc attgtaaagc  32220
tccaagtgag ccaagagcac atagtttaca gtgcacgatg agcctctcac tctctgcgca  32280
gtatctgttt attgcaactg aagcacccctt gtgagtttgt tttcttgccc ggctatctcc  32340
atttctgact tgctcattca ccttggggtg ctgtcatatt gaatgtttcc ctgtcactga  32400
cttcagccac ctgcacaagg gcttggagac cacacccctc tgccctccca gaatcatatc  32460
cctggaggct cagctagtct ctgggtcagc catacctctg ccctttcttt tccctccttt  32520
ctcctgtggc ctctgacgtc tggccatta acagagctta gcattttgc tgggtggaga  32580 gagctggagc ctggaatcac tccctctttg tgcatacgga gggcatgaaa accaaggtgt  32640
gtgcattcca gtggcctgga ctctactatc ctcagtggtg aggtatttaa ggaaaatacc  32700
tctcagcgtg gtgaggtatt taaggaaaat acctgttgac aggtgacatt ttctgtgtgt  32760
gtatctacag catgctggta gctgccatcc agtctgcagg actgacggag accctcaacc  32820
gggaaggagt ctacacagtc tttgctccca caaatgaagc cttccgagcc ctgccaccaa  32880
gagaacggag cagactcttg ggtaaagacc aacttaagta cacgtctcca tttttctaaa  32940
gtagtgatcc ctcagggccc cagcagcaaa cagttggcac atcaaggatt gacttgaagg  33000
gattttatga caagactatt agtgaaagag tgggcgggac taaaggaact agcaaaggat  33060
gaggccaacc agggactagc aaccctggga agcctttact accccctaggc ctgggggaat  33120 gggaggatga gagcaggaac cagggaggtc atgagccttg acaagggca cagaacagca  33180 gccagagcca tgtgcagcca gccactgtca gaaccatgca agggggacca ctcagcgccc  33240
cagcctccct ctcagacagt tgccatctgg gtctcttgtt ggctgatgcg agagcaggag  33300
ggagcccact gatgcagttc atagagctca gcctcctggg caggaaaccg ggcagagagg  33360
agtagaaaag aattaagggt ggctgcgacc agcccagtca ctgaggcacg tttcccactg  33420
gagacctatg agcacagtga taataaagcc agttacctgc actgactatc cctccagaca  33480
aaagctttcc caagaagtta gtcatggctc tgagagatct agttgaggat gtttggcagg  33540
ggatctagtg gttacggtg gctaagaaaa atgaggaagg taagagtatc ttgcagcctg  33600
tgttgggagg attaaatagg atgccacaca cagggccagg cagacagcct ggtcagtaat  33660
agccatgacg atggggcgg ggggagcagg aatgggagtt gcagtgttta gctcagatgc  33720
atgcctgtga gagatgcttc cactctcaca gaaagatgag accaaggaaa aggaggagga  33780
agaggaagga ccttgacaaa ccttgggggcc cacattgtct cacctcccct tcctgctcta  33840
```

```
gagcagaata gaaagttcag gttgcaggca gctctaagtt gaattcgtgt cctgtttaat    33900
tttctttatt gctaaatgaa tgcctgtgtc tgtgatgctg acgtatgttc ctaaggagag    33960
gggagaagtt cattctgaac ataaactttt catcctctct ctgtccagca agaatggaat    34020
attccccaag tggcctgagc cagcttggct ttcttttttgt tttcaattat gtgggagttg    34080
aggaggggga tgggaaaagc ttcccaaaca caccctcccc caggcctgag gcacccctgg    34140
gggacagaga gtgttagagg ttggtacagg tgttagagat attgaaagga catcccatgc    34200
accccagggg ctggtgtggc tctgtacttc caggcaatat tttgtggaag gggaaccttg    34260
tcagctccag gttgtggatg tttgaaaatc agttggtacc cagtggctcc atcctctggc    34320
aggcatgtgg atttgtcaat aaccaagtga actctccaaa ataagttaaa acttcctccc    34380
ttctcagttt caagatgctg gaaatagctg ttcataagcc ctggggaaat ttagcccttt    34440
ggctggtaat gggagtatcc gagatgagag ggcagctgga aactttcgga atgacctccc    34500
acacttaatt tgggaaatgc ctctgcacct ttatgggcaa ccagatgcct gccccagttg    34560
ctggagacac tgatgtgggc tgaaaggaat gctgagacgt gacgaggaga gatgctgcgg    34620
agggaatatc cccctcagcc ctgacctcat cggctccatg gctcctccac agtacagctg    34680
tctactcttt taagttctcc cttcaggaaa tagccatctc aaacagaatg tgcatttgag    34740
ggcagaatgt gtaaatattg cactactgtg ttataaccgt caggagccat gctgatgatg    34800
aaacgtccca gatgccggtg ctggaaaggt ccctggcttt ccaagcaaat atttatctca    34860
tggaaacatg agtcatactc acagaggagt atggattaac tccttctcag cagccaggga    34920
gcccagcatc ccagacagca tatttaaccc agaggccaac tgactgctgg ggcagatttg    34980
tggtcatgaa catgtgcttt gtgtcctctg accattagac agattgtggg tcacaacgtt    35040
gagtatacag tgggagctta ataagtgctt attccctggg cagggagttc ttcatttcag    35100
gggtgaccac ttacatcttc tcctctgggc cctccttgac caggctaatt accattcttg    35160
ggattaactc tatctccttt tcccgcaacc tgcaggagat gccaaggaac ttgccaacat    35220
cctgaaatac cacattggtg atgaaatcct ggttagcgga ggcatcgggg ccctggtgcg    35280
gctaaagtct ctccaaggtg acaagctgga agtcagcttg gtaagtgtcc tgcaaatcaa    35340
aggctggcta aatttcccca gggcagggct ccaggacata tctcacccccc aggatggaat    35400 tatacacaca caaccttcaa gttgcagccc gaatctctga gtgtaattcg tccaaagaaa    35460
aagagaaaag agaagagggt cttcagggaa atcaagtgag atcatagtta gacatgagta    35520
agaacttcca gatttacaag ggaatagagc atctgatttg gcatctgaga gaggctatta    35580
gatcttcctt ctcttaagga ggttgtaggc aactagttat gtgactgaag agatcagtct    35640
gtactcacac catcccaccc cccaaaccca gggcttcact gagttgtacc atgaaccaga    35700
ccatcccaag aggctttttg agttctgaca cttgctctgt gagccttccc ttgctctgca    35760
cattgatgat ataactttgt aactgcacta agagtgttcc taaagcagat agccagccga    35820
gctccagaaa tctccctggc tgcacctgca gaggccactg accctctgt ggagggaccg    35880 ctcttcagtg tgtggctggc ttctactctc tgctcctctc tcttggtctt cagccatcca    35940
ttgctcacca gtttctcacg aggagcatag gaagatatgc atgtagggag gtaggcacgg    36000
ggatgacttg tttgacttta gcaggtcatt caagaatctc ctcgcacctg gtttcagatg    36060
ctggggtcct gtctgtcaca ggcttctgtg cctcctaccc ccttgagttt gtcacatggc    36120
ccttcaggaa ggcctgagat agatttgccc tgggtgggcc tcctatgaga aaatcttaag    36180
tgaggcaccc aggcaaaatg gaaagagcct tttgcccaga gcaggaagcc tgtcttccat    36240
```

```
ttccagctgt tccacctact tagcttaaaa gaggcacttc gcctgtcttc agtctcagtc   36300
tcagtctcct cttctgtgga atgggacaat aatatctact ctccttatca tacactgctg   36360
tgaggactga gtggatcaca caaaaaagca ttatgtaaat tgcaaagtgc taaatccaca   36420
caggagattt gaattaatcc accacactga aggtctgtca agggcaggga ctgtttcatt   36480
caccagagta tccccagtct aacacaggac ttggcatatg aaaagtgttc agtaggccgg   36540
gtgcagtggc tcatgcctgt aatcccagca ctttgggagg ccaaagtggg cggatcatct   36600
gaggtcagga gttcaagtcc agcctggcca acgtggtgaa accacatctc tactaaaaat   36660
acaaaattag ctgggcgtgg tggcacatgc ctgtaatcac agctactctg gaggctgagg   36720
caggagaatc acttgaaccc aggaggcgga ggttgcagtg agtcgagatc atgccactgc   36780
actccagcct gggcgacaag attgaaactc catctcaaaa acaagaaca aggaaaaaaa    36840 cgaaaactgt tcagtaaaca cttgctgaat gaataaaata aatatataaa tgtataaata   36900
aatgctctac tttcaaccac tactctgttt ttcttttaga aaacaatgt ggtgagtgtc    36960 aacaaggagc ctgttgccga gcctgacatc atggccacaa atggcgtggt ccatgtcatc   37020
accaatgttc tgcagcctcc aggtaagtgt cgcatcccca ctgactctgc agccagtcct   37080
tttcttcatg tggcagttgg tggagagaag aaaaactgtt ctaaacaatg atgagaataa   37140
catgtaattg tgatagttaa actgtgccta tgtgactgat tgcagagtga attgggagct   37200
gttggttttg aatgcaccac actaaggaat gtgaggacac attgctcttt gcggagttgc   37260
ccagctatat tagctcccct cggacacagc ccagttttct gtattcgcgt ggatgctgtc   37320
cgcgcgattc ccagcactcc tcttacagca tctcacctca gtgtatgttc cttgcctcca   37380
gtgcagttga acctcagtcc tgcctctcct catgtgtgca ttcacctttc ttggtgctct   37440
ctccccatgg gccaagttct accatgagtt atgaaacatt atggagaaaa catgtctttg   37500
gaaatgtgag ccagaaagcc caccagtgcc cctcagtcac ggttgttatg aatgacatgc   37560
taatggtttc actctggtca aacctgcctt ttctttcctc ttcagccaac agacctcagg   37620
aaagagggga tgaacttgca gactctgcgc ttgagatctt caaacaagca tcagcgtttt   37680
ccagggtaag atgcctgcta ggtttgcgcc tagcctgagc agcctcaggt cctctgtttg   37740
ggccatagag gagcctctcc agccctgtc ttccttggct gctccccagg gctctcttaa    37800
aacttctccc cactcccact gaggcatcct cagcccagc ctgtgtcaaa ttcagagtaa    37860
agaaccaagg caactccctg gctttcatgg gccaaagcgc aggctttcac accgaggcct   37920
ctgagcctca gatcatgggg aagtcactgc tggagagaac agacatagct ctggaagcca   37980
tctgcccaag agggcagccc atcccaagtt catcttacag tggccaggcc tgccctgagc   38040
cggggcctct gggtcactct tctgctgtcc atggcattgc ccatcctggg tgaggctggg   38100
gctctcctgg gcactgtatg tattctggat acagggatac tgggctcgct atgtgtgtgg   38160
agccatccct tccttgcccc agccccacct ccctctcaaa ccctctctgg ctctttctga   38220
gcttcctttc ctgctcccca gcttgcccag tgctcagtgc cccacttggc tcttttgcta   38280
cttcgggtca ggtggagcct cttgggaatg tgaagtgcct tacagaaaga ttgcacttca   38340
agaggagagg ctgcagggag ccatcctaaa cccagaggcc tggagcttac tgtgtcactt   38400
tacttttgta cacaggggtc tccttagtgc cctcgagaag gattcttggc cctgagcttc   38460
tactcctgag gccacctctg tgcagcccca gctccctcaa ctctaggctg tagtctcagt   38520
gggaaagcct ggcttggggg tctcctagga atgtccacct gaaggcacac ttgatagggg   38580
```

```
cttgcacaac ttatgtctgc caaggccacc tgaggaactc cctggtgcct ataagttcca   38640
ccttccccct cctcttcctc gccccagcat tttttctgag tagggtggc aatgggcaaa    38700 gccattgtca taagcagttg caggtataac tttcactaga aaacctgaca ccttgtgttt   38760
tctttcaggc ttcccagagg tctgtgcgac taggtgagtc tggtctgggt ttgaagtcat   38820
tgcagacctg tttaggcctt accccaagc aagcccaagc ctgccatctg ctgtatatag    38880
ataagaacat catggtgcag taaaagaagc ctggcctttg gagtcagaac agcagggtga   38940
cttggggtca gacccagagc accccatttc cttctctgta agatgaggat aataagagta   39000 acaaccttt  agggttaagg tgagttttca gcttaggaag tctgggaata ttgcaaaggg   39060
cttggcagga acccatggtg aggatctagt tccaagttga taggtacaga aaaccagaac   39120
atcgggcctt gagtaaagag tgaagtttca caaccacaa agcacctgct atgtgcagga    39180
gagcatggca gaaggaggct gcttggccct ggtccttgag attctgacag tgtcctagac   39240
agacatgggg agatctgcac ctatttgacg ttaccaactt ctcttttca gcccctgtct    39300 atcaaaagtt attagagagg atgaagcatt agcttgaagc actacaggag gaatgcacca   39360
cggcagctct ccgccaattt ctctcagatt tccacagaga ctgtttgaat gttttcaaaa   39420
ccaagtatca cactttaatg tacatgggcc gcaccataat gagatgtgag ccttgtgcat   39480 gtggggagg agggagagag atgtactttt taaatcatgt tcccctaaa catggctgtt     39540 aacccactgc atgcagaaac ttggatgtca ctgcctgaca ttcacttcca gagaggacct   39600
atcccaaatg tggaattgac tgcctatgcc aagtccctgg aaaaggagct tcagtattgt   39660
ggggctcata aaacatgaat caagcaatcc agcctcatgg gaagtcctgg cacagttttt   39720
gtaaagccct tgcacagctg gagaaatggc atcattataa gctatgagtt gaaatgttct   39780
gtcaaatgtg tctcacatct acacgtggct tggaggcttt tatggggccc tgtccaggta   39840
gaaaagaaat ggtatgtaga gcttagattt ccctattgtg acagagccat ggtgtgtttg   39900
taataataaa accaaagaaa catacgtcct gtgtgcatgg tacagtgtgc tgacctgagg   39960
ccgtcatgct cctccacacc tcaattctgc tctggagaag ctcagaaagg agcccgagg    40020 gatggttttg gggagattcc agcagccagc cctcagacag ccagacagct catgggggtt   40080
tgagcctgtc tttgccaaac aggttttat ttcaccctcc tccggtcctg gggtttcaag    40140
ttttcagtgt tgccttcacc ccgcacttta ttcctcttat tacttggaag taccttccct    40200
ccagcatggt gatcccctgc ctgtgtgctg gacttttgag tcctcagcac caacctgtga   40260
agtggttgcc agcataatcc cattatgcag atgaggagac caaggcccag ggaagggaga   40320
accaccagca gcacgtaaaa tagctgagct gggactggaa ctcacacctc ctgactctca   40380
gtgaccacca ctgacaacag cataagtcca ggttttccag gcccatcccc tctgtgccaa   40440
cccacattca gattccttcc ccggctcccg taatctctgg catctagaat atcctcagga   40500
ctctgagagg tgatatcatg tggttgtggt gccattgccc cctacctgtg tggcctgggg   40560
ccagtcatgt gacctcccag ggtctcctct tctgtaatag ggagatgacc gtcacatcta   40620
cttcatgggt ccatcgtgag gatgaaatga gatgatctat ataaaatgct tggtacaaca   40680
ttaggtggcc ttattttat cctgccgtct gggactgctc aggatcaatg cgccagagag    40740
cctttatttg tgtctttccc acaggtgggc tggcccactt tcctagagaa tgggacagac   40800
ctccttccca cccacacccca tctctgccaa ggctgattca ctccagcagg cggagctcat   40860
ttcacttcat ggaccaatg acccaaagat atatccccag cactactgct ggtcagtcca    40920
ctgctgctgg gaatacagca atggtagtgg cagacagagg ccctctctta aatagcttcc   40980
```

```
agtctgagga aagagagata tgacatcaat ccattaaaat cattcatcca ttggttccac    41040
aaatatttgt tgagggctac ctatgtgcac ccccatgtta gaccctgggg aatagacatg    41100
tcattctcat gaggcttctc tactgatggg ggggaagaga attgtcaacc agataatggc    41160
actacagcct gtgtgttctt agtgactctg aggatagcac tgtggttctg tgacagataa    41220
tgaaggattt ggaagcagga atgcccagga gctcccagaa gtgggaagag atgagaggaa    41280
tggaaggaac ttacctgaag gtgaaggcat caggctaggg gaccaaggga gaaggtgtcc    41340
tgagaggtaa ggcttaacct tgggtgtgaa ttcagttccc gtcactctcc catagctctg    41400
tcctgctgtt cccacctccc ctgcagccat gcgggcttgg gcggctagtg agggccttgc    41460
tcatgctggg tatcctatgc tatgcttcac tttgagcacc taaaatacac acactgcact    41520
ttaccaagat gacctcggaa accaaagagg tgatcagcat aagttttaaa gacccttaaa    41580
tttaaagtaa aaatcactac aggatccatt ataaatgcca acactaaga tgtgtgtttc      41640 cagttctccc cttcatttgt ccctgccact ccctgccctg actttgcccc accccctagt    41700
aatgtgggct ccactctatg ctccaaactc tccctggaga gaaatcctcc ctgtggttga    41760
ggacaaggcg cagccttccc ctcccaccaa agaaggtcag attccctttt ttggttccta    41820
accatccata ccccttcttt tctcatgaag actcgggcta agcattcatt agggctgcca    41880
tctggaggat ggacccttag agctgagggg ccagcactgt gtgt                     41924
```

<210> SEQ ID NO 62
<211> LENGTH: 683
<212> TYPE: PRT
<213> ORGANISM: Homo sapiens

<400> SEQUENCE: 62

```
Met Ala Leu Phe Val Arg Leu Leu Ala Leu Ala Leu Ala Leu Ala Leu
1               5                   10                  15

Gly Pro Ala Ala Thr Leu Ala Gly Pro Ala Lys Ser Pro Tyr Gln Leu
            20                  25                  30

Val Leu Gln His Ser Arg Leu Arg Gly Arg Gln His Gly Pro Asn Val
        35                  40                  45

Cys Ala Val Gln Lys Val Ile Gly Thr Asn Arg Lys Tyr Phe Thr Asn
    50                  55                  60

Cys Lys Gln Trp Tyr Gln Arg Lys Ile Cys Gly Lys Ser Thr Val Ile
65                  70                  75                  80

Ser Tyr Glu Cys Cys Pro Gly Tyr Glu Lys Val Pro Gly Glu Lys Gly
                85                  90                  95

Cys Pro Ala Ala Leu Pro Leu Ser Asn Leu Tyr Glu Thr Leu Gly Val
            100                 105                 110

Val Gly Ser Thr Thr Thr Gln Leu Tyr Thr Asp Arg Thr Glu Lys Leu
        115                 120                 125

Arg Pro Glu Met Glu Gly Pro Gly Ser Phe Thr Ile Phe Ala Pro Ser
    130                 135                 140

Asn Glu Ala Trp Ala Ser Leu Pro Ala Glu Val Leu Asp Ser Leu Val
145                 150                 155                 160

Ser Asn Val Asn Ile Glu Leu Leu Asn Ala Leu Arg Tyr His Met Val
                165                 170                 175

Gly Arg Arg Val Leu Thr Asp Glu Leu Lys His Gly Met Thr Leu Thr
            180                 185                 190

Ser Met Tyr Gln Asn Ser Asn Ile Gln Ile His His Tyr Pro Asn Gly
        195                 200                 205
```

```
Ile Val Thr Val Asn Cys Ala Arg Leu Leu Lys Ala Asp His His Ala
    210                 215                 220

Thr Asn Gly Val Val His Leu Ile Asp Lys Val Ile Ser Thr Ile Thr
225                 230                 235                 240

Asn Asn Ile Gln Gln Ile Ile Glu Ile Glu Asp Thr Phe Glu Thr Leu
                245                 250                 255

Arg Ala Ala Val Ala Ala Ser Gly Leu Asn Thr Met Leu Glu Gly Asn
                260                 265                 270

Gly Gln Tyr Thr Leu Leu Ala Pro Thr Asn Glu Ala Phe Glu Lys Ile
            275                 280                 285

Pro Ser Glu Thr Leu Asn Arg Ile Leu Gly Asp Pro Glu Ala Leu Arg
290                 295                 300

Asp Leu Leu Asn Asn His Ile Leu Lys Ser Ala Met Cys Ala Glu Ala
305                 310                 315                 320

Ile Val Ala Gly Leu Ser Val Glu Thr Leu Glu Gly Thr Thr Leu Glu
                325                 330                 335

Val Gly Cys Ser Gly Asp Met Leu Thr Ile Asn Gly Lys Ala Ile Ile
            340                 345                 350

Ser Asn Lys Asp Ile Leu Ala Thr Asn Gly Val Ile His Tyr Ile Asp
            355                 360                 365

Glu Leu Leu Ile Pro Asp Ser Ala Lys Thr Leu Phe Glu Leu Ala Ala
    370                 375                 380

Glu Ser Asp Val Ser Thr Ala Ile Asp Leu Phe Arg Gln Ala Gly Leu
385                 390                 395                 400

Gly Asn His Leu Ser Gly Ser Glu Arg Leu Thr Leu Leu Ala Pro Leu
                405                 410                 415

Asn Ser Val Phe Lys Asp Gly Thr Pro Pro Ile Asp Ala His Thr Arg
            420                 425                 430

Asn Leu Leu Arg Asn His Ile Ile Lys Asp Gln Leu Ala Ser Lys Tyr
            435                 440                 445

Leu Tyr His Gly Gln Thr Leu Glu Thr Leu Gly Gly Lys Lys Leu Arg
    450                 455                 460

Val Phe Val Tyr Arg Asn Ser Leu Cys Ile Glu Asn Ser Cys Ile Ala
465                 470                 475                 480

Ala His Asp Lys Arg Gly Arg Tyr Gly Thr Leu Phe Thr Met Asp Arg
                485                 490                 495

Val Leu Thr Pro Pro Met Gly Thr Val Met Asp Val Leu Lys Gly Asp
            500                 505                 510

Asn Arg Phe Ser Met Leu Val Ala Ala Ile Gln Ser Ala Gly Leu Thr
            515                 520                 525

Glu Thr Leu Asn Arg Glu Gly Val Tyr Thr Val Phe Ala Pro Thr Asn
    530                 535                 540

Glu Ala Phe Arg Ala Leu Pro Pro Arg Glu Arg Ser Arg Leu Leu Gly
545                 550                 555                 560

Asp Ala Lys Glu Leu Ala Asn Ile Leu Lys Tyr His Ile Gly Asp Glu
                565                 570                 575

Ile Leu Val Ser Gly Gly Ile Gly Ala Leu Val Arg Leu Lys Ser Leu
            580                 585                 590

Gln Gly Asp Lys Leu Glu Val Ser Leu Lys Asn Asn Val Val Ser Val
    595                 600                 605

Asn Lys Glu Pro Val Ala Glu Pro Asp Ile Met Ala Thr Asn Gly Val
610                 615                 620
```

```
Val His Val Ile Thr Asn Val Leu Gln Pro Pro Ala Asn Arg Pro Gln
625             630              635             640

Glu Arg Gly Asp Glu Leu Ala Asp Ser Ala Leu Glu Ile Phe Lys Gln
            645              650             655

Ala Ser Ala Phe Ser Arg Ala Ser Gln Arg Ser Val Arg Leu Ala Pro
            660              665             670

Val Tyr Gln Lys Leu Leu Glu Arg Met Lys His
        675             680
```

METHODS FOR MULTIPLEX DETECTION OF ALLELES ASSOCIATED WITH CORNEAL DYSTROPHY

SEQUENCE LISTING SUBMISSION VIA EFS-WEB

A computer readable text file, entitled "SequenceListing.txt," created on or about Oct. 10, 2019 with a file size of about 72 kb contains the sequence listing for this application and is hereby incorporated by reference in its entirety.

FIELD OF THE APPLICATION

This application generally relates to probes for detecting or diagnosing corneal dystrophy, and methods of detecting or diagnosing corneal dystrophy.

BACKGROUND

Real-time PCR can be used to detect differences between nucleic acid sequences having substantially identical sequences. Through the use of differentially labeled fluorescent nucleic acid probes, for example one that binds to a wild type sequence and one that binds to a mutant sequence, single nucleotide changes in the human genome can be quickly and reliably detected. This resolving power has been applied to medical diagnostics, where single nucleotide polymorphisms (SNPs), i.e., single base changes found within the coding and/or non-coding sequence of a protein, are correlated to human disease.

However, real-time PCR analysis is highly dependent upon the collection and isolation of high quality samples. Poor sample collection and/or isolation require the use of longer assay conditions and greater amounts of real-time PCR reagents, both of which result in increased costs and reduced productivity. Furthermore, failure of a real-time PCR single nucleotide polymorphism detection assay can result in the need to collect additional samples, causing even greater loss in time and resources.

Accordingly, methods resulting in improved sample collection and isolation, which improve the overall success rate of the assay, reduce the reagents required for the assay, and reduce the need to collect additional samples at later time are highly desirable. Furthermore, methods for performing real-time PCR SNP detection assays with lower amounts of sample material will also reduce the challenges associated with the collection and isolation of high quality samples.

The cornea is an avascular transparent tissue at the front of the eye that begins the process of focusing light onto the retina and accounts for around two-thirds of the eye's optical power. A number of heritable conditions affect corneal clarity, and they are categorized by the affected corneal layer as posterior, stromal or superficial. Autosomal dominant (AD), X-linked recessive (XR), and autosomal recessive (AR) inheritance patterns have all been observed, and in many cases, the disease locus has been mapped and the causative gene has been identified. The most studied corneal dystrophies are those caused by autosomal dominant missense mutations in the transforming growth factor beta-induced gene (TGFBI) located on chromosome 5q31.1, which encodes an extracellular matrix protein thought to play pivotal roles in physiologic and pathologic responses by mediating cell adhesion, migration, proliferation and differentiation. To date, 62 TGFBI mutations are reported in the Human Gene Mutation Database (HGMD) to cause a spectrum of different epithelial-stromal corneal dystrophies with corneal amyloid and non-amyloid deposits, including granular corneal dystrophy type 1 (GCD1) and type 2 (GCD2, previously designated as Avellino Corneal Dystrophy), epithelial basement membrane dystrophy (EBMD), lattice corneal dystrophy (LCD), Reis-Bücklers corneal dystrophy (RBCD) and Thiel-Behnke corneal dystrophy (TBCD). Different TGFBI mutations can cause specific corneal dystrophies, and a genotype-phenotype correlation has been demonstrated at two mutation hotspots, R124 and R555.

Laser in situ keratomileusis (LASIK) is a surgical procedure that provides vision correction for myopia (nearsightedness), hyperopia (farsightedness), and astigmatism. A thin flap in the corneal epithelium is cut and folded, and the exposed stromal layer is reshaped by laser to change its corneal focusing power. Small incision lenticule extraction (SMILE) is a less invasive surgery for the correction of myopia. A tiny incision is made by the laser in the epithelium layer, and a small piece of stroma (lenticule) is removed to reshape the stroma. Photorefractive keratectomy (PRK) and phototherapeutic keratectomy (PTK) surgery affect vision correction or treat various ocular disorders by removing superficial opacities and surface irregularities from the cornea. These invasive corneal surgeries induce a wound in the stromal layer, which causes the expression of TGFBI to be unregulated, resulting in corneal amyloid deposition within the corneas of individuals who carry the TGFBI mutations leading to pathology associated with corneal dystrophy. LASIK is contraindicated in individuals with granular corneal dystrophy (GCD). A commercially available genetic test, can detect within the TGFBI gene the five most common mutations which are linked to the five more common types of corneal dystrophy: R124H for granular corneal dystrophy type 2, R124C for lattice corneal dystrophy type 1, R124L for Reis-Buckler corneal dystrophy, R555W for granular corneal dystrophy type 1, and R555Q for Thiel-Behnke corneal dystrophy. This five mutation genetic test was originally designed for the Korean and Japanese population, where a majority of the TGFBI corneal dystrophy cases are diagnosed as GCD2 caused by the R124H mutation. Within Korea and Japan, the test is used primarily as a screening tool prior to refractive surgery. However, in the US and Europe, the test is used both to screen refractive surgery candidates and as a confirmatory test for clinical diagnosis of corneal dystrophy disease.

Given the above background, what is needed in the art is to review the prevalence of different TGFBI mutations in various populations and geographic locations to improve the genetic test for use in different populations worldwide.

SUMMARY

In one aspect, the present disclosure provides a reaction mixture for detecting corneal dystrophy in a subject, the reaction mixture comprising a labeled probe comprising a mutant nucleotide sequence selected from the group consisting of SEQ ID NO: 25-30, 36 and 54. The reaction mixture may further comprise a corresponding labeled probe comprising a normal nucleotide sequence selected from the group consisting of SEQ ID NO: 19-24, 33 and 50. In some embodiments, the labeled probe consists of the mutant nucleotide sequence selected from the group consisting of SEQ ID NO: 25-30, 36 and 54; and/or the corresponding labeled probe consists of the normal nucleotide sequence selected from the group consisting of SEQ ID NO: 19-24, 33 and 50. In additional embodiments, the reaction mixture comprises a labeled TGFBI G623D probe comprising the nucleotide sequence of SEQ ID NO: 33 or 36; and a labeled TGFBI M502V probe comprising the nucleotide sequence of SEQ ID NO: 24 or 30. In yet further embodiments, the labeled TGFBI G623D probe comprising the nucleotide sequence of SEQ ID NO: 36; and labeled TGFBI M502V probe comprising the nucleotide sequence of SEQ ID NO: 30.

In some embodiments, the labeled probes are fluorescently labeled. In additional embodiments, each of the labeled probes comprises a different probe. In further embodiments, each of the labeled probes is independently labeled with VIC, FAM, ABY, or JUN.

In some embodiments, the reaction mixture further comprises at least one amplification primer pair for amplifying a TGFBI gene sequence from a biological sample from the subject. In additional embodiments, the reaction mixture comprises (a) a corresponding forward primer comprising a nucleotide sequence selected from the group consisting of SEQ ID NO: 7-12 and 41; and (b) a corresponding reverse primer comprising a nucleotide sequence selected from the group consisting of SEQ ID NO: 13-18 and 47. When the reaction mixture comprises a labeled TGFBI G623D probe comprising the nucleotide sequence of SEQ ID NO: 33 or 36; and a labeled TGFBI M502V probe comprising the nucleotide sequence of SEQ ID NO: 24 or 30, the reaction mixture may further comprise (a) corresponding forward primers comprising SEQ ID NO: 10 and 12; and (b) corresponding reverse primers comprising SEQ ID NO: 16 and 18.

In one aspect, the present disclosure provides a reaction kit comprising the reaction mixture described herein. In one aspect, the reaction kit comprises a reaction mixture comprising detection probes for G623D and M502V mutations in TGBI gene. In some embodiments, the reaction kit further comprises one or more detection probes for R124S, A546D, H572R, and H626R mutations in TGBI gene. In one aspect, the present disclosure provides a reaction kit comprising the reaction mixture described herein, and one or more labeled probes for one or more TGFBI mutations selected from the group consisting of R124S, A546D, H572R, and H626R. In some embodiments, the one or more labeled probes are separate from the reaction mixture. In additional embodiments, the one or more labeled probes are selected from the group of labeled probes comprising or consisting of nucleotide sequences of SEQ ID NO: 19, 25, 20, 26, 21, 27, 23, 29, 50 and 54. In yet additional embodiments, the reaction kit comprises a labeled TGFBI R124S probe comprising the nucleotide sequence of SEQ ID NO: 19 or 25. In yet additional embodiments, the reaction kit comprises a labeled TGFBI A546D probe comprising the nucleotide sequence of SEQ ID NO: 20 or 26. In yet additional embodiments, the reaction kit comprises a labeled TGFBI H572R probe comprising the nucleotide sequence of SEQ ID NO: 21 or 27. In yet additional embodiments, the reaction kit comprises a labeled TGFBI H626R probe comprising the nucleotide sequence of SEQ ID NO: 23, 29, 50 or 54. In further embodiments, the reaction kit further comprises an additional amplification primer set. In yet further embodiments, the reaction kit further comprises a third amplification primer set to amplify a TGFBI gene comprising R124S mutation, a fourth amplification primer set to amplify a TGFBI gene comprising A546D mutation, a fifth amplification primer set to amplify a TGFBI gene comprising H572R mutation, and/or a sixth amplification primer set to amplify a TGFBI gene comprising H626R mutation.

In one aspect, the present disclosure provides a method for detecting corneal dystrophy comprising detecting one, two, three, four, five or six mutations selected from the group consisting of G623D, M502V, R124S, A546D, H572R, and H626R mutations in TGFBI gene. In some embodiments, the detecting comprises sequencing the TGFBI gene. In additional embodiments, the detecting comprises detecting the mutation using a labeled detection probe.

In one aspect, the present disclosure provides a method for detecting corneal dystrophy comprising: (A-1) amplifying a first TGFBI gene sequence from a biological sample from a subject using a reaction mixture comprising at least a first amplification primer pair and a set of at least two detection probes; (B-1) hybridizing first and second detection probes of the set of at least two detection probes to a first TGFBI gene sequence having G623D mutation and a second TGFBI gene sequence having M502V mutation, respectively; and (C-1) detecting one, two or more mutations in the TGFBI gene sequence based on the hybridization of the first and second detection probes to the first and second TGFBI gene sequences, respectively. In some embodiments, the method further comprises (A-2) amplifying a third TGFBI gene sequence from the biological sample, wherein the reaction mixture further comprises a third labeled probe for a third TGFBI mutation selected from the group consisting of R124S, A546D, H572R, and H626R; (B-2) hybridizing the third labeled probe to the third TGFBI gene sequence; and (C-2) detecting a mutation in the third TGFBI gene sequence based on the hybridization of the third detection probe to the third TGFBI gene sequence.

BRIEF DESCRIPTION OF THE DRAWINGS

FIG. 3 provides a table ranking the five most common mutations within reported cases from highest to lowest. In addition, it lists the case numbers from high to low for the six additional mutations.

FIG. 4 provides a table indicating the theoretical results for the available genetic test for R124C, R555W, R124H, R555Q, and R124L. This test would detect 90% of the 68 TGFBI CD cohort identified by the Moorfield's Corneal Dystrophy Study. The table also shows the results using the six additional mutations identified through literature research. They increase the detection rate by 7%, which brings the overall detection rate in the UK to 97%.

FIGS. 5A-5C provide exemplary sequences for targets, primers and probes used in examples.

FIGS. 6A and 6B show discrimination plot results from Example 4 using M502V and G623D TGFBI probes.

DETAILED DESCRIPTION

I. Introduction

Figure 1A:
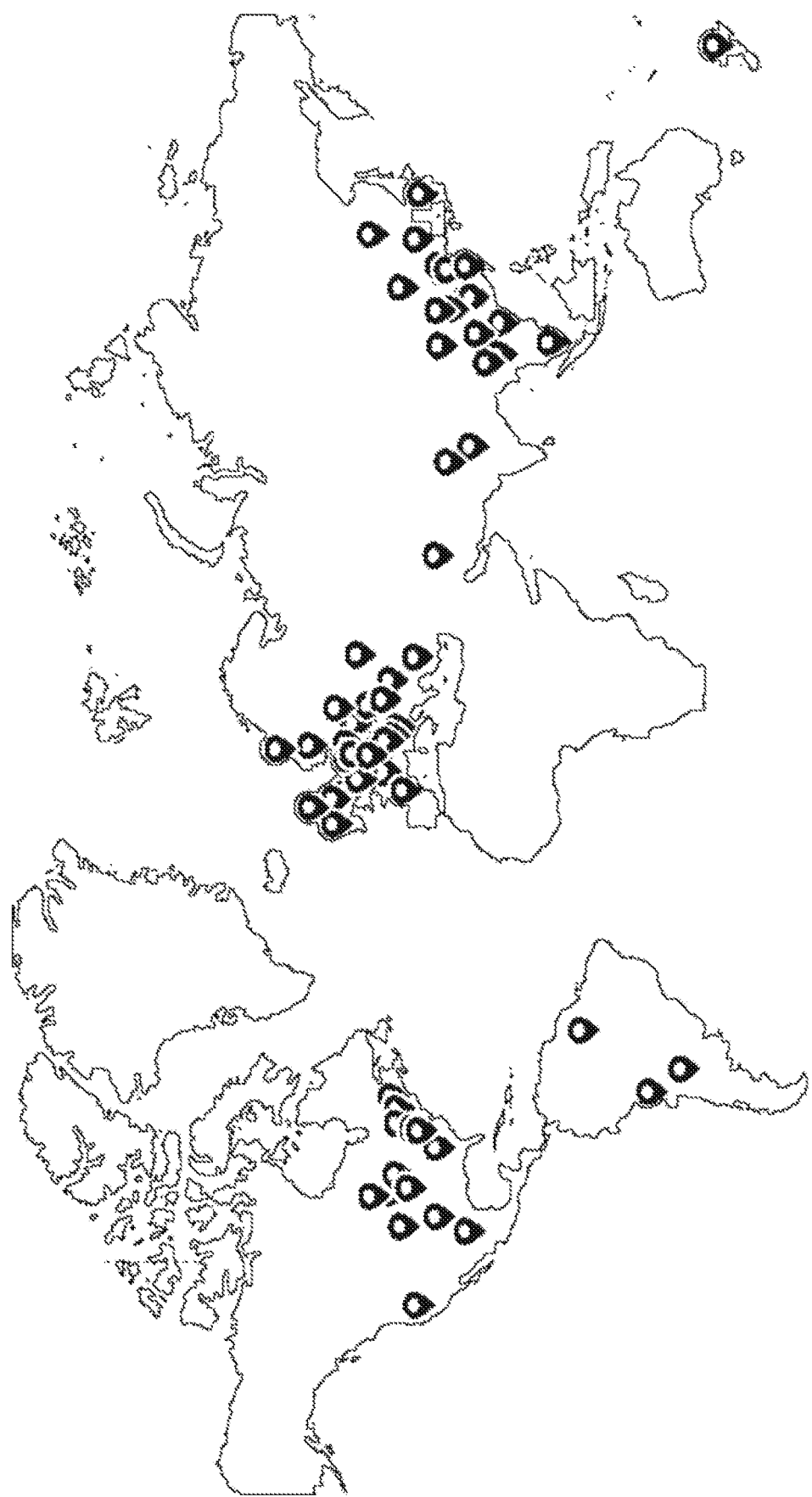
FIG. 1A illustrates world map of reported cases with various TGFBI mutations. Each bubble placed over a region or country contains the reported case information, such as ethnicities, mutations and case numbers. The map illustrates that TGFBI mutations cases are reported all over the world, except for in regions with limited research capacity or language difficulties for publication. Very few cases were reported from South America, and no case reports were identified from Africa or Russia.

The present disclosure is based at least in part on the discovery of a reaction mixture, reaction kit to improve the detection of corneal dystrophy.

The reported prevalence of TGFBI corneal dystrophies in Asia is 1 in 870 in Korea and 1 in 416 in China. Asia has a high myopia rate, and a study conducted by Holden et al. predicted that by 2050, the Asian-Pacific population will have the highest myopia prevalence rate among all populations at 66.4% compared to the global prevalence of 49.8%. With the high prevalence of myopia in these Asian populations, the use of LASIK vision correction surgery is consistently increasing and is predicted to continue to rise. With the known prevalence of TGFBI mutations in the Asian population and the high myopia rate, mutation testing is important in this region; subsequently, the five-mutation genetic test was initially introduced in Asian-Pacific populations.

Since the first description by Folberg et al., in 1988 of TGFBI mutations as the cause of granular corneal dystrophy, our awareness and understanding of this disease has increased steadily. The most common R124 and R555 mutations are well documented, and additional mutations are being examined more closely to understand the next tier of common variants. The disclosure provides the review of reports in the literature on various TGFBI corneal dystrophies to understand the prevalence of this disease. The worldwide prevalence of this disease is unknown; however, the disease outcome is debilitating. The ultimate treatment is corneal transplant, and the recurrent nature of the disease often requires subsequent corneal transplants, which is traumatic and costly to both the patients and the ophthalmologist. Therefore, prevention and prescreening with molecular diagnostic testing to detect mutations is key.

In some embodiments, one object is to provide enhanced testing capability in the prescreening test prior to refractive surgery. Another objective is to close the gap between the detection rate resulting from genetic testing and clinical diagnosis.

II. Select Definitions

The term "invention" or "present invention" as used herein is not meant to be limiting to any one specific embodiment of the invention but applies generally to any and all embodiments of the invention as described in the claims and specification.

As used herein, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure.

As used herein, the term "polymorphism" and variants thereof refers to the occurrence of two or more alternative genomic sequences or alleles between or among different genomes or individuals. The terms "genetic mutation" or "genetic variation" and variants thereof include polymorphisms.

As used herein the term "single nucleotide polymorphism" ("SNP") and variants thereof refers to a site of one nucleotide that varies between alleles. A single nucleotide polymorphism (SNP) is a single base change or point mutation but also includes the so-called "indel" mutations (insertions or deletions of a nucleotide), resulting in genetic variation between individuals. SNPs, which make up about 90% of all human genetic variation, occur every 100 to 300 bases along the 3-billion-base human genome. SNPs can occur in coding or non-coding regions of the genome. A SNP in the coding region may or may not change the amino acid sequence of a protein product. A SNP in a non-coding region can alter promoters or processing sites and may affect gene transcription and/or processing. Knowledge of whether an individual has particular SNPs in a genomic region of interest may provide sufficient information to develop diagnostic, preventive and therapeutic applications for a variety of diseases. In some embodiments, the present disclosure relates to the detection of SNPs in coding regions that alter the amino acid sequences resulting in mutations in amino acid sequences of a product from TGBI gene. For example, the present disclosure relates to the detection of SNPs causing G623D, M502V, R124S, A546D, H572R, H626R, G623D, R124S, H403Q, R124C and/or R124H mutations in TGFBI gene.

The term "primer" and variants thereof refers to an oligonucleotide that acts as a point of initiation of DNA synthesis in a PCR reaction. A primer is usually about 15 to about 35 nucleotides in length and hybridizes to a region complementary to the target sequence.

The term "probe" and variants thereof (e.g., detection probe) refers to an oligonucleotide that hybridizes to a target nucleic acid in a PCR reaction. Target sequence refers to a region of nucleic acid that is to be analyzed and comprises the polymorphic site of interest.

Unless defined otherwise, all technical and scientific terms used herein have the same meaning as commonly understood by those of ordinary skill in the art to which the invention pertains. Although any methods and materials similar or equivalent to those described herein can be used in the practice or testing of the present invention, various embodiments of methods and materials are specifically described herein.

III. Reaction Mixture

In one aspect, the present disclosure provides a reaction mixture for detecting corneal dystrophy in a subject, the reaction mixture comprising a detection probe to detect a mutation in TGBI. In some embodiments, the detection probes detect SNPs causing the amino acid mutations described herein. In one aspect, the present disclosure provides a reaction mixture for detecting corneal dystrophy in a subject, the reaction mixture comprising a mutant nucleotide sequence selected from the group consisting of SEQ ID NO: 25-30, 36 and 54. The reaction mixture may further comprise a corresponding labeled probe comprising a normal nucleotide sequence selected from the group consisting of SEQ ID NO: 19-24, 33 and 50. In some embodiments, the labeled probe consists of the mutant nucleotide sequence selected from the group consisting of SEQ ID NO: 25-30, 36 and 54; and/or the corresponding labeled probe consists of the normal nucleotide sequence selected from the group consisting of SEQ ID NO: 19-24, 33 and 50. In additional embodiments, the reaction mixture comprises a labeled TGFBI G623D probe comprising the nucleotide sequence of SEQ ID NO: 33 or 36; and a labeled TGFBI M502V probe comprising the nucleotide sequence of SEQ ID NO: 24 or 30. In yet further embodiments, the labeled TGFBI G623D probe comprising the nucleotide sequence of SEQ ID NO: 36; and labeled TGFBI M502V probe comprising the nucleotide sequence of SEQ ID NO: 30.

In some embodiments, the reaction mixture further comprises at least one amplification primer pair for amplifying a TGFBI gene sequence from a biological sample from the subject. In additional embodiments, the reaction mixture comprises (a) a corresponding forward primer comprising a nucleotide sequence selected from the group consisting of SEQ ID NO: 7-12 and 41; and (b) a corresponding reverse primer comprising a nucleotide sequence selected from the group consisting of SEQ ID NO: 13-18 and 47. When the reaction mixture comprises a labeled TGFBI G623D probe comprising the nucleotide sequence of SEQ ID NO: 33 or 36; and a labeled TGFBI M502V probe comprising the nucleotide sequence of SEQ ID NO: 24 or 30, the reaction mixture may further comprise (a) corresponding forward primers comprising SEQ ID NO: 10 and 12; and (b) corresponding reverse primers comprising SEQ ID NO: 16 and 18.

In some embodiments, the labeled probes are fluorescently labeled. In additional embodiments, each of the labeled probes comprises a different probe. In further embodiments, each of the labeled probes is independently labeled with VIC, FAM, ABY, or JUN.

IV. Diagnostic Kits

In one aspect, any or all of the reagents described herein are packaged into a diagnostic kit. Such kits include any and/or all of the primers, probes, buffers and/or other reagents described herein in any combination.

In one aspect, the present disclosure provides a reaction kit comprising primer sets, detection probes and/or reagents to detect R124S, A546D, H572R, H626R, G623D and M502V mutations in TGBI gene. In one aspect, the present disclosure provides a reaction kit comprising primer sets, detection probes and/or reagents to detect G623D and M502V mutations in TGBI gene with a single reaction mixture comprising the combination of primer sets, probes and/or reagents to detect G623D and M502V. In some embodiments, the reaction kit further comprises one, two, three or four primer sets, detection probes and/or reagents to detect one, two, three or four TGFBI mutations selected from the group consisting of R124S, A546D, H572R, and H626R. In additional embodiments, the reaction kit further comprises one, two, three, four or five primer sets, detection probes and/or reagents to detect one, two, three, four or five TGFBI mutations selected from the group consisting of G623D, R124S, H403Q, R124C and R124H.

In one aspect, the present disclosure provides a reaction kit comprising the reaction mixture described above and one or more additional reagents. In some embodiments, the reaction kit further comprises one, two, three or four primer sets, labeled probes and/or reagents to detect one, two, three or four TGFBI mutations selected from the group consisting of R124S, A546D, H572R, and H626R. In some embodiments, the one, two, three or four primer sets, labeled probes and/or reagents to detect one, two, three or four TGFBI mutations selected from the group consisting of R124S, A546D, H572R, and H626R are separate from the reaction mixture in the kit. In additional embodiments, the reaction kit comprises 1, 2, 3, 4, 5, 6, 7, 8, 9, 10, 11, 12, 13, 14, 15, 16 or 17 labeled probes selected from the group consisting of labeled probes comprising nucleotide sequences of SEQ ID NO: 19-24, 33, 50, 25-30, 36 and 54. In yet additional embodiments, the reaction kit comprises a labeled TGFBI R124S normal probe comprising the nucleotide sequence of SEQ ID NO: 19 and/or a labeled TGFBI R124S mutant probe comprising the nucleotide sequence of SEQ ID NO: 25. In yet additional embodiments, the reaction kit comprises a labeled TGFBI A546D normal probe comprising the nucleotide sequence of SEQ ID NO: 20 and/or a labeled TGFBI A546D mutant probe comprising the nucleotide sequence of SEQ ID NO: 26. In yet additional embodiments, the reaction kit comprises a labeled TGFBI H572R normal probe comprising the nucleotide sequence of SEQ ID NO: 21, and/or a labeled TGFBI H572R mutant probe comprising the nucleotide sequence of SEQ ID NO: 27. In yet additional embodiments, the reaction kit comprises a labeled TGFBI H626R normal probe comprising the nucleotide sequence of SEQ ID NO: 23 or 50, and/or a labeled TGFBI H626R mutant probe comprising the nucleotide sequence of SEQ ID NO: 29 or 54. In yet additional embodiments, the reaction kit excludes a kit wherein a TGFBI G623D probe is kept separately or not mixed with a TGBI M502V probe.

In further embodiments, the reaction kit further comprises an additional amplification primer set. In yet further embodiments, the reaction kit further comprises a third amplification primer set to amplify a TGFBI gene comprising the R124S mutation, a fourth amplification primer set to amplify a TGFBI gene comprising A546D mutation, a fifth amplification primer set to amplify a TGFBI gene comprising H572R mutation, and/or a sixth amplification primer set to amplify a TGFBI gene comprising H626R mutation. Herein, a TGFBI gene comprising the R124S mutation may refer to a TGFBI gene comprising a SNP causing the R124S mutation in TGBI protein product.

In additional embodiments, the reaction kit further comprises one, two, three, four or five primer sets, detection probes and/or reagents to detect one, two, three, four or five TGFBI mutations selected from the group consisting of G623D, R124S, H403Q, R124C and R124H.

In some embodiments, the reagents in the kit are included as lyophilized powders. In some embodiments, the reagents in the kit are included as lyophilized powders with instructions for reconstitution. In some embodiments, the reagents in the kit are included as liquids. In some embodiments, the reagents are included in plastic and/or glass vials or other appropriate containers. In some embodiments the primers and probes are all contained in individual containers in the kit. In some embodiments, the primers are packaged together in one container, and the probes are packaged together in another container. In some embodiments, the primers and probes are packaged together in a single container.

In some embodiments, the kit further includes control gDNA and/or DNA samples. In some embodiments the control DNA sample included is TGFBI sample having G623 normal sequence and/or TGFBI sample having M502 normal sequences. In some embodiments the control DNA sample included corresponds to the mutation being detected, including R124S, A546D, H572R, and H626R. In some embodiments, a control DNA sample corresponding to TGFBI R124 normal and a mutant DNA sample corresponding to R124C, R124H, R124L, R555W, R555Q and/or H626P are included. In some embodiments, a control DNA sample corresponding to TGFBI R124 normal and a mutant DNA sample corresponding to R124C, R124H, R124L, R555W and/or R555Q are included. In some embodiments, a control DNA sample corresponding to TGFBI R124 normal and a mutant DNA sample corresponding to R124C, R124H and/or R124L are included. In some embodiments, a control DNA sample corresponding to TGFBI R124 normal and a mutant DNA sample corresponding to R555W and/or R555Q are included. In some embodiments, a control DNA sample corresponding to TGFBI R124 normal and a mutant DNA sample corresponding to R124C are included. In some embodiments, a control DNA sample corresponding to TGFBI R124 normal DNA and a mutant DNA sample corresponding to R124H are included. In some embodiments, a control DNA sample corresponding to TGFBI R124 normal and a mutant DNA sample corresponding to R124L are included. In some embodiments, a control DNA sample corresponding to TGFBI R124 normal DNA and a mutant DNA sample corresponding to R555W are included. In some embodiments, a control DNA sample corresponding to TGFBI R124 normal and mutant DNA sample corresponding to R555Q are included. In some embodiments, a control DNA sample corresponding to TGFBI R124 normal and mutant DNA sample corresponding to H626P are included.

In some embodiments, the concentration of the control DNA sample is 5 ng/µL, 10 ng/µL, 20 ng/µL, 30 ng/µL, 40 ng/µL, 50 ng/µL, 60 ng/µL, 70 ng/µL, 80 ng/µL, 90 ng/µL, 100 ng/µL, 110 ng/µL, 120 ng/µL, 130 ng/µL, 140 ng/µL, 150 ng/µL, 160 ng/µL, 170 ng/µL, 180 ng/µL, 190 ng/4 or 200 ng/4. In some embodiments, the concentration of the control DNA sample is 50 ng/µL, 100 ng/µL, 150 ng/4 or 200 ng/4. In some embodiments, the concentration of the control DNA sample is 100 ng/4. In some embodiments, the control DNA samples have the same concentration. In some embodiments, the control DNA samples have different concentrations.

In some embodiments, the kit can further include buffers, for example, GTXpress TAQMAN® reagent mixture, or any equivalent buffer. In some embodiments, the buffer includes any buffer described herein.

In some embodiments, the kit can further include reagents for use in cloning, such as vectors (including, e.g., M13 vector).

In some embodiments, the kit further includes reagents for use in purification of DNA.

In some embodiments, the kit further includes instructions for using the kit for the detection of corneal dystrophy in a subject. In some embodiments, these instructions include various aspects of the protocols described herein.

V. Nucleic Acid Analyses

In one aspect, the present disclosure provides a method for detecting corneal dystrophy comprising detecting one, two, three, four, five or six TGFBI mutations selected from the group consisting of G623D, M502V, R124S, A546D, H572R, and H626R mutations in TGFBI gene. In some embodiments, the method may further comprise detecting one, two, three, four, or five TGFBI mutations selected from the group consisting of G623D, R124S, H403Q, R124C and R124H.

In some embodiments, the detecting comprises sequencing the TGFBI gene. In additional embodiments, the detecting comprises detecting the mutation using a labeled detection probe.

In one aspect, the present disclosure provides a method for detecting corneal dystrophy comprising: (A-1) amplifying a first TGFBI gene sequence from a biological sample from a subject using a reaction mixture comprising at least a first amplification primer pair and a set of at least two detection probes; (B-1) hybridizing first and second detection probes of the set of at least two detection probes to a first TGFBI gene sequence having G623D mutation and a second TGFBI gene sequence having M502V mutation, respectively; and (C-1) detecting one, two or more mutations in the TGFBI gene sequence based on the hybridization of the first and second detection probes to the first and second TGFBI gene sequences, respectively. In some embodiments, the method further comprises (A-2) amplifying a third TGFBI gene sequence from the biological sample, wherein the reaction mixture further comprises a third labeled probe for a third TGFBI mutation selected from the group consisting of R124S, A546D, H572R, and H626R; (B-2) hybridizing the third labeled probe to the third TGFBI gene sequence; and (C-2) detecting a mutation in the third TGFBI gene sequence based on the hybridization of the third detection probe to the third TGFBI gene sequence.

In some embodiments, the methods herein further comprises isolating a genomic samples. In some embodiments, the method includes providing a sample of cells from a subject. In additional embodiments, the subject may be human. In some embodiments, the cells are collected by contacting a cellular surface of a patient with a substrate capable of reversibly immobilizing the cells onto a substrate.

The disclosed methods are applicable to a variety of cell types obtained from a variety of samples. In some embodiments, the cell type for use with the disclosed methods include but is not limited to epithelial cells, endothelial cells, connective tissue cells, skeletal muscle cells, endocrine cells, cardiac cells, urinary cells, melanocytes, keratinocytes, blood cells, white blood cells, buffy coat, hair cells (including, e.g., hair root cells) and/or salival cells. In some embodiments, the cells are epithelial cells. In some embodiments, the cells are subcapsular-perivascular (epithelial type 1); pale (epithelial type 2); intermediate (epithelial type 3); dark (epithelial type 4); undifferentiated (epithelial type 5); and large-medullary (epithelial type 6). In some embodiments, the cells are buccal epithelial cells (e.g., epithelial cells collected using a buccal swap). In some embodiments, the sample of cells used in the disclosed methods include any combination of the above identified cell types. In some embodiments, the cells provided are buccal epithelial cells.

In some embodiments, the sample is advantageously collected in a non-invasive manner and as such sample collection is accomplished anywhere and by almost anyone. For example, in some embodiments the sample is collected at a physician's office, at a subject's home, or at a facility where LASIK surgery is performed or to be performed. In some embodiments the patient, the patient's doctor, nurses or a physician's assistant or other clinical personnel collects the sample.

A variety of methods for analyzing the SNPs in a sample including, for example but not limited to genomic DNA (gDNA) sample, are known in the art and may include PCR methods, such as real-time PCR analysis, microarray analysis, hybridization analysis and nucleic acid sequence analysis, as well as a variety of other methods where nucleic acid compositions are analyzed and which are known to those of skill in the art. See, for example, Molecular Cloning (three volume set, Cold Spring Harbor Laboratory Press, 2012) and Current Protocols (Genetics and Genomics; Molecular Biology; 2003-2013).

a. Real-Time PCR

For the design of Real-Time PCR assays, several parts are coordinated, including the DNA fragment that is flanked by the two primers and subsequently amplified, often referred to as the amplicon, the two primers and the detection probe or probes to be used.

Real-time PCR relies on the visual emission of fluorescent dyes conjugated to short polynucleotides (termed "detection probes") that associate with genomic alleles in a sequence-specific fashion. Real-time PCR probes differing by a single nucleotide can be differentiated in a real-time PCR assay by the conjugation and detection of probes that fluoresce at different wavelengths. Real-Time PCR finds use in detection applications (diagnostic applications), quantification applications and genotyping applications.

Several related methods for performing real-time PCR are disclosed in the art, including assays that rely on TAQMAN® probes (U.S. Pat. Nos. 5,210,015 and 5,487,972, and Lee et al., *Nucleic Acids Res.* 21:3761-6, 1993), molecular beacon probes (U.S. Pat. Nos. 5,925,517 and 6,103,476, and Tyagi and Kramer, *Nat. Biotechnol.* 14:303-8, 1996), self-probing amplicons (scorpions) (U.S. Pat. No. 6,326,145, and Whitcombe et al., *Nat. Biotechnol.* 17:804-7, 1999), Amplisensor (Chen et al., *Appl. Environ. Microbiol.* 64:4210-6, 1998), Amplifluor (U.S. Pat. No. 6,117,635, and Nazarenko et al., *Nucleic Acids Res.* 25:2516-21, 1997, displacement hybridization probes (Li et al., *Nucleic Acids Res.* 30:E5, 2002), DzyNA-PCR (Todd et al., *Clin. Chem.* 46:625-30, 2000), fluorescent restriction enzyme detection (Cairns et al., *Biochem. Biophys. Res. Commun.* 318:684-90, 2004) and adjacent hybridization probes (U.S. Pat. No. 6,174,670 and Wittwer et al., *Biotechniques* 22:130-1, 134-8, 1997).

In one aspect, the present disclosure relates to the detection of SNPs causing G623D, M502V, R124S, A546D, H572R, H626R, G623D, R124S, H403Q, R124C and/or R124H mutations in TGFBI gene. In some instances, real-time PCR can result in detection of a variety of gene mutations, including for example but not limited to SNPs. In some embodiments, detection of SNPs in specific gene candidates is performed using real-time PCR, based on the use of intramolecular quenching of a fluorescent molecule by use of a tethered quenching moiety. Thus, according to exemplary embodiments, real-time PCR methods also include the use of molecular beacon technology. The molecular beacon technology utilizes hairpin-shaped molecules with an internally-quenched fluorophore whose fluorescence is restored by binding to a DNA target of interest (See, e.g., Kramer, R. et al. *Nat. Biotechnol.* 14:303-308, 1996). In some embodiments, increased binding of the molecular beacon probe to the accumulating PCR product is used to specifically detect SNPs present in genomic DNA.

One of the many suitable genotyping procedures is the TAQMAN® allelic discrimination assay. In some instances of this assay, an oligonucleotide probe labeled with a fluorescent reporter dye at the 5' end of the probe and a quencher dye at the 3' end of the probe is utilized. The proximity of the quencher to the intact probe maintains a low fluorescence for the reporter. During the PCR reaction, the 5' nuclease activity of DNA polymerase cleaves the probe, and separates the dye and quencher. This results in an increase in fluorescence of the reporter. Accumulation of PCR product is detected directly by monitoring the increase in fluorescence of the reporter dye. The 5' nuclease activity of DNA polymerase cleaves the probe between the reporter and the quencher only if the probe hybridizes to the target and is amplified during PCR. The probe is designed to straddle a target SNP position and hybridize to the nucleic acid molecule only if a particular SNP allele is present.

By way of example, to amplify the Avellino corneal dystrophy associated SNP located in exon 4 of the TGFBI gene, forward and reverse PCR primer pairs were constructed as described in U.S. Patent Publication No. 2012/0077200, the disclosure of which is incorporated by reference herein.

b. Real-Time PCR Cycles

Real-time PCR methods include a variety of steps or cycles as part of the methods for amplification. These cycles include denaturing double-stranded nucleic acids, annealing a forward primer, a reverse primer and a detection probe to the target genomic DNA sequence and synthesizing (i.e., replicating) second-strand DNA from the annealed forward primer and the reverse primer. This three step process is referred to herein as a cycle.

In some embodiments, about 10, 15, 20, 25, 30, 35, 40, 45, 50, 55, or 60 cycles are employed. In some embodiments, about 10 to about 60 cycles, about 20 to about 50 or about 30 to about 40 cycles are employed. In some embodiments, 40 cycles are employed.

In some embodiments, the denaturing double-stranded nucleic acids step occurs at a temperature of about 80° C. to 100° C., about 85° C. to about 99° C., about 90° C. to about 95° C. for about 1 second to about 5 seconds, about 2 seconds to about 5 seconds, or about 3 seconds to about 4 seconds. In some embodiments, the denaturing double-stranded nucleic acids step occurs at a temperature of 95° C. for about 3 seconds.

In some embodiments, the annealing a forward primer, a reverse primer and a detection probe to the target genomic DNA sequence step occurs at about 40° C. to about 80° C., about 50° C. to about 70° C., about 55° C. to about 65° C. for about 15 seconds to about 45 seconds, about 20 seconds to about 40 seconds, about 25 seconds to about 35 seconds. In some embodiments, the annealing a forward primer, a reverse primer and a detection probe to the target genomic DNA sequence step occurs at about 60° C. for about 30 seconds.

In some embodiments, the synthesizing (i.e., replicating) second-strand DNA from the annealed forward primer and the reverse primer occurs at about 40° C. to about 80° C., about 50° C. to about 70° C., about 55° C. to about 65° C. for about 15 seconds to about 45 seconds, about 20 seconds to about 40 seconds, about 25 seconds to about 35 seconds. In some embodiments, the annealing a forward primer, a reverse primer and a detection probe to the target genomic DNA sequence step occurs at about 60° C. for about 30 seconds.

In some embodiments, it was found that about 1 µL, about 2 µL, about 3 µL, about 4 µL or about 54 of a genomic DNA sample prepared according to the present methods described herein, are combined with only about 0.05 µL, about 0.10 µL, about 0.15 µL, about 0.20 µL, about 0.25 µL or about 0.25 µL of a 30×, 35×, 40×, 45×, 50× or 100× real-time PCR assay mix and distilled water to form the PCR master mix. In some embodiments, the PCR master mix has a final volume of about 1.5 µL, about 2.5 µL, about 5 µL, about 6 µL, about 7 µL, about 8 µL, about 9 µL, about 0 µL, about 11 µL, about 12 µL, about 13 µL, about 14 µL, about 15 µL, about 16 µL, about 17 µL, about 18 µL, about 19 µL or about 20 µL or more. In some embodiments, it was found that 2 µL of a genomic DNA sample prepared as described above, are combined with only about 0.15 µL of a 40× real-time PCR assay mix and 2.85 µL of distilled water in order to form the PCR master mix.

While exemplary reactions are described herein, one of skill would understand how to modify the temperatures and times based on the probe design. Moreover, the present methods contemplate any combination of the above times and temperatures.

c. PCR Primers and Primer Design

In some embodiments, primers are tested and designed in a laboratory setting. In some embodiments, primers are designed by computer based in silico methods. Primer sequences are based on the sequence of the amplicon or target nucleic acid sequence that is to be amplified. Shorter amplicons typically replicate more efficiently and lead to more efficient amplification as compared to longer amplicons.

In designing primers, one of skill would understand the need to take into account melting temperature ($T_m$; the temperature at which half of the primer-target duplex is dissociated and becomes single stranded and is an indication of duplex stability; increased $T_m$ indicates increased stability) based on GC and AT content of the primers being designed as well as secondary structure considerations (increased GC content can lead to increased secondary structure). $T_M$'s can be calculated using a variety of methods known in the art and those of skill would readily understand such various methods for calculating $T_M$; such methods include for example but are not limited to those available in online tools such as the $T_M$ calculators available on the World Wide Web at promega.com/techserv/tools/biomath/calc11.htm. Primer specificity is defined by its complete sequence in combination with the 3' end sequence, which is the portion elongated by Taq polymerase. In some embodiments, the 3' end should have at least 5 to 7 unique nucleotides not found anywhere else in the target sequence, in order to help reduce false-priming and creation of incorrect amplification products. Forward and reverse primers typically bind with similar efficiency to the target. In some instances, tools such as NCBI BLAST (located on the World Wide Web at ncbi.nlm.nih.gov) are employed to performed alignments and assist in primer design.

An additional aspect of primer design is primer complexity or linguistic sequence complexity (see, Kalendar R, et al. (*Genomics*, 98(2): 137-144 (2011)). Primers with greater linguistic sequence complexity (e.g., nucleotide arrangement and composition) are typically more efficient. In some embodiments, the linguistic sequence complexity calculation method is used to search for conserved regions between compared sequences for the detection of low-complexity regions including simple sequence repeats, imperfect direct or inverted repeats, polypurine and polypyrimidine triple-stranded cDNA structures, and four-stranded structures (such as G-quadruplexes). In some embodiments, linguistic complexity (LC) measurements are performed using the alphabet-capacity L-gram method (see, A. Gabrielian, A. Bolshoy, *Computer & Chemistry* 23:263-274 (1999) and Y. L. Orlov, V. N. Potapov, Complexity: an internet resource for analysis of DNA sequence complexity, *Nucleic Acids Res.* 32: W628-W633 (2004)) along the whole sequence length and calculated as the sum of the observed range (xi) from 1 to L size words in the sequence divided by the sum of the expected (E) value for this sequence length. Some G-rich (and C-rich) nucleic acid sequences fold into four-stranded DNA structures that contain stacks of G-quartets (see, the World Wide Web at quadruplex.org). In some instances, these quadruplexes are formed by the intermolecular association of two or four DNA molecules, dimerization of sequences that contain two G-bases, or by the intermolecular folding of a single strand containing four blocks of guanines (see, P. S. Ho, *PNAS*, 91:9549-9553 (1994); I. A. Il'icheva, V. L. Florent'ev, *Russian Journal of Molecular Biology* 26:512-531(1992); D. Sen, W. Gilbert, *Methods Enzymol.* 211:191-199 (1992); P. A. Rachwal, K. R. Fox, *Methods* 43:291-301 (2007); S. Burge, G. N. Parkinson, P. Hazel, A. K. Todd, K. Neidle, *Nucleic Acids Res.* 34:5402-5415 (2006); A. Guédin, J. Gros, P. Alberti, J. Mergny, *Nucleic Acids Res.* 38:7858-7868 (2010); O. Stegle, L. Payet, J. L. Mergny, D. J. MacKay, J. H. Leon, *Bioinformatics* 25:i374-i382 (2009); in some instances, these are eliminated from primer design because of their low linguistic complexity, LC=32% for $(TTAGGG)_4$.

These methods include various bioinformatics tools for pattern analysis in sequences having GC skew, (G−C)/(G+C), AT skew, (A−T)/(A+T), CG−AT skew, (S−W)/(S+W), or purine-pyrimidine (R−Y)/(R+Y) skew regarding CG content and melting temperature and provide tools for determining linguistic sequence complexity profiles. For example the GC skew in a sliding window of n, where n is a positive integer, bases is calculated with a step of one base, according to the formula, (G−C)/(G+C), in which G is the total number of guanines and C is the total number of cytosines for all sequences in the windows (Y. Benita, et al., *Nucleic Acids Res.* 31:e99 (2003)). Positive GC-skew values indicated an overabundance of G bases, whereas negative GC-skew values represented an overabundance of C bases. Similarly, other skews are calculated in the sequence. Such methods, as well as others, are employed to determine primer complexity in some embodiments.

According to non-limiting example embodiments, real-time PCR is performed using exonuclease primers (TAQMAN® probes). In such embodiments, the primers utilize the 5' exonuclease activity of thermostable polymerases such as Taq to cleave dual-labeled probes present in the amplification reaction (See, e.g., Wittwer, C. et al. Biotechniques 22:130-138, 1997). While complementary to the PCR product, the primer probes used in this assay are distinct from the PCR primer and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of Taq during amplification, the quenching is greatly reduced leading to increased fluorescent signal. Non-limiting examples of fluorescent probes include the 6-carboxy-floruescein moiety and the like. Exemplary quenchers include Black Hole Quencher 1 moiety and the like.

Exemplary primers include but are not limited to those described herein. Primers for use in the disclosed methods are also found in U.S. Patent Publication No. 20120077200, which is hereby incorporated by reference for all purposes. In some embodiments, the PCR primers for use in the methods of the present disclosure include but are not limited to the following listed in Table of FIGS. 5B and 5C, and find use in the detection of the TGFBI gene. Biophysical parameters for each primer may be calculated using the World Wide Web at primerdigital.com/tools/PrimerAnalyser.html.

In some embodiments, the real-time PCR primers for use with the disclosed methods have a linguistic sequence complexity of at least 70%, at least 72%, at least 75%, at least 77%, at least 80%, at least 82%, at least 85%, at least 88%, at least 90%, at least 92%, at least 95%, at least 97% or at least 99%.

d. Detection Probe Design and Detection Probes

Detection probes commonly employed by those of skill in the art include but are not limited to hydrolysis probes (also known as TAQMAN® probes, 5' nuclease probes or dual-labeled probes), hybridization probes, and Scorpion primers (which combine primer and detection probe in one molecule). In some embodiments, probes are designed to have higher Tm's than the primers in order to promote efficient signal production. $T_m$'s are calculated using any of a variety of methods known in the art and those of skill would readily understand such various methods for calculating Tm; such methods include for example those available in online tools such as the calculators available on the World Wide Web at promega.com/techserv/tools/biomath/calc11.htm.

In some embodiments, detection probes contain various modifications. In some embodiments, detection probes include modified nucleic acid residues, such as but not limited to 2'-O-methyl ribonucleotide modifications, phosphorothioate backbone modifications, phosphorodithioate backbone modifications, phosphoramidate backbone modifications, methylphosphonate backbone modifications, 3' terminal phosphate modifications and/or 3' alkyl substitutions.

In some embodiments, the detection probe has increased affinity for a target sequence due to modifications. Such detection probes include detection probes with increased length, as well as detection probes containing chemical modifications. Such modifications include but are not limited to 2'-fluoro (2'-deoxy-2'-fluoro-nucleosides) modifications, LNAs (locked nucleic acids), PNAs (peptide nucleic acids), ZNAs (zip nucleic acids), morpholinos, methylphosphonates, phosphoramidates, polycationic conjugates and 2'-pyrene modifications. In some embodiments, the detector probes contains one or more modifications including 2' fluoro modifications (aka, 2'-Deoxy-2'-fluoro-nucleosides), LNAs (locked nucleic acids), PNAs (peptide nucleic acids), ZNAs (zip nucleic acids), morpholinos, methylphosphonates, phosphoramidates, and/or polycationic conjugates.

In some embodiments, the detection probes contain detectable moieties, such as those described herein as well as any detectable moieties known to those of skill in the art. Such detectable moieties include for example but are not limited to fluorescent labels and chemiluminescent labels. Examples of such detectable moieties can also include members of FRET pairs. In some embodiments, the detection probe contains a detectable entity.

Examples of fluorescent labels include but are not limited to ABY, JUN, AMCA, DEAC (7-Diethylaminocoumarin-3-carboxylic acid); 7-Hydroxy-4-methylcoumarin-3; 7-Hydroxycoumarin-3; MCA (7-Methoxycoumarin-4-acetic acid); 7-Methoxycoumarin-3; AMF (4'-(Aminomethyl)fluorescein); 5-DTAF (5-(4,6-Dichlorotriazinyl)aminofluorescein); 6-DTAF (6-(4,6-Dichlorotriazinyl)aminofluorescein); 6-FAM (6-Carboxyfluorescein; aka FAM; including TAQMAN® FAM™); TAQMAN VIC®; 5(6)-FAM cadaverine; 5-FAM cadaverine; 5(6)-FAM ethylenediamme; 5-FAM ethylenediamme; 5-FITC (FITC Isomer I; fluorescein-5-isothiocyanate); 5-FITC cadaverin; Fluorescein-5-maleimide; 5-IAF (5-Iodoacetamidofluorescein); 6-JOE (6-Carboxy-4',5'-dichloro-2',7'-dimethoxyfluorescein); 5-CR110 (5-Carboxyrhodamine 110); 6-CR110 (6-Carboxyrhodamine 110); 5-CR6G (5-Carboxyrhodamine 6G); 6-CR6G (6-Carboxyrhodamine 6G); 5(6)-Caroxyrhodamine 6G cadaverine; 5(6)-Caroxyrhodamine 6G ethylenediamme; 5-ROX (5-Carboxy-X-rhodamine); 6-ROX (6-Carboxy-X-rhodamine); 5-TAMRA (5-Carboxytetramethylrhodamine); 6-TAMRA (6-Carboxytetramethylrhodamine); 5-TAMRA cadaverine; 6-TAMRA cadaverine; 5-TAMRA ethylenediamme; 6-TAMRA ethylenediamme; 5-TMR C6 maleimide; 6-TMR C6 maleimide; TR C2 maleimide; TR cadaverine; 5-TRITC; G isomer (Tetramethylrhodamine-5-isothiocyanate); 6-TRITC; R isomer (Tetramethylrhodamine-6-isothiocyanate); Dansyl cadaverine (5-Dimethylaminonaphthalene-1-(N-(5-aminopentyl))sulfonamide); EDANS C2 maleimide; fluorescamine; NBD; and pyrromethene and derivatives thereof.

Examples of chemiluminescent labels include but are not limited to those labels used with Southern Blot and Western Blot protocols (see, for e.g., Sambrook and Russell, Molecular Cloning: A Laboratory Manual, (3rd ed.) (2001); incorporated by reference herein in its entirety). Examples include but are not limited to -(2'-spiroadamantane)-4-methoxy-4-(3"-phosphoryloxy)phenyl-1,2-dioxetane (AMPPD); acridinium esters and adamantyl-stabilized 1,2-dioxetanes, and derivatives thereof.

In some embodiments, the labeled probes are used to hybridize within the amplified region during amplification. The probes may be modified so as to avoid them from acting as primers for amplification. The detection probe may be labeled with two fluorescent dyes, one capable of quenching the fluorescence of the other dye. One dye is attached to the 5' terminus of the probe and the other is attached to an internal site, so that quenching occurs when the probe is in a non-hybridized state.

Typically, real-time PCR probes consist of a pair of dyes (a reporter dye and an acceptor dye) that are involved in fluorescence resonance energy transfer (FRET), whereby the acceptor dye quenches the emission of the reporter dye. In general, the fluorescence-labeled probes increase the specificity of amplicon quantification.

Real-time PCR that are used in some embodiments of the disclosed methods also include the use of one or more hybridization probes (i.e., detection probes), as determined by those skilled in the art, in view of this disclosure. By way of non-limiting example, such hybridization probes include but are not limited to one or more of those provided in the described methods. Exemplary probes, such as the HEX channel and/or FAM channel probes, are understood by one skilled in the art.

According to example embodiments, detection probes and primers are conveniently selected e.g., using an in silico analysis using primer design software and cross-referencing against the available nucleotide database of genes and genomes deposited at the National Center for Biotechnology Information (NCBI). Some additional guidelines may be used for selection of primers and/or probes in some embodiments. For example, in some embodiments, the primers and probes are selected such that they are close together, but not overlapping. In some embodiments, the primers may have the same (or close $T_M$) (e.g., between about 58° C. and about 60° C.). In some embodiments, the $T_M$ of the probe is approximately 10° C. higher than that selected for the $T_M$ of the primers. In some embodiments, the length of the probes and primers is selected to be between about 17 and 39 base pairs, etc. These and other guidelines are used in some instances by those skilled in the art in selecting appropriate primers and/or probes.

Probes for use in the methods of the present invention include but are not limited to the following exemplary probes listed in FIGS. 5B and 5C.

EXAMPLES

Example 1: Worldwide Literature Search

Figure 1B:
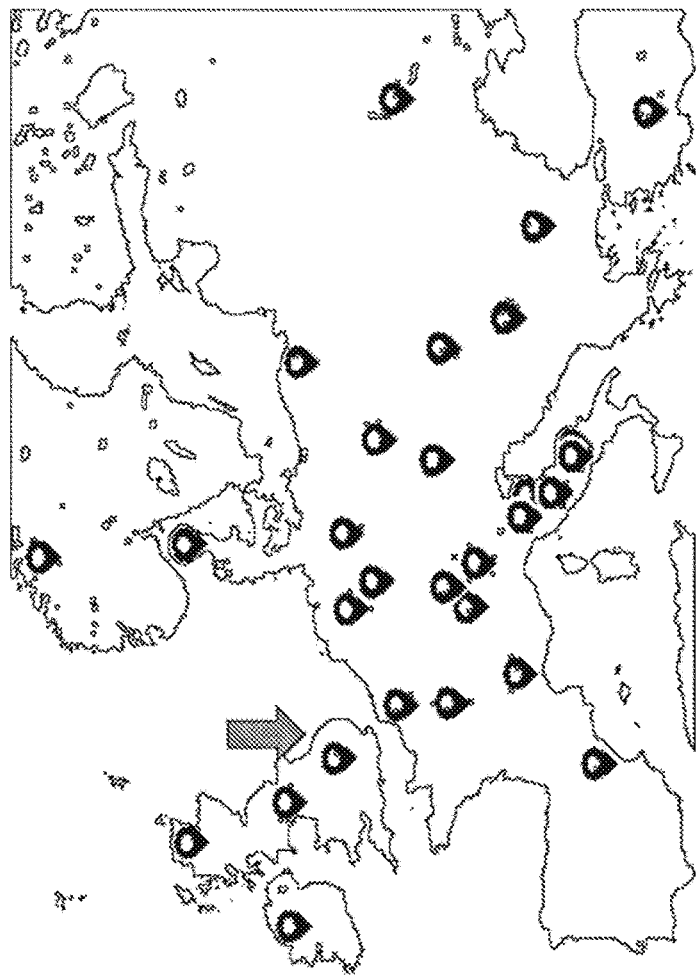
FIG. 1B illustrates a red arrow pointing at England as an example of the information contained in the bubble. The legend on the left shows the reported mutations, ethnicity and total case numbers for each reported mutation.

The HGMD database was interrogated and 62 different TGFBI mutations were found. The HGMD database was used to identify the papers in which these mutations were described in order to build up a picture of a worldwide distribution (FIGS. 1A and 1B). Each flag in the world map contains a summary of the mutations reported in a specific region or a country. The summary includes ethnicities, mutations and the total number of cases reported for each mutation (FIG. 1A). The mutations are spread with no significant differences in distribution in specific populations or geographical regions. Very few cases were reported from South America, and there were no case reports from Africa or Russia. The map can be used to extract country-specific information e.g. London indicated by a red arrow in FIG. 1B.

Globally, 75% of the TGFBI mutations reported in the over 1,600 cases consisted of one of the five mutations currently detected by the available genetic test. While reports of novel TGFBI mutations are likely to be published, the most common TGFBI mutations, found at codons R124 and R555, are conversely under-reported. Therefore, it is difficult to obtain an accurate estimation of the true worldwide detection rate of TGFBI dystrophies within the literature.

Based on the ranking of the highest reported case numbers from our study, the effect on TGFBI mutation detection rates by adding six mutations to the available genetic test panel was evaluated. The reported number of cases for each of the five most common mutations and the six additional mutations proposed for the expanded test are shown in the table of FIG. 3. It is noteworthy that the H626R is the fourth most prevalent mutation after R124L. This finding supports the inclusion of this mutation in an expanded panel for the diagnosis of TGFBI corneal dystrophy. Although only four cases of TGFBI corneal dystrophy associated with M502V have been reported within the literature (Supplementary Material), heterozygous mutation for M502V was detected in one sample. Therefore, it was included in the expanded panel.

Figure 2:
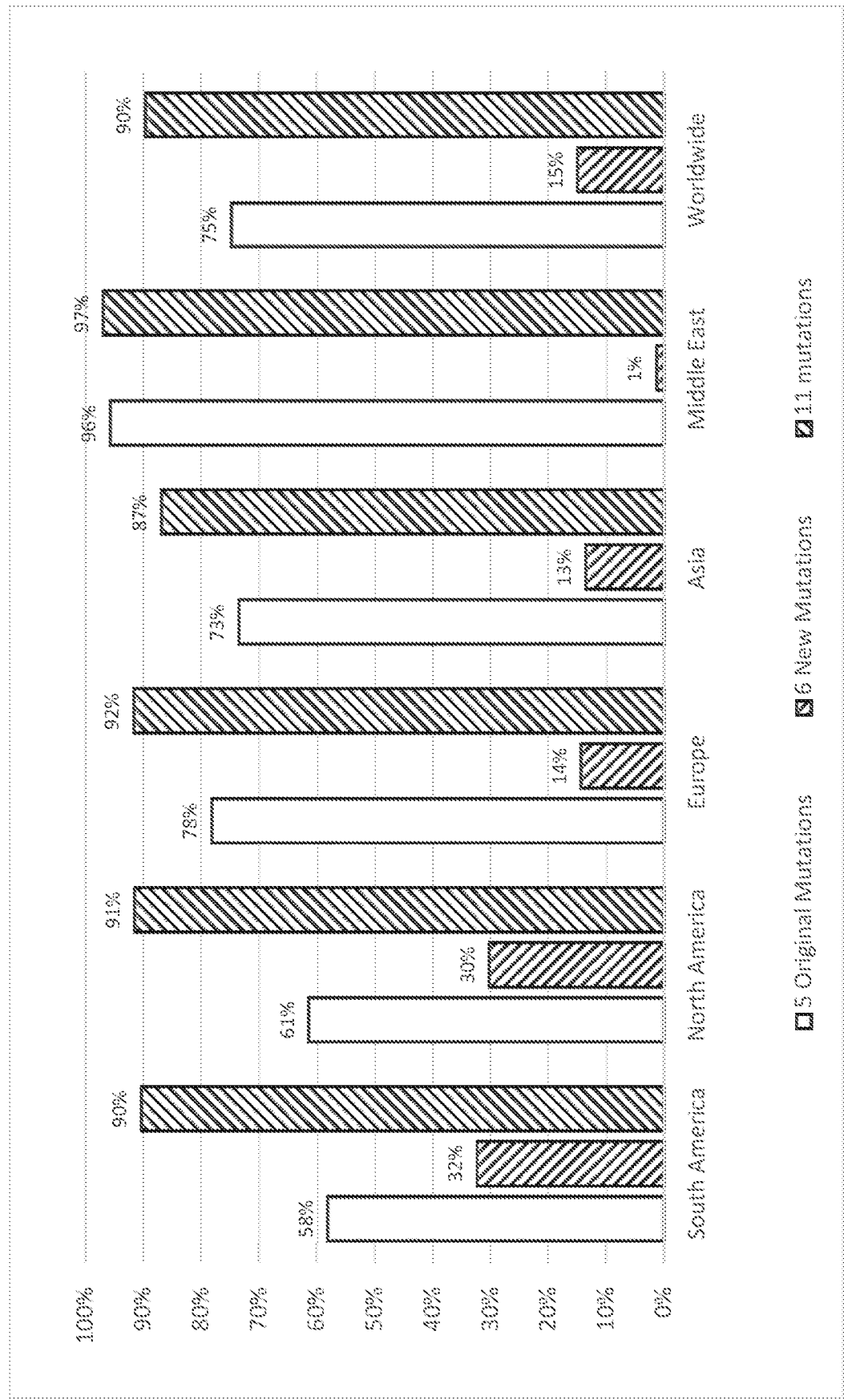
FIG. 2 provides comparison by geographic region. The original genetic test with five mutations, the six additional mutations and the proposed expanded 11 mutation panel were modeled in over 1,600 reported cases. The detection rate of the available genetic test with five mutations was very close between Europe and Asia.

From the cases reported in the literature, the addition of the six new mutations to the existing panel may increase the worldwide detection rate from 75% to 90% (FIG. 2). The addition of the additional mutations to the available genetic test would theoretically increase the detection rate by 32% in South America and 30% in North America. Europe and Asia, both with a 13% increase in detection rates would also benefit from the proposed eleven mutation panel (FIG. 2).

Example 2: Global Available Genetic Test Data Analysis

Since 2008, more than 600,000 samples worldwide were tested by the available genetic test; most of the samples were from Korea and Japan, where the test is used for pre-refractive surgery screening. An analysis of the global testing data demonstrated that the detection rate in Korea is approximately 15 in 10,000 people, which closely matches the reported prevalence of 1 in 870 people.[10] The detection rate of TGFBI mutations in Japan (3 in 10,000) was lower than that in Korea. In Korea, the test is administered as a general screening for all refractive surgery candidates, whereas in Japan, patients are first subjected to a rigorous clinical examination and only those patients who have no detected corneal abnormalities have samples submitted for the genetic test.

The clinics/hospitals in Korea and Japan use the genetic test for screening purposes as it forms part of the practice guidelines for refractive surgery. In the US, some clinics/hospitals use the test for screening during the pre-operative examination for vision corrective surgery, whereas others use it as a confirmation for clinical diagnosis or to exclude TGFBI mutations if the surgeon has any doubt about the imperfections noted in the patient's cornea. European clinics utilize the test mostly for this type of clinical confirmation.

Example 3: Assessment of an Expanded Panel with Six Additional Mutations

Few population studies like the 2016 UCL, Moorfield's Corneal Dystrophy Study have conducted Sanger sequencing on the entire TGFBI gene. This study provided us with a set of data on which to evaluate the addition of six new mutations sites to enhance the pick-up rate in a given population. In brief, the study consisted of 91 unrelated TGFBI corneal dystrophy cases in which 68 had a diagnosis of epithelial-stromal TGFBI associated dystrophy (RBCD, TBCD, LCD and GCD) and 23 had a diagnosis of bilateral epithelial basement membrane dystrophy (EBMD)[4]. For the UK population, a set of six TGFBI mutations were evaluated to determine whether these mutations in combination with the five mutations genetic test were appropriate. The data showed that the detection rate in the UK cohort would increase from 90% to 97% (Table in FIG. 4). Other candidate mutations may be considered, such as V625D and A620D from the table of FIG. 4, in order to increase the detection rate to almost 100%. This finding demonstrates that the inclusion of six additional mutations to the available genetic test, while improving the pick-up rate, will still miss some important mutations found in the UK population.

16 of the 19 samples with clinical indications that tested negative with the original genetic test were still negative (84.2% of the total), while three tested positive (15.7% of the total) with the expanded panel. The WES results of a mother and son pair with a clinical diagnosis of late-onset of LCD were positive for a heterozygous TGFBI H626R mutation. Parallel real-time PCR testing showed the same heterozygous H626R mutation. The third sample was discovered to be heterozygous for M502V. The result was confirmed with Sanger sequencing Subsequent patient history revealed that the patient had very small corneal scarring on the left cornea. There was no family history of corneal dystrophy or opacity.

Based on the evidence in the literature, adding six mutations to the available genetic test would increase the detection rate by 15%. This coincides with the 15.7% percent increase in detection for our sample cohort (3 of 19 samples). Geographic or population differences were not detected; therefore, the newly proposed six additional mutations are appropriate for worldwide use as an enhancement of the present genetic test. The new mutations would considerably improve the mutation detection rate.

The testing of 19 samples for the presence of the six additional mutations in the expanded panel proved that the expanded genetic test will have increased detectability of TGFBI mutations.

Example 4: Multiplexing Detection of Mutations

First, for each of mutations as shown in FIG. 5B, version 1 (V1) primers, a VIC labeled probe with a normal sequence, and a FAM labeled probe with a mutant sequence were combined to detect the mutation. Detection for each of R124S, A546D, H572R, G623D, H626R and M502V was successful. Second, for each of A546D, H572R, and G623D mutations as shown in FIG. 5B, V1 primers, a ABY labeled probe with a normal sequence, and a JUN labeled probe with a mutant sequence were combined to detect the mutation. Only the detection of G623D mutation was successful. Third, for each of R124S, H626R, and M502V mutations as shown in FIG. 5C, version 2 (V2) primers, a VIC labeled probe with a normal sequence, and a FAM labeled probe with a mutant sequence were combined to detect the mutation. Detection for only H626R was successful. Fourth, for each of A546D, H572R, and G623D mutations as shown in FIG. 5C, V2 primers, a ABY labeled probe with a normal sequence, and a JUN labeled probe with a mutant sequence were combined to detect the mutation. None of the mutations were detected properly. Fifth, in a single reaction mixture, primers and probes to detect different combinations of mutations were mixed.

The following PCR master mix volume calculation and PCT conditions were used:
TaqPath ProAmp Master Mix volume; 2.5 uL per test
M502V V1 primer forward and reverse primer, and VIC and FAM probe mix volume; 0.05 uL per test
G623D 20 pM V1 primer forward and reverse primer volume: 0.05 uL per test
G623D 50 pM V1 ABY probe volume: 0.025 uL per test
G623D 50 pM V1 JUN probe volume: 0.025 uL per test
Water volume: 2.35 uL per test
PCR fluorescent detection amplification cycling number and condition:
Cycle number: 40 cycles Cycling conditions;
   Pre-PCR Read (Holding State): 60.0° C.—01:00 minute
   Holding Stage: 95.0° C.—00:20 minute
   Cycling State: 40 cycles, 95.0° C.—00:30 minute
   Post-PCR Read (Holding Stage): 60.0° C.—01:00 minute Out of the primers and probes for different combinations of mutations in a single reaction mixture, only the V1 M502V primers and VIC and FAM probes with the V1 G623D primers and ABY and JUN probes successfully detected both mutations in a single reaction mixture as shown in FIGS. 6A and 6B. The combination of reagents for R124S and A546D, H626R and H572R failed to detect the mutations properly.

The following shows GRCh38.p7 *Homo sapiens* transforming growth factor beta induced (TGFBI), RefSeqGene on chromosome 5, NCBI Reference Sequence: NG_012646.1 (SEQ ID NO: 61).

```
   1   agagggaaca gaagcatcta ggagagattt ggaaagaaca cctgcaggat cttggtgact
  61   gattgcacgt gggggaccag agagcaggga caggcaaaac tgaatgcaag gtttccaacc
 121   ttgagcggca ccacaggcaa gaatgaagaa atgaagaagg ggagctggac gaaagagcca
 181   agggatttct gcattttgga atgaattgct gctgggtggt gtccatttcc ctgaaggcct
 241   ttatcctacg tgcaagaaaa ctcgtgggaa gcagaggaaa ggcatgtgta agccaacaat
 301   catctgtggg catccttcca ctaaagtatt tgaggtcagg caactaaagc aacctcaaaa
 361   gtgcctctgg attcttctta gatattttag ctgagccaaa tcaatgaaac tctcatgaaa
 421   aatcggtttc cctggaaaat gaaattgggt tctaaccaac aagtagcatt tggcaggccc
 481   tgattaagaa agccagtgtt tggagaagtt gtgaaaacag ccaagtcatt taagaaacta
 541   aacactgggg cctaatgcca ttctagggct gcgacggctg ttctgttccc atcaattgca
 601   gagcccgaag cctcaagttt gttttaagtt cctgccatta caaacctgtc gattatccca
 661   gcctcccttg cgggctttga aaagagagaa gaatggaagg tgactgtggc caatttcccc
 721   tccctgtcca gtgtgtggaa gacactgaat atgcaactac tgaccttgtg cctgggcatc
 781   ttgaaggtct tccacaaagt gagctgggcc tcagcggaag atgagagttc ctctgtggtc
 841   acttcactgg tacacatttt caggtgtatt tcgtttcttc catgcctaca taaattgaat
 901   cctctgttaa ccacctctga gctcatagct atttaacatg accctgtagt cctgtgcata
 961   caaatcacct tgggatctgg tgaaaatgca gattcagtgg gtcttgggag gttgggaggt
1021   tataagattc cacgtttctt catgagagct agaaaaaata aataaataaa taaaaaattt
1081   ttaaattttc cacatttcta atgaactctg gggttgtgct gatgatgctg ttttgcagat
1141   cacattttga gtggcaagac tgtggaaaat ccttgagaaa tcaatccaaa atcccctaaa
1201   tggtactaca atcacacctt aatgttagta aactgagatg tttcttacct ttatttgtaa
1261   catggaaaaa acaattactg tatatgaagt accattctaa gttctgtgtg ttacacaagg
1321   gatggcaatt ttccccaaaa tttgattcac atctttcat ttggatatct cttgccaaaa
1381   ctcacctttt tttctcccta gcaagtcttg gggagctgaa ttttaagagc tctttattta
1441   gctatatggt ggcctctgaa aatgattttg actgtatctt ctgtctccat gtatgcccaa
1501   gcatcaccag gaactttagg gagtaaggaa aaggcaggcc tggtgtcagc tgggctgcag
1561   atgccagctc tcccaccaac aggcccagaa ccagtttctt tcctaggttc ctttgtgaag
1621   aacttgttgg aactactaat ttatcatgat gcataaagct tgttgtcata ccctacagta
1681   ttattttcaa aacctgaatg ttttggtga ccttcatgt gccacaaaat gtaaaagcag
1741   tcattttta aaaagtgctt gaaaaagtct agtaaagatt cttccaagca agcctcactt
```

-continued

```
1801  tctcctgttt agattgttta atctggaagg aaaaaattct ttctcaaatg acagggtttc
1861  tggtgctctg tgtttgcctg gttggctctg ggtcatctgg ggatggaggg tccctgctct
1921  tacctccagc agcatcactc ttgtctccaa agaagcagca acctcaggtg ggagaatggt
1981  tatactcaca gcattctgct tttcatgttt gaaagagggg atgggtggtg gggcatggat
2041  gtgggatttt aaaaaaatat ctaaaccata aataaagtat tactgcaatc tctttactga
2101  gctcatggaa aaactcaagt catcgaatgt tagttttgca gactggaaa gtgaggtcca
2161  gtgaacttgc ttgacttgcc ctaaatcttg ctagagagag agctggaacc agatggcagg
2221  gctcctggcc tcttacatac aaggagcatt tttcctagaa actgcaatgc agccaaattc
2281  tactggtctc aggggaaact tgttctggga gtcagcctga gcttgaatcc ctttgggttc
2341  ttcccattat cctatgccaa gcagtcatgc tgaaaccgag aaatgttttc ctttcaataa
2401  atgaaatgag cattttcaga taattatttc tgtagttgct caaaactatc atattgtttc
2461  attgaaccct actatataga acaatgactg gggagaggta ataataataa tagcaatgca
2521  tatttattgg ccattttact tgaattgtat catgtaatct agtttagagt cctgtgaggt
2581  aggttttatt atcctctcta tgaggttgaa taacttgccc aagaccacac agctaggaag
2641  tagaaagact ggtatttgaa cccatcttct ccttttcttc tccttcctcc tcctcctctc
2701  ttccaacacc tgctcccaag gaagctcatc cagtgcatga ctttagctac cacctgctcg
2761  tagtggtgac tcaaatctgc atctccaatc ctcataccta tcctgagctc aagacctttg
2821  aatatagctc cctcctgtcc atccctcctg gaaatgcagg tggcttgttc acacataatg
2881  tgaacacaaa tggagcactc tcctcacaca cccaaatgtg caccttcacc agcgtgccca
2941  gcacaggcat cccttcctgc cagctatgag cctcgaggtt agctctactc cccctcccta
3001  accctgcatg cccaaggggt ttccaagtct aatcaatgct accactaaaa tctcccatac
3061  acctgttccc tcctctccac tagcttgatc actccccatg caggccctca gttgctttat
3121  gctctcagta ggccctcctc cagtgcccac actctctccc ttctccttcc caccttcttt
3181  ctaccagagt tctaacctct ccagcccccg cttgtctttt tctttccctg gctgccatcc
3241  taactcgccc cttcccttct cagacaagct tctacatgct actcatctct ccatcaaacc
3301  accatattcg ggctttggcc atctgctctc cacagccaag tccccagtgg cctctctgct
3361  tctgacacag tgaaagccat tcagatctgt cttgttggca gcattcctca ctttgagcag
3421  cgccctccta ctaggatacc cctccttgac tacaaccccca cattctctac ttcctgggct
3481  cttctgtcac tggaggatga ctcccaggtg tgaatcttca tcccgcgtcc ctcactcaag
3541  cccccgatcc tcatatccag ctttatcctc atgggatgct tcaccaggat gagtcataag
3601  cacctcagac tcagggtgtc ccaaaccact catctacctg gcaagcctgc actctgcatg
3661  tgcctcattc tgaacatggc accatcacct gctgcaatgt ccagaccaca acaccctac
3721  aatatccttg actctccttt ctccccttct ccctgtatac agactccaaa ttctattgag
3781  actattacct cctacacccc tcacatttgc ccagccttcc ccatctctgc ctctaccacc
3841  atagttcaag ctctcccatg gtccttcct ggttacctgt tcttcttgcc tccttaagcc
3901  tctcatgaca ctggccatgt cacttgcctc cacccatcac ccgctaggct cttagctgga
3961  gtctgggccc tgctaccttc ctcccttct tccctaccct tgactccacc tccctgtgct
4021  tcagccaacc agataacttg agtttcgtga atgcatgcct cagtttacct gattaactca
4081  ttttcatctt tcaggcctca gagcaggtat caccctgtca gggccaggtg cctcttctta
4141  gctcccaaag ccccagctac tcttcatgga acatcattgg cttgggctac ggatcttccc
```

-continued

```
4201  aaattggagc tttttcacaa agggcttagg tctcactcat tctattaatc catctgtgtc
4261  tccccagggc tagcagtgcc aagtaactga caggtgatta atagatgctt gggtaagtat
4321  cacctctttta ccatgtgaca atttgtttac ctgccttgag ctcctccagg gcaggactct
4381  tgcctttgca gaatctatct ggcaggtact gttgcagaga tgtttactga agaagggaat
4441  gaattagtac caaggtgagg accccaccct tccccacggg ctccaaaagc agcttagagc
4501  ccaacaaaac ctgccccaca ttttggcgt ttctgtggat cacacgattt actcatctgt
4561  ctttcaatga gcatgacagg tggggtgggg gtggagggat tagagattga ggagctgggg
4621  agggtggtca gctcctgggg tgcagaaaca agtctgatgg gccatggtgt tctgggaatc
4681  agcactgcct cccctcaccc ctccctgcag tgttttgtag cctcaagatc agtgagggaa
4741  tcttcgggcc cccagcatgc aggaccgaag cccccgagac agctgtccct cagtcccaag
4801  gtccccattt ggaagcagcc acaggaggcc taagggacct ataccctttgg tttgaggaag
4861  actgtggcga gggagagagg gagggagggc tggcagtgag ggcaagggct gggaaaactg
4921  agcacgggca cagtgcggga gcgggtgggt gcccagggca gccaggggcg cacgggttgg
4981  gaggcgccag gcggcccgcc ctccttgcac gggccggccc agcttccccg cccctggcgt
5041  ccgctccctc ccgctcgcag cttacttaac ctggcccggg cggcggaggc gctctcactt
5101  ccctggagcc gcccgcttgc ccgtcggtcg ctagctcgct cggtgcgcgt cgtcccgctc
5161  catggcgctc ttcgtgcggc tgctggctct cgcccggct ctggccctgg gcccgccgc
5221  gaccctggcg gtcccgcca agtcgcccta ccagctggtg ctgcagcaca gcaggctccg
5281  gggccgccag cacgggtaag ccgagccgcc tggccagggg ctgcggaagg tcaggtagtc
5341  ggggctcgga gcgcaagccg ctgggggcat tgaactgggc tggggcgca ggggacaaag
5401  cccgaactaa aaaccttgca gcatggagcg ctcggacacc agccctgcac gcggtggaag
5461  gagagaggga gggaggtgga ggaccatgga gggaaagcgg gaggccgccg ctttgtagaa
5521  gggagtgggg aagtggacca gagactttcg acgcaggcca agagcctgag acggacagcg
5581  ctttcagctt ctcctcccag ccactgcaga aagggggaaa tggcaactct ttggccataa
5641  tcaccgtggg agggtgccaa gggcaaagcc cacccagcag tacacctatt ccaacccagc
5701  caggcccccg ccagcgact ccagacaaga acctgggcca cacacggtgg cagcatctaa
5761  ggtgccccag gctcctgtgc tcctggccag gccctgcact cagacactgc tggcacccga
5821  cactgctctc tgggtacagc aagggcaatg tggcacttct tgtcctgccc gatgaagagc
5881  aggagaatgc actgggccct cacacacact gttcaaatgg ggaaactgag tcctgagtgg
5941  ttccactttc ccacagtcct gaagtgtgca ctggagccag gattggagtc tgtcttaaag
6001  taatagctgg gtttgtaaat gtaggacact atcattgcag gaattccttt gagaccctga
6061  agatgtgttg gctttaggag acaaactcaa gcagaaggtc tggtctgata gtggccctaa
6121  tactgaccca ggcagaggca ggcaacattt ctacctcaaa aaccaggcca tacctgcgtc
6181  acaaataccc aggctttgct gcagcttcca gcctacctgg ttgcaccaac ttctttttca
6241  taactaggta aaactatata tgagtagaat cttgtagtga ctcctcagag gaagcctaaa
6301  taccatcggg gtctggcgtt cacacccaca agcaatgccc aaacctccaa gagactgggc
6361  agatctgtgc tcaaatcaaa actcattgtt gggggtgata gagttgactt cacaggccct
6421  gaaagtcttg gctccttgca ctaggagtgc tctgggtacg gtacaggct gccccttgta
6481  gggcatagtt gctcttgttt cctctacttg tggctttatg gtctaggcct ttcaggagtt
6541  tggggctctg gcggagaggg cctgctggga gcatctggg ccaccctgca gagtgaaatc
6601  aaaccaggcc tggctgcaac ctcaacaccc tcctggaaag aggagaatac tggggatatc
```

-continued

```
6661   ctggggtctt tctggaagtg ggagaatcag ctttgacttg ggcagtgtgc agaatagagt 6721   gagggggat gtcagaaaga tgagagggat atgaggcctc aacatcaaaa tgcaagcacc 6781   tggcattttt attatctctg cccacctctc cgttggtctc tctgcctttc tgccaatga 6841   attgtgttat gtttgggtgc ctcaatttgc ctaggagggt tctatttctt ctgtatcttc 6901   gccactaagt caggagaaga tccttatagc atgccctgca acagtgtcac ctgtaagggc 6961   atctctctgc acagccacag tgaaggatcc tcaaaggtat tgagggcttt ccatcaagag 7021   ccatctttac agcaaacctc tttcccttca gagcccagaa gagtgctgac cagctggaaa 7081   acagggtttt tttcttaaat gcagatgctc ttgattatga gttccagata ttagatcaac 7141   ttccccacca taccctgca ggcaaagcct cttaattagc ttcctgcagc acagctggaa 7201   aggcctattg taatctgtga tgggcagagt aatctaagaa gtcacaggag caccctgtc 7261   ccagtagaat ctggatgcgc aggcacatga accatggcaa atggttgca ggcacagttg 7321   tatttactct gatctaactg tccctgttaa tgccacaggg ctgcctggcc tggcacacag 7381   ggctgtggcg ccttgtgcaa atggataacg ttgttctagc tccagccttt cattcaaagt 7441   gaaaactgtt agaaagggaa ggaaaacttt gctattttaa ggaattgtag cgtgctgcct 7501   gatatgaagg aagaaataac agctgtgcct tgcttgtgcg cagcactcga ttgccgcttt 7561   tgctttcgac ctcaccacaa cacagtgaga tctactgttc atgttcccat tttacaggag 7621   gtgaaactgc agcttagtga ggtagagagt gacttagttc agacacagaa tgctgttggg 7681   agagtaataa ctatgatatg gtctcttgac tcccagctat atctgtgttg ctatagggaa 7741   ggggaaaaat aatactgaaa gagaagtaaa aatacaatca cacttccaaa catcaaccac 7801   caaaaactga actgaattc ctgaagcact tggttttcaa atctaagctg aacatcaatg 7861   ctgttattct tgaggcccag aagcaacttg ctcatttcaa ttaagcttca gcatgaactt 7921   cctatgtaca cagcccaccc acactcccg atgtgagaag gagagggtca cagccgcccc 7981   cagcctctgc tgctgccaca aggacagcag cagtggaaac attcagcaaa ggaatgttgg 8041   agccacatcc acaagagact cactgaagat tcgccaaacg cctacgaaa gtggcaggga 8101   attcattgac agtaattgtt tcctgcttga tcagattgaa gagcttctgg gattctgtaa 8161   caataaatag daccgggggc tggagtatgg ccagcaagga ctcttcaggg gttattcagg 8221   gactgtctaa cctgtgaatc ctaggcagca aacagaaacc aggtattcag aaatctggag 8281   gatttggtca ggcccagcta ggactaggga ggcatgggcc tctgctggct gtggtcccctt 8341   ctccagcctt cacttctctt gtccctagat ccttacatgg attcattaat gctcattgtc 8401   cctcctgggc ccactcactt tcacctgttg aacaaaaaac tggccaagag gtgacagtca 8461   tatcaccgca gaagagacag ggcagagaaa tgaaggggca gaatggactc ccacccaaaa 8521   gcctgactct gaatatttga gaattgttca agttcctgca gaggaatcat gatggggaca 8581   gtaggtgtag ttttactgc aatattggtg tcttcttaac aaatacgctg cacatcaagt 8641   gatgtctgtg gatggcattc ttaaagtaac agggaaattg atgttaaaga aatacttcat 8701   ccttttgggtg atacctgaag ttctctgagc ttggaggtct tgtgaaagcc ctcagtattg 8761   tttgttttat ttgctttcct ctgacttgtg attcagtcag atgcatgcct gcctctggct 8821   caggaagatc aaccctctcc tgactgacca cgcctctcct gactgaccac gtagcacagc 8881   agcttccttt ccctagggc tcctaatgaa gctttcacaa tcacctggcc tgagcacagt 8941   ttgggtcagg acttggtata cttgaaaaa acatgcaaaa ccaaaatcct gtggttctgg 9001   aaaaggcttc ttagcagaac ccccagacat ttacactctg ctttttcaca gggtccctga
```

-continued

```
9061   ggattctttg gatctgggta gtttggggag cagtattttc aacaagttca tttcgtgctc
9121   cttctacacc ctgcctggat gctaggcccc atctagaatg tgaacaacag aacaaggcag
9181   aacacttgtc ctcaaggttc tgttgagtgt tagatgcaga gaagagacac cccccacctc
9241   cccgcatcac ttacaggaat tctgtttgga acccaacatc aaataaggac cgtatccact
9301   gtcagaggat gggaagcagc atgtcatctg ggacattgga gaaaggctcc tgggggaagt
9361   gggacttgag ctgtgatcta agtaatgaac aactgagagt taaatgggag agcatcccct
9421   atcagggtcc tgagagcaac cagccatggt ttaaaccagc tataaagcct cgggtttata
9481   ggatagacag taacaatggc ttgtctttgg gagccaagca gctggtccag gcatgcagag
9541   catgtctgta tggagagctg cctgagagat gcttttgttt acacttatca attgcccatg
9601   tcaaagaagg atatgtacat gaagttacat cagtatgtaa gagagatttt aacaattttt
9661   gcagggaag cttcatggg ggctgatggg aatctaggta aacagaacca aagtctaaac
9721   ccaagatatc cccagtacca agactgaaat gactctctcc tctatctcta gaaagttcca
9781   gtgacccaag gaggcaaaca cgatgggagt cattaaagtg gggtggacgt gctgatcatc
9841   ttcctaattc tgctgctttt gttttcagcc ccaacgtgtg tgctgtgcag aaggttattg
9901   gcactaatag gaagtacttc accaactgca agcagtggta ccaaaggaaa atctgtggca
9961   aatcaacgtg agtatctgta accagccagg agaccaagct gtatgcacgc tggctgcagt
10021  tccccagggc ctgggccagc cttctagaag gtcaggttgc ctaaaaagcc atgaagatgc
10081  atgtgcgaac atgtctggga cctgcgtgct agggagtggc attttagga agctggccaa
10141  ttttgttttg cattttaag gctgctgaca agacttggag acatttttca gggctggttt
10201  gggtttgcaa gaaacatgaa acactgcgtg tgtgtgtgtg tgtgtgtgtt tctcaatcct
10261  cataaaataa tacagatatg cagtggagaa gccaccagca tgtgactctg gaaaagaaag
10321  cccattggtg aatctgtact aaagaatgcc atccctatct tacagtccta aggtaaacac
10381  cccaaaaaga cttagagcac taaacatatg cagattatga gacagcatag catataatat
10441  ttgcacagac ttcctcattc aaaccctagc tctacctggg ccagtcgatt catctttaga
10501  accctccatt gctttacctg aaaagttcgt ataacaaaag gacccacctt atggggttgt
10561  tacaaggatt gaatgaaata atgtacataa gagactgaat atggtgccca gcatatatca
10621  gtgctcaata aatgctagct actattatta ttatcaccct agatttgcaa atctagacca
10681  cacaagcaga agtaagagtg ccaacggggt gtggaccagt gtggttacaa tagggcttgt
10741  tgatgtctgt ttcagcaagg agggaggcag cttttacccc actgcccagc tccctggtgg
10801  aatcaggtgc atgttctaac aattctgggg aaacctaatc tgttttggca ctgtcaacag
10861  atctcaaagc tggctgtctc ctatagctag gaagatgtgt atgacaaatc tcctgagcca
10921  cttgtgaagg cctgaccttc ctcctgtctc catacataat gggatgatta agaaactcta
10981  agccactctc ttaagcactt ttcaatgtta gggattttta agtttattgt tgtgacattg
11041  cttttgagca gacatctcct ccaatttaat agccaactga agaagagaa atgctcttt
11101  ccttaaactg tatgtggaaa taaatattcc aatgtgtgac cctgattatg ttaggcaatt
11161  agcaatccta atatgaattg agggaagttg ggattcatgg cacagctggg agataccag
11221  cagtccctgg gagcctgtcc agggcaggtc catggcagct tgctccatgc ctgattgaca
11281  gcccagcctg caagctaaaa gttgagtgag ctaggaggac acactgccaa gattcagcta
11341  acagacaccc agcgatattc ttgctgctat gaacaaaagg agactatgca aattatacac
11401  cacccattct tccaggatgc ctgacttaaa aaataagaaa aaagatgggc cgggcacagt
11461  ggctcacgcc tgtaatccca acactttggg aggccgaggt gggcggatca caaggtcagg
```

-continued

```
11521  agacagagac catcctggct aacatggtga aaccccgtct ctactaaaaa aatacaaaaa
11581  tattagcggg cgtggtggcg ggcacctgta gtcccagcta ctcgggaggc tgaggcagga
11641  gaatggcgtg aacctgggag gcggagcttg cagtgagcca agatcgtgcc actgcagtcc
11701  agcctgggtg acagagtgag acaccgtctc aaaaaaaaaa aaaaaaaaag aaaagaaaac
11761  ctttagtact gattgatttt ttcccatgtg tgtatattat ctactcaaat taacaattaa
11821  ttacttaatt aaacacaaag ccaggcctca cctaattgct tcttggaagg tgaccagagt
11881  gctagtgcca agcaaacaac tcttctatat ctcaagagcc ctgggcttca gagggccatc
11941  tttttgtta attcaagttt ctctgaaaat ggagacccgt ttatgatgac aagctggcta
12001  cagggtagca tctgccacac tgtttcgggg gtgccgctgg gctgaagcat ttgcccagct
12061  agttaacaat agctcgataa cattccctat cagtgtccag gctgagaata ctgtcagtga
12121  tgagtcgcct tggctcttgt acctgtatct ttgtgtgcca ggacaaggca caagcaacag
12181  agctgtgtgt tgccaaaatg ttcctgatga gcaggtcaac ccctcggggg caggtttgga
12241  tatgataatg tggtgatgtg gtggcgcagc tcccttaccc agtgagcaca aggggagtcc
12301  tctaggaaaa ggaagaaatg tctggatgag gtggggagat ggggttcaga gtggactcag
12361  gcaaagcccg atgcccagtc ccagctgttg gcctagtctc acaaagccag aaggatatga
12421  catttacatt caactcttga atttgtggcc actgctttgg gcaacttcaa agagagaaaa
12481  tgaagataga aaatattat ttgatataaa acttctagga caagagaggc ccttcctgga
12541  acattacatg tagtattagg aaggtggagc tgccctggaa aagatccaga gaactcagag
12601  agaggaagag gtggaaccca tctctgttct tgtagagagc tcagtaagag tggcttggca
12661  gggctcctgt gtacctgaga ccaagaccag tgaggaggct actgtctgac caccatacgg
12721  tcagaattca gtgccatggg tggtcaggtg ggaaggggag aggactgtgc tggctggagt
12781  tgatgttatc ctggggaaag taggtcccta gatgccttta gttgagtgag gagcagactg
12841  ggaaatggga gcacagtagt ggttgggca aaaaggactg tctctgcatg aggtccatag
12901  gcagttggaa ttttctcagc aagactccag agaaggaggc tggagcagag gtgtatgttg
12961  ggatgaaaag gagtaaagta tcatggggga ggaggcagct caggttgtca agggtcaaga
13021  aaccagaagg agaatttcac cttggaagca gacaacgggt accaagcata caggggaata
13081  ctttgtggtg agaggtcaca cagagataca ggagccgacc tggtgagaca ggagcctgga
13141  gccacctgcc tgcttttgtg aggccccaga ctccactgct atcatcaggt gaagctctgt
13201  tgcctgcaca caaaagcttt tctgcattta caaagagaga agggcctgag tttctggtgc
13261  aatgcgtcaa gctgacatat ggactttatt acaggaagtg gttaccagtg ggtccctatt
13321  tagtggctgt tattgtgaat tttattgttc ggaaattcac tttagcattt atttcagatc
13381  ctaaatagca ccggagtgat acaatggcta atcaaacaaa gagggctgtg gggagcagac
13441  agtcagcatc cccctctgtg atttcaggcc ctggtttgat tagtagccat aaaattttt
13501  acgtgtggca ctttgagcaa aggtgcagga aattgtggtc aggaagcctg gctgcctctc
13561  gacaggcttc ctttgtgcta gccccaggga gaggaggcct atttaacagc caagtccaag
13621  ttgacatcat gggactggaa tagtcatagc aggagctcag acatcataaa cgtggcatag
13681  ggagggctgg tggaggagct agcgggtatg ggtggcagct attcattcca aaagtcttga
13741  aattgtttca cgagcaacac atttcacaag tgcgaagccc ttctctggag ccaagatgag
13801  ctggcagagc actcctgttt ctctagtagc aagtgttcct ttgcccaggg gcaaaaatat
13861  taatactcct tcagcactgc attaatgctt aaagatttaa cttttaaaga gatcagctgg
```

-continued

```
13921  tgcatggtcg agcttttcca tcagctggca gggcttttc  agtaggtgtc cttctgggca
13981  gggcactggg gacagctgac gtgaaggtga agaagagctg tcgttttcct cccttatatc
14041  ccacaacctt ggtcccaaga ggaaaaaaaa gaagatggtg agaagtcatc caagcagacc
14101  ccagacccat actagtgcct cctttcctgt ttcatatccc tgtgcagcca gctgggatct
14161  cttgaataat ctgctctggg ggcactgaga ttggacatac accaaacagc ggagatcgac
14221  caaacgcctc tgttgggcag tgtttcctga gggttctgtc ccattctgta aactaggagg
14281  ctgactagct gacaaggaat tttattctgt tgggtattta catgaaccta tgtgccacct
14341  ggggtaagac cctgtggtag gtagaaacat gacttcccaa aaatgtccac atcctaatct
14401  ctaattctgt aaatatattc ccttactgga aaagagact  ttgcaggtgt gattaaatta
14461  aggatcataa gagggagaga ttatccagga ttatttgatg agtctaatat aatcatcagg
14521  gtacttaaaa gagggaggca ggctgtgcct ggtggttcac gcctttaatc ccagcacttt
14581  gggagactga ggcgagcggg tcacgaggac aggagttgga gaccagcctg accaacatgg
14641  tgaaactccc cctctagtaa aaaaaaaat  acaaaaatta gccaggcatg gtggtacaca
14701  cctgtaatcc cagctactca ggaggctgag gcgggagaat tgcttgaacc caggaggcag
14761  aggttgtggt gagctgagat cgcaccactg ccctccagcc tgggcaacag agcaagactc
14821  catctcaaaa aaaaaaaaag agggaggcag tgggatcaga gtcagagaag gcaacgtgat
14881  gatgaaagct gacatttgag tgatgcaacc acaagccaag gaatgcaggc agcttctcaa
14941  agctggaaag gacgagcaat ggattcttcc ctacagcctc tgtgaggaat gcagcctttg
15001  attttaaccc cataaggccg atttctgact ctagcctctg gaattgtaag ataatttgca
15061  tgatctcaag ccactaaatt tgtggtaatt tgtcacagaa agcaatggga agccaacaca
15121  ggcctatttt gttgacttat agatgcattt ttctttattt caatgtactt ttatcaatgg
15181  tctcatgtag ggtattgctt tcaatgaaga tattaacata gtttcaactt taaggtttat
15241  atctggagtt tctttagaag cttcacaact gaccacttag taaacagtaa gcatctgtta
15301  agtgcttctc atatgtaagt tcattcaatt ctcacaatca cactataaga taaatatgat
15361  tattagccca tttacagatg aggagacagg ctcaaaagac tttatgcaa  cctggtcaaa
15421  gtcattcact ggtaagctga ggaggtctgt ccacttcctt ttgctgcccc caggggtat
15481  caagcctggc agttagtgtc agcgacttag gaggtgaaca agtgagcagg cctgtaggac
15541  ctggctaaac tgcccaggt  ctctgtctac agcctcaaac ctgtggctgt gggtcccaga
15601  gacaaggcct cctcagcatc agagaaggat gcctttgtct cagggtcatc aaccttctcc
15661  aggttgctca ccccctgctg taaagggat  ccccaagacc gctcatcaga caaggagctt
15721  gggaactgag gagacacagt cagcctccag gagtgcccaa aatgccctca catgctgcat
15781  acagattgcc acaaataaag tacatccaca ttctgaagac tctgtcctca tcaccaacca
15841  ggctggcccc tggtgagggc tgtagtggtt gaggcctttg ttggtagaca gtaggttaaa
15901  gcaagccatg attttctatt gggaggcttc agaatcagct cagctgtgtt ccaagacca
15961  ggagggcaga aagcaaacca tcccaggcaa gcagtccatg ggccatgtca gatgtctaga
16021  cgttatgggt ctgtgtttgc tctgccattc ctctcggaaa ctatgatgcc ctgtatggtt
16081  taccttcagt cacaggtgac tggcctacag ggccattcct tgttccaacg acttctcgag
16141  tataattaat ccccaggcat ttacggccag agcagccggc caaatccgtg aagtgcagtg
16201  gttgttttaa attatattaa cttcttggaa acttatttta gggagagaaa actcagtact
16261  tctctctatc caatcttgag taaaatgtt  agaagggact ggtggagagc ctcccagaca
16321  tccctacaca tagactttgg gttgacatta tctctttgca ccttccttga aactttcttc
```

-continued

```
16381   taaattaggt gccttccctc atttaggcac cttcccagta ctagtctgtg acctgttagg
16441   aaccaggcca cacagcagga gttgagtggc agggagtgag cattattgcc tgagctccgc
16501   ctcctgtcag atcagcagtg gcattagatt ctcatagcag tccgaatact attgtgaact
16561   gtgcgtgtaa gggatctagc ttgtgcattc cttatgagaa tctaatgccc gatggtctga
16621   gatggaagag tttcatacca aaccacccc ttcccctgc caccatctgg ggaaatattg
16681   tctaccacga aactgatccc tggtgccaaa aaggttgggg accgctgtcc taagggatct
16741   gcttttctg acctgaggtt tttcttatt agactgtatc tggctgagga aagcctgaa
16801   gcctttaatc ggaacagctt tggctgatga gattagattc agaaaccaac agattggtct
16861   tttctatgca gggaagccta ggaactgggg ggctatggct gggaagcccc ctattgtttc
16921   catcctttcc tatgttcatc ctggaggaat ggcatcagac ccatgcctct gtgattgctc
16981   ccagcccatc aaccacagc atctatgttc tgcctgggac cagggccagg gagcatggca
17041   cactgagctg agtataagga gagtggagca ggccactgcc agcccagaaa attttggtca
17101   aagttgcctg aaatcttctc agccttcgat tcacagctgc tctctgctgc tctgggcca
17161   tgcagaccag ttcagaaaag agttaatttg ttggggcagt tggaggcagg tggactgcca
17221   gctttgacac cttcccagcc cacaggctgc tgcactgggg ctgaaggcgt ggctaacccc
17281   tgcacaccta gagagtgaca gagatgccag actgggcagc aggaaggcaa gaggattaag
17341   agagagcttc ctggctgaaa gccacactcg gttaaccagg aaaaagccct tggcacgaga
17401   agactcagtg gcctgaggga ctgagccttg gttgttgggc atgtgctgca taagccatcc
17461   atgtgtgaca gtagagtgta gtccagccac tgtgggacat gggtgctgaa agaccacatg
17521   gagaggaaca gtgagtgctg acaagggcta gccttgatca ctttgggagac accccctgtg
17581   tcttctagat gtcagactt ccaaatctgt ctgctatcct ccaaacgtgc attttcaaga
17641   gcaatggaaa aaggattgga cttgatggaa tgcagcaaga gtcctaggtc tgttactacc
17701   tacctatgac cttaagaaac tccttcaccc ctcagaaccc ttacagcttt ctttctgatt
17761   ctatcctgag ttactctact ccaagctgag acttttctgc ttagatctat cccttcctcc
17821   taaacccca acctccattt ctcctggtgt ctttctttac acacccctca gcatacacac
17881   acacctagcc acaggaacca atgagttaat atttgaggag ttggttttct tttgtcctca
17941   atgagatcct ggtgaggcca cttgagctgt tcagctccct tgcggtattt tggggatgga
18001   actcagaagc caacaatata gaaaagagt ctttggccag ctttcccagg ggctccatgc
18061   catagagagt actgcacccg tgtgcacagg gggccctgac atgaggactt tgaggataac
18121   actattcctc caactctgct tcagcatctc catggatttt cacacagaca ctttaggaaa
18181   gaaactaagt ttgggggac ttgacctaat cccacatcac agccccagta atacagccct
18241   ggaatttatc acagaaagcc tagaatccca tgcatatccc atgcatatgc atccctagtc
18301   ctatgggttc aaggcttgga gctctccctg gatttagctg ggaaaagttg cagacagtt
18361   cttctctgtc ttctagaaat atggactaga atcgtgagtg tgagattgca agtaactttt
18421   aaaatcatct agtttaactt caccccattt catagaccaa gaaactgaga ccagagagag
18481   aaatggactt tcaagttcac cctgctagtt actgatggat cacaagtcaa atctcctgat
18541   tctagcactg tttctcttac accacaccac ctttgaaagt gtgtcaatca aatcttactt
18601   tagttgcaga ggatgacttt agtttctgaa gataaaattg tgagtcaatc aagatgagtc
18661   ccaagacaat agcctgttta gcccttataa gttcagggat gaaaggttag aaagaaacag
18721   gatggaagga ggactggaga aaaaaacaaa agaggaagga aggaggagga agcaaacagg
```

-continued

| | |
|---|---|
| 18781 | aaaaaaaaag aatgtgcata gcttgtcact cctcagtcat ttcctgggag cccatttcta |
| 18841 | gcaaagtgac agctgcaact ccctggccac ctgagcatct tagctgatct gtctctgaaa |
| 18901 | caccccctgg agaacagatg aatcaggctt catcttcgct taactaagtc ttccctgaga |
| 18961 | cgactccatt taaatgaaca agagcaggat ttcctgggca cactgagagc accttccaga |
| 19021 | ggcccctcca gagccctaaa gcctgtattt cttccagtcg gcctgtttct ttcctggtga |
| 19081 | tgtcattaaa cgcccttga gagtcccaca gtgagcagtt ctgcggtaaa cccgctgca |
| 19141 | attaaagtct gagtcctttc ctgtctcaaa gggcatattc atatagaaga aggaaaagg |
| 19201 | aaggactggc tgtttgcatt tggttccagg cctgttgagt agaggtcgtg ctcactccac |
| 19261 | cgaaggtaca gggtagcctt cagcagaacc tggggatttg gttttaagca agtctttctt |
| 19321 | aggtgtgggc tttcagaaca cttccttcct tgcaatatta tttgaaattc tcagtgtttt |
| 19381 | agccgtcccc agaatattgg ttcgttaaag ctgtgtattt cagatctcca gacagtggtc |
| 19441 | actgtttgta tattttcaat ttcaaaccag aaaacaaaag ttcttattga ttacttttt |
| 19501 | tatttaaaaa ataaaaagta agtatcttcg taagaggagc tttgttttaa ttttaaagtt |
| 19561 | taaaatttga ttgtgaagac agagaaaaac ttgatgattg tagatatatt cccctcttg |
| 19621 | gctattcaat cagagaacta gaaaatcatg agagatttaa tgaccactgc ctgatacaca |
| 19681 | tatgtgtttt acagatgagg aaactgagac ccagagagat gatgaaattg gctgaggatg |
| 19741 | gcccagctgg tcagtgaaag actcagagcc agagctggtg cagggctctt tctattcctt |
| 19801 | cctgttccct ttcaggaaca ctcaccatcg gctttcctgt gaataatgtt gagataaaat |
| 19861 | ccttggtgca ttatgttttc tagtcacaac attgactagg ctgccagagt cctctgttct |
| 19921 | cccagttggt tggctgtagg tgttggcagc cgccaggagc attctacaga acagaggagg |
| 19981 | agtgagactc tccttgctca ggaaaggcag acctatgact tagcaaataa ctcctaagag |
| 20041 | gagagtgttt cacccaccat tcctcttcct tggctgtgga ggcaacttag tggagagggg |
| 20101 | ccagatgacc tgtgaggaac agtgaagccc tgcctaacac aatgtatggt tgtcttgtta |
| 20161 | cagagtcatc agctacgagt gctgtcctgg atatgaaaag gtccctgggg agaagggctg |
| 20221 | tccagcaggt gaatgaatcc tccgggcctt gcctgttggt gtgggtggaa gggaatggtg |
| 20281 | ggagagagga gtacccacat aaaaggcagc agagtgtgaa tgggggcagt ggcacaagga |
| 20341 | catggcattc tccccacgtg cccactggcc ccaggctcta tgcgagggc tgaggaatgg |
| 20401 | aagctggaaa cagcgcattt cctgagctgc tcctcctggc ctccttacca cactggtgga |
| 20461 | gtagactcca actgtggcct gtccatgccc ttcccagcag gcacaggctc aggctcaggc |
| 20521 | tcttggcctc tgcctctggc tgggagtgat tctaaacaca tccagcaggg tcagcctgat |
| 20581 | agcccatcag tttccgatca gctctgctag agagccgatg ggatgtggga ggaggggtc |
| 20641 | actggtgggc tggcaacccc aagccatccc catctccctc tgtgtctaaa cttggcccttt |
| 20701 | tggagttcgg tagggagaag agccataggc caggtgggct cacccagagt cagcagagag |
| 20761 | tcccacaaat ggttgcactg ggcgaaagac agcatggcac ctgtgaattt tattagagct |
| 20821 | tttcttttag tgctacacac aagtgactgt acaggggagt tagtatttg ttttaatttt |
| 20881 | gaaatagagt catctttgg tatctgcggg ggattgattc taggacccat tctaggatgc |
| 20941 | catatcctca gatgttcaag tccctgatat aaagtggtat agtatttgca tgtaatctat |
| 21001 | gcatattctt ccatgtactt taaatcatct caagattact tataatacca aatataatgt |
| 21061 | aaatcctatg taagtagttg ttataccctc ttttaaattt ttgtattatc ttttattgta |
| 21121 | tttcaaaaaa tattttggt ccatgtttag ttgaatctgt gggtgaagaa cccacagata |
| 21181 | cgaagggcca actgtattgg ctatttttt agttaagaat gtgagactga ggccaggcgc |

```
21241   agtggctcat gcctttgatt ccagcacttt gggaggccaa gagggacga tcacctgagc
21301   caagaattcg agaccagcag cccgtgcaac atagtgagac cttgtctctt aaagattgtg
21361   agactgggct gggcacggtg gctcacgcct gtaatcctag cactttggga ggccaaggca
21421   ggtggatcaa ctgaggtcag gagtttgaga tcagcctggc taacatagtg aaactctgtc
21481   tctactaaaa atacaaaaaa attagctggg tgtggtggtg ggcgcctata atcccagcta
21541   ctcaggaggc tgaggcagga gaatcgcttg tatccaggag gcggaggttg cagtgagctg
21601   agatagggcc gttgcactcc agcctgggca agaagagcaa aactccatct caaaaataaa
21661   taaataaata aataaataaa tcatgagact gagacataac aggaaggagg gcaatttggt
21721   tggttccaag gttcctagag tatgtgatgg gagaggttgg tgcgggtggg gccatggagg
21781   tactgactca agtggaggga caggtgggga aatgggatgg gaaaagaaga ttgaccttag
21841   aagggagct caacctctga accctaattt cagaccccttc aaaatgaata ttaagctcat
21901   tttggtctaa gaaacaaaaa acaaatgaac atgaaactca ttttggtctt ataaggtctg
21961   agaaacccct tctaaacttc aagctgcttt aagaaataac attttattac ctgcaaatac
22021   acacagtact ttggagattt ataatagtct cttattctaa tagaagccat tagggaacca
22081   gtttcaataa acaggtaaat ctgtaagact agtttgtaat taggatatct gtttccagtg
22141   tccattcctg cctctgttat ctaaatgtct gggaacaaga gctgtgctct gctgtgttta
22201   aaatgattaa aaatcaccaa ttagttgagt tcacgtagac aggcatttga cttattgagt
22261   tgttttaaga agactataac aagccttaag ccccccagaa acagcctgtc tttgggcttt
22321   cccacatgcc tcctcgtcct ctccacctgt agatgtaccg tgctctctgt cagagaaggg
22381   agggtgtggt tgggctggac ccccagaggc catccctcct tctgtcttct gctcctgcag
22441   ccctaccact ctcaaaccct tacgagaccc tgggagtcgt tggatccacc accactcagc
22501   tgtacacgga ccgcacggag aagctgaggc ctgagatgga ggggcccggc agcttcacca
22561   tcttcgcccc tagcaacgag gcctgggcct ccttgccagc tgtgagatga cctccgtctg
22621   cccggggac tcttatgggg aactgcctta cttccccgag gggtgggcat gatgaatggg
22681   agtctgcagt catttcctac tgtttcagga agctttctcc ttaaccccctt agaaaaggct
22741   gtggaacttg agctaaaata tgtcttacca ggttgcgtct aatgccccccc gttccctact
22801   gggcagaaag acttgggtgc ttcctgagga gggatccttg gcagaagaga ggcctgggct
22861   cacgagggct gagaacatgt ttcccagagt tgcaaggacc catctcttaa acacagagtc
22921   tgcagcccct aactgacacc ctgtccttcc tcctaggaag tgctggactc cctggtcagc
22981   aatgtcaaca ttgagctgct caatgccctc gctaccata tggtgggcag gcgagtcctg
23041   actgatgagc tgaaacacgg catgacccctc acctctatgt accagaattc caacatccag
23101   atccaccact atcctaatgg ggtaggggat ccccagccat actgcatggc ccttggtgca
23161   taatgaaccc atttctgttc catgtgtggg ctggtttctg gggtttaagc tgtagacaac
23221   ccaccctctt tgtgcctgct tctccttggg ccctctattc cacagcttgt ggaacccaca
23281   ttttgctact gtgtttgaaa acactgttt ctcctcccgg ggctttggga ctatgcctct
23341   gttgtgttga ctgctcatcc ttgctgcttc tctgggcaga ttgtaactgt gaactgtgcc
23401   cggctgctga aagccgacca ccatgcaacc aacggggtgg tgcacctcat cgataaggtc
23461   atctccacca tcaccaacaa catccagcag atcattgaga tcgaggacac ctttgagacc
23521   cttcgggtaa gggactgccc tgggtgagg cccaggcttg ggacacattg cctcccaaga
23581   ggggcctagc aggaactctt ctgcaggaga ggtagaggat ggctcctgta ggggaacata
```

-continued

```
23641  gagcaggttc ccctgaatgc ccttgaacat ggagaattca ttgaccagac attcagcttg
23701  acctaacctg tgaaattctc catcttcttt ataaagtgtt cccttccttg cctccctgg
23761  aaaggtcagt ggtgtgtggc tgcagcagca cagtgtcctc tgagccctgg acctgcactg
23821  tggcttccag aggtggcagt tcccacatgg ggtactagaa taaatggcct atcaggctgt
23881  gtgtgctttg ggatcacatg tccccaccct aggaccctgg ttccaaccat acgcatgttc
23941  tcttggagcc cagaacagca gagaagccac cagtgtggac acagaagtca agggtctgat
24001  ttccagcctg gcttctgact gctctggggc cgcaggaata cggttccttc ccccatgccc
24061  agcaggcatt tgtcttacaa ctggagggga aggcatgttc ctcttggcaa ggactgctca
24121  ggaggaagtg gaggcaggct gccctgtcag ggttttttgcc ttgattcaag agaacttcc
24181  taaccacaaa ggatacaagt gggagtgagg cggaccctcc ctagagatct ccaacacaga
24241  gagacaaaca cgctggggct ggctggcact gacaggcctc gcaggtgtgg atggctgtta
24301  gctgggagct tcgctgtcta agctcctctc ccatgctttt cttctgggtt gctcgaagga
24361  cggggtctg caagaaaatg atgttcccac atagttggca gcacgtgaac agcaattgat
24421  ccctttgcat cacctcctct tactgtttag atttggtaaa tatttcttcc ttccctcttc
24481  tgaccctcca ttttgccgat ctttccttct tataacacat acttactagg tacctgctac
24541  ttcccgggtg ggcctatgtg ccaggagtat agaggtgaac aaggaaggca aagttctatt
24601  ctcagtagag ctaatactct atctggagag acaacaaa caaatcaaca aggtagccag
24661  gggctgtgat aatttatgtc aagtgggcag gtaaatcggg agtgacagta gtgcagggag
24721  gattggaaag tcaggagtt ctctctggag gaggtggctt ttgatctgca gcctaaagga
24781  tgagaatggg tccattatac aaaatgctgg ggcaagagca cacccagtag aggggagagt
24841  aatagcaaag gctcagggca ggaagggcaa gggagaggcc agtgggtgag gtcacatgtg
24901  aagggcatac aatgggcaaa gacaaggcca gagtggccag gcccaatcct ccaggacttg
24961  cagacctggg aaagagtgca tctccatcct gggagcagca ggaaaccact caggccttta
25021  gaagatcctt ctggcagctg tgtagagaat gggtggtgtg atccttccat gcatgggctc
25081  atgtacgtga ttaccagtaa ctgtcgagtg acagtgtgag gagggctgca agccatgagt
25141  gtaggcacag cagacagact cacctttgtc tggcggtgag atgggtggg aagtgtgcca
25201  agttgacctc ccaaagaaat gatattttag tggaagaatg aatagaatca gagaagcaaa
25261  gtaagaggga agagcagaga ggacagcagg acaaggact tgggggcagg aagaggaaag
25321  gcaggttaag gacatgaaag atggccaggc tggctggagc tcaggcccag caaggccccc
25381  tgggggccat ggtcatgggt gagcttgggt ttggcttctg ttttcgtctt gggcttctgt
25441  gaaagcctcg agcccttgcg gggaaccagt gaagctgtgt gtgcatcttc tgtggggagt
25501  gccagagtct tcagggagca ctccatcttc tctcctcccc acaggctgct gtggctgcat
25561  cagggctcaa cacgatgctt gaaggtaacg gccagtacac gcttttggcc ccgaccaatg
25621  aggccttcga aagatccct agtgagactt tgaaccgtat cctgggcgac ccagaagccc
25681  tgagaggtga gcatccttg gctcctgctg ctgcctcatt tgtgcagcta gattgagccc
25741  aagacctgct ctggtccaag atgaacatac cacctgccat gaggtgaccc tcaggatatc
25801  cactgcagcc atgggctggg gtcatcctgt cctgttgctt cagctaaccg tgtctctagc
25861  agccacacta ctctgagggc tgactacaga atccagcagc ttttgtctgg gagagctgga
25921  ctgaagagag gcatagctgg agacccatag ctggccctgg ccagaaacag ggagagtgaa
25981  aggctggaat agccaaggcc agagcaaggc taataggtag agcaacagct tacaggtgtg
26041  ggggtggcag atactggcac ccttgaaatg gattcctcat gcccacgctt cactattctt
```

-continued

```
26101  ctctgtggct aggggattta tggataaacc aaaattacag ttaaaaacca gccataggcc
26161  aggcacagtg actcacgcct ttaatatcag cactttggga ggacaaggtg ggcggatcac
26221  ctgagatctg gaatttgaga ccagcctggc caacatggcg aaaccccatc tctactaaaa
26281  atacaaaaat tagctgggca tggtggtggg cacctgtaat cccagttact caggggctga
26341  ggcaggagaa ccacttgaac ccaggaggtg gaggttgcag tgagccaagc ttgcaccact
26401  gcactccagc ctgggtgaca cagcgacact ccgtctcaag aaaaaaaaaa aaaaaaacag
26461  ttatagtagt caacttttga ctctccattt cagatttcgt catgccctcc tcaatgagct
26521  gctaagttag gcagtgcatt gattattgct gcaggagagg gaaggaagga gctaacgtgt
26581  tttcacatgt tttccttttg gagatgagaa aggaggactc tgccttcccc ctaccctgcc
26641  cctttctact ccaggacctc tgaaaggcca tgagcacaaa gctgctgcct gagtcccctg
26701  aaatgcaggg tacgcccag gtctctgatg taccccacca cacttttcct ctcaaacata
26761  ttccaggatc acttgatttc ttttgaatct atttaaaccc accgtgtcaa tgtgctatat
26821  aaaatgtcta atgcatttca gacaccctat acatctatac atttaaagtg ttctccttct
26881  atctgtgcag ggatgggaaa gggcatattt ctgaaagcac agatgggaag acgggatttg
26941  ttccgtgtcc aggtgattat ggtacctcta tgcgcctggc cggcactggg gacagaggcc
27001  atgaaaatga atacagcaca gcctttgcct ccaagaaact taagacctag tagaaatggc
27061  aggctttaaa acaggttgtt gggatctgat ttggtgagtg caatgacaga gatactcaca
27121  gcacaaaatg gggaatgagg gcgggcattg ggacacacat agccttaagg ggcccaaagg
27181  cttttagaac tgtattccct attaaaacat gatttgcaca gagcacattc tttgctttgg
27241  agacctcaga actccttact ataggccggg catggttata atcccagcac tttgggaagc
27301  caaggcgggc agatcacttg aggctgagag ttcaagacca gcctggccaa catggtaaaa
27361  ccccgtctct actaaaaata caaaaattag ctgggtgtgg tggtggccac ctgtaatccc
27421  agctactcag gaggctgagg taggagaatc acttgaacct gggaggcaga agttgcaata
27481  agcccagatc atgccactgc actccagcct gggcaacaaa gctagactct ctcaaaagaa
27541  aaaaacaaaa caaaacaaaa caaaacaaaa aaaactcctt attataaact gtaagaaaaa
27601  aaaggcccct acttcgtccc ttttgcaaat ctgccttttc ctactcacta accagctggt
27661  tcagagcaag gacactctgt ttggtgccat cgctgcagac tggaaggaag aggtccttgc
27721  cccacaccca acagtctcct gctgttaccg gcaggttggc aggcaggcag gcgagaagca
27781  gccagggctg gtggtgtgtc cagtttgaag actagtttcc agccctggcc ctgctcaccc
27841  tccaagtggc cctggcaggt tcctctacca catcgtggac ttcaccttcc ttctctaaga
27901  agctcaatcc caaggcctc attcccatag gccttctcac ccttttctt tccctctggc
27961  tgaatgtggc cagcacgggc ttccaaggcc atcaactcgt ctgcagcagc cccatgcctt
28021  gcagggcctc agagcttcct cctgcctatg acagtgtggt tttggttccc acacttggga
28081  tcagattgaa actcgcctcc gtggtgagaa tatgggacat agagcctcgg tgaccttggt
28141  gagcagcagt ccaggccacc tgctcagcct ggggttgggg ggggctcctc ctccttgact
28201  ggtccttgca tttgcctcca tccagcctgt ctgggctctc cgaggcaatg agaccagca
28261  ggagtcacga tgggtcagga gcccccttg ggcctcagcc ctgccctgcc ccctaaagta
28321  gcacttggat aagcaaataa attattatac ttactattta tgggtgtggt gaatgggatg
28381  gcaaaggcca agtcttactg atcaccaaac cttaagatat atcctggcag ctagtagacc
28441  cttgggctaa atgaacagaa aactggacaa ataagtgta cacaaataac tcaaagctgt
```

-continued

```
28501  catttgtaca cttttcgtct tttcctacta cagtttacat ttttataaag gtgagtagat
28561  ttctaaaatc ccgtggtagg ctctcttgag ttttttcttgt atccctgaag ttcagctaca
28621  aataagctaa tcactaacat ttgttgagca tttactctgt tgtcaggccc cgtgccgagt
28681  gctttaggtt cagaatttca tgtcatcccc acagcagccc taggagatga atgcaattct
28741  tatgtccact tgactgataa ggaagttgag gttcaaagag gctaaatgac tctcccaggg
28801  tcccacagct ggaaagtggc cacagggccc cagctggttt tctagggcag caggcagaag
28861  gcgaggagga tctgggccct gtggtgcccc agcctcatct gagggtcctc atctgagaga
28921  acaggatcct cacagcatgg gcaggctgca agtggtccct gaggttatcg tggagtggac
28981  cctgacttga cctgagtctg tttggacccc agacctgctg aacaaccaca tcttgaagtc
29041  agctatgtgt gctgaagcca tcgttgcggg gctgtctgta gagaccctgg agggcacgac
29101  actggaggtg ggctgcagcg gggacatgct cactatcaac gggaaggcga tcatctccaa
29161  taaagacatc ctagccacca acggggtgat ccactacatt gatgagctac tcatcccaga
29221  ctcaggtagg ccaggcctcc gggggccttg ccctgcctg gcccaccatc tcttctgcca
29281  tcctttgtgg cgggggaggg gaaattcaga gatctttggg cgacttccct gcctggaccc
29341  agctcacagc ttctcggcca ctgcaaatgt gtgggttgtg accagactga tgtgtcttga
29401  gcttcaggct tgcaagtgca gtggagaggc agtggggagc tattgaaggg gtctggggac
29461  agactcaatc acagaggcct ttcagaagat ctgcctgctg tgcatgggca aagagggcca
29521  cttgctgacc tcagagcatg tgctttctca gtagtgccca agctgtccca tggtcactga
29581  cccagttaga atgactgaat ggactttggc ttgtgtctca ttaggaatcc tagccccatt
29641  ctagtcttcc agtgagatct gtccatgagt gaaggaatct cacaggaaaa acaaaatgc
29701  ttctatgggt gtggttgctg gccttatcta caccacagaa gccatcacac agactgtctt
29761  tcttcccatt gttagaatgt gccctgacca agcagcccac agggcctggg acagaggctg
29821  atctctgcct aactgagctc acctctcctc cctctcctcc tgactggtta gatttctag
29881  gtgactgttc ccctgatgac acaagcccgc tgggccccag cagtgtttag aggggttgtt
29941  gactcacgag atgacattcc tgctgatgtg tgtcatgccc tggggtggat gaatgataaa
30001  tgaaaacagc gcttttaact tttgaaccca ctttctcctt ccttgtagcc aagacactat
30061  ttgaattggc tgcagagtct gatgtgtcca cagccattga cctttcaga caagccggcc
30121  tcggcaatca tctctctgga agtgagcggt tgaccctcct ggctcccctg aattctgtat
30181  tcaaaggtaa catggggaag gcatccctgt tagattgtcc ctggaggcag cttccccacc
30241  cctgtcacct ccacaacact ctccgattta cagcaccca tgggacatta gaacttccac
30301  tcagctcaac caaaagcaga tgtgacttca gcagaaactt cagaggctct gttgtttcat
30361  taggcagtgc agagaatgcc tttggggagc cgttcctcag aactcaagac ttgacatctg
30421  ggaggcagcc gttcctcaga actcaagact tgacatctgg gagagcagag cattcccttg
30481  cctttctatt tgcagggtca cttgccaatg tatagtcaag aggtcagagt gagggtacag
30541  ctgagctgca gccccaggaa ggcagagaag ggggccaagt tgtgtgcgtg cctgcccttc
30601  cctcttaggg caaaactcca aacacccttg attatctgga tcttctttaa ttctccatag
30661  aagataccag atgttaagga atattggcag cttcacttgg tttctcaatc cctgtttcca
30721  aactcaagga gggatgggct ttttcactgt atttatctct catcactctc ttcattgcag
30781  gagcacatct ctctggacct aaccatcacc ctttcttgta gatggaaccc ctccaattga
30841  tgcccataca aggaatttgc ttcggaacca cataattaaa gaccagctgg cctctaagta
30901  tctgtaccat ggacagaccc tggaaactct gggcggcaaa aaactgagag ttttttgttta
```

-continued

```
30961   tcgtaatgta agttctgggt cctaaatcat gctcctggga agctccttac tgtgggactt
31021   gtattagtgt aaaaaaaaat gtcctcaata agcaggagtt tgcatgagaa ctggttgctg
31081   acaaggaagg aaataatttc tggaaaatat agataacaaa atgagatcct gcagaaggat
31141   tggaatctct ttttctggag gcctttgaga ataaaccaca caattatcca acctgtattg
31201   tgaaggaata agtccttctt gaattcagga attaacacct gggaggaggg atggagttca
31261   gactctttct gagcttatga aagagaagc cccctaaaact aaaatacagc cctccttggt
31321   ccaaaaggtg ccttctctct tctgctgtat cttctttgtt ttcaaaccca acagttaccc
31381   tggaaatcaa aaaggaagta caactcaaca tagctcttgc ctgggaccaa ccagcaccat
31441   ttggctaaag atggttatca tctgttaaac aaagaaataa ataaatgggt tcaacgtatt
31501   tatttcaaca ttgtcaatgg acctcatgtg taactgatat tctcattatg ggacctctgt
31561   gtgactttat tggggcctct ctaaccgttc tttccttaag gaagaccatt tattgtttta
31621   tttcctggag aaaatacatc attttatccc agccttaata acccatccca gtgtatactc
31681   cttcatcttc atggataatg accctgctac atgctctgaa caaatcagga ggcccctcgt
31741   ggaagtataa ccagtccttt cttttctctgt ccctcttctg tgcagagcct ctgcattgag
31801   aacagctgca tcgcggccca cgacaagagg gggaggtacg ggaccctgtt cacgatggac
31861   cgggtgctga cccccccaat ggggactgtc atggatgtcc tgaagggaga caatcgcttt
31921   aggtaattag ttccatcccc gggtggagct tctgcccagt ggtcatgctg gagtgggatg
31981   tggggcccca gctatttgtc aagctttctt ctaccttggg gattcaatta cactagcag
32041   tgcactgctg cgaccttcca gactgggat ggggaaaagg caagggtcgc cttgaaagct
32101   tacattggga agaagggtta cttctaagag tgtaatcttc acatgcatgg gaagcaggga
32161   gggggggacta cattttttatg actgaagtgc aaggaaaaca tcaccctctc attgtaaagc
32221   tccaagtgag ccaagagcac atagtttaca gtgcacgatg agcctctcac tctctgcgca
32281   gtatctgttt attgcaactg aagcacccctt gtgagtttgt tttcttgccc ggctatctcc
32341   atttctgact tgctcattca ccttggggtg ctgtcatatt gaatgtttcc ctgtcactga
32401   cttcagccac ctgcacaagg gcttggagac cacaccccctc tgccctccca gaatcatatc
32461   cctggaggct cagctagtct ctgggtcagc catacctctg cccttctttt tccctccttt
32521   ctcctgtggc ctctgacgtc tggccattta acagagctta gcattttgc tgggtggaga
32581   gagctggagc ctggaatcac tccctctttg tgcatacgga gggcatgaaa accaaggtgt
32641   gtgcattcca gtggcctgga ctctactatc ctcagtggtg aggtattaa ggaaaatacc
32701   tctcagcgtg gtgaggtatt taaggaaaat acctgttgac aggtgacatt ttctgtgtgt
32761   gtatctacag catgctggta gctgccatcc agtctgcagg actgacggag accctcaacc
32821   gggaaggagt ctacacagtc tttgctccca caaatgaagc cttccgagcc ctgccaccaa
32881   gagaacggag cagactcttg ggtaaagacc aacttaagta cacgtctcca tttttctaaa
32941   gtagtgatcc ctcagggccc cagcagcaaa cagttggcac atcaaggatt gacttgaagg
33001   gattttatga caagactatt agtgaaagag tgggcgggac taaaggaact agcaaaggat
33061   gaggccaacc agggactagc aaccctggga agcctttact accccctaggc ctgggggaat
33121   gggaggatga gagcaggaac cagggaggtc atgagccttg acaagggca cagaacagca
33181   gccagagcca tgtgcagcca gccactgtca gaaccatgca aggggggacca ctcagcgccc
33241   cagcctccct ctcagacagt tgccatctgg gtctcttgtt ggctgatgcg agagcaggag
33301   ggagcccact gatgcagttc atagagctca gcctcctggg caggaaaccg ggcagagagg
```

-continued

```
33361   agtagaaaag aattaagggt ggctgcgacc agcccagtca ctgaggcacg tttcccactg
33421   gagacctatg agcacagtga taataaagcc agttacctgc actgactatc cctccagaca
33481   aaagctttcc caagaagtta gtcatggctc tgagagatct agttgaggat gtttggcagg
33541   ggatctagtg gttacggggtg gctaagaaaa atgaggaagg taagagtatc ttgcagcctg
33601   tgttgggagg attaaatagg atgccacaca cagggccagg cagacagcct ggtcagtaat
33661   agccatgacg atgggggcgg ggggagcagg aatgggagtt gcagtgttta gctcagatgc
33721   atgcctgtga gagatgcttc cactctcaca gaaagatgag accaaggaaa aggaggagga
33781   agaggaagga ccttgacaaa ccttgggggcc cacattgtct acacctccct tcctgctcta
33841   gagcagaata gaaagttcag gttgcaggca gctctaagtt gaattcgtgt cctgtttaat
33901   tttctttatt gctaaatgaa tgcctgtgtc tgtgatgctg acgtatgttc ctaaggagag
33961   gggagaagtt cattctgaac ataaacttt catcctctct ctgtccagca agaatggaat
34021   attccccaag tggcctgagc cagcttggct ttcttttgt tttcaattat gtgggagttg
34081   aggaggggga tgggaaaagc ttcccaaaca cacctcccc caggcctgag gcacccctgg
34141   gggacagaga gtgttagagg ttggtacagg tgttagagat attgaaagga catcccatgc
34201   accccagggg ctggtgtggc tctgtacttc caggcaatat tttgtggaag gggaaccttg
34261   tcagctccag gttgtggatg tttgaaaatc agttggtacc cagtggctcc atcctctggc
34321   aggcatgtgg atttgtcaat aaccaagtga actctccaaa ataagttaaa acttcctccc
34381   ttctcagttt caagatgctg gaaatagctg ttcataagcc ctggggaaat ttagcccttt
34441   ggctggtaat gggagtatcc gagatgagag ggcagctgga aactttcgga atgacctccc
34501   acacttaatt tgggaaatgc ctctgcacct ttatgggcaa ccagatgcct gccccagttg
34561   ctggagacac tgatgtgggc tgaaaggaat gctgagacgt gacgaggaga gatgctgcgg
34621   agggaatatc cccctcagcc ctgacctcat cggctccatg gctcctccac agtacagctg
34681   tctactcttt taagttctcc cttcaggaaa tagccatctc aaacagaatg tgcatttgag
34741   ggcagaatgt gtaaatattg cactactgtg ttataaccgt caggagccat gctgatgatg
34801   aaacgtccca gatgccggtg ctggaaaggt ccctggcttt ccaagcaaat atttatctca
34861   tggaaacatg agtcatactc acagaggagt atggattaac tccttctcag cagccaggga
34921   gcccagcatc ccagacagca tatttaaccc agaggccaac tgactgctgg ggcagatttg
34981   tggtcatgaa catgtgcttt gtgtcctctg accattagac agattgtggg tcacaacgtt
35041   gagtatacag tgggagctta ataagtgctt attccctggg cagggagttc ttcatttcag
35101   gggtgaccac ttacatcttc tcctctgggc cctccttgac caggctaatt accattcttg
35161   ggattaactc tatctccttt tcccgcaacc tgcaggagat gccaaggaac ttgccaacat
35221   cctgaaatac cacattggtg atgaaatcct ggttagcgga ggcatcgggg ccctggtgcg
35281   gctaaagtct ctccaaggtg acaagctgga agtcagcttg gtaagtgtcc tgcaaatcaa
35341   aggctggcta aatttcccca gggcagggct ccaggacata tctcacccc aggatggaat
35401   tatacacaca caaccttcaa gttgcagccc gaatctctga gtgtaattcg tccaaagaaa
35461   aagagaaaag agaagagggt cttcaggaa atcaagtgag atcatagtta gacatgagta
35521   agaacttcca gatttacaag ggaatagagc atctgatttg gcatctgaga gaggctatta
35581   gatcttcctt ctcttaagga ggttgtaggc aactagttat gtgactgaag agatcagtct
35641   gtactcacac catcccaccc cccaaaccca gggcttcact gagttgtacc atgaaccaga
35701   ccatcccaag aggctttttg agttctgaca cttgctctgt gagccttccc ttgctctgca
35761   cattgatgat ataactttgt aactgcacta agagtgttcc taaagcagat agccagccga
```

-continued

```
35821   gctccagaaa tctccctggc tgcacctgca gaggccactg acccctctgt ggagggaccg
35881   ctcttcagtg tgtggctggc ttctactctc tgctcctctc tcttggtctt cagccatcca
35941   ttgctcacca gtttctcacg aggagcatag gaagatatgc atgtagggag gtaggcacgg
36001   ggatgacttg tttgacttta gcaggtcatt caagaatctc ctcgcacctg gtttcagatg
36061   ctggggtcct gtctgtcaca ggcttctgtg cctcctaccc ccttgagttt gtcacatggc
36121   ccttcaggaa ggcctgagat agatttgccc tgggtgggcc tcctatgaga aaatcttaag
36181   tgaggcaccc aggcaaaatg gaaagagcct tttgcccaga gcaggaagcc tgtcttccat
36241   ttccagctgt tccacctact tagcttaaaa gaggcacttc gcctgtcttc agtctcagtc
36301   tcagtctcct cttctgtgga atgggacaat aatatctact ctccttatca tacactgctg
36361   tgaggactga gtggatcaca caaaaaagca ttatgtaaat tgcaaagtgc taaatccaca
36421   caggagattt gaattaatcc accacactga aggtctgtca agggcaggga ctgtttcatt
36481   caccagagta tccccagtct aacacaggac ttggcatatg aaaagtgttc agtaggccgg
36541   gtgcagtggc tcatgcctgt aatcccagca ctttgggagg ccaaagtggg cggatcatct
36601   gaggtcagga gttcaagtcc agcctggcca acgtggtgaa accacatctc tactaaaaat
36661   acaaaattag ctgggcgtgg tggcacatgc ctgtaatcac agctactctg gaggctgagg
36721   caggagaatc acttgaaccc aggaggcgga ggttgcagtg agtcgagatc atgccactgc
36781   actccagcct gggcgacaag attgaaactc catctcaaaa acaaagaaca aggaaaaaaa
36841   cgaaaactgt tcagtaaaca cttgctgaat gaataaaata aatatataaa tgtataaata
36901   aatgctctac tttcaaccac tactctgttt ttcttttaga aaaacaatgt ggtgagtgtc
36961   aacaaggagc ctgttgccga gcctgacatc atggccacaa atggcgtggt ccatgtcatc
37021   accaatgttc tgcagcctcc aggtaagtgt cgcatcccca ctgactctgc agccagtcct
37081   tttcttcatg tggcagttgg tggagagaag aaaaactgtt ctaaacaatg atgagaataa
37141   catgtaattg tgatagttaa actgtgccta tgtgactgat tgcagagtga attgggagct
37201   gttggttttg aatgcaccac actaaggaat gtgaggacac attgctcttt gcggagttgc
37261   ccagctatat tagctcccct cggacacagc ccagttttct gtattcgcgt ggatgctgtc
37321   cgcgcgattc ccagcactcc tcttacagca tctcacctca gtgtatgttc cttgcctcca
37381   gtgcagttga acctcagtcc tgcctctcct catgtgtgca ttcacctttc ttggtgctct
37441   ctccccatgg gccaagttct accatgagtt atgaaacatt atggagaaaa catgtctttg
37501   gaaatgtgag ccagaaagcc caccagtgcc cctcagtcac ggttgttatg aatgacatgc
37561   taatggtttc actctggtca aacctgcctt ttctttcctc ttcagccaac agacctcagg
37621   aaagagggga tgaacttgca gactctgcgc ttgagatctt caaacaagca tcagcgtttt
37681   ccagggtaag atgcctgcta ggtttgcgcc tagcctgagc agcctcaggt cctctgtttg
37741   ggccatagag gagcctctcc agcccctgtc ttccttggct gctccccagg gctctcttaa
37801   aacttctccc cactcccact gaggcatcct cagcccagc ctgtgtcaaa ttcagagtaa
37861   agaaccaagg caactccctg gctttcatgg gccaaagcgc aggctttcac accgaggcct
37921   ctgagcctca gatcatgggg aagtcactgc tggagagaac agacatagct ctggaagcca
37981   tctgcccaag agggcagccc atcccaagtt catcttacag tggccaggcc tgcctgagc
38041   cggggcctct gggtcactct tctgctgtcc atggcattgc ccatcctggg tgaggctggg
38101   gctctcctgg gcactgtatg tattctggat acagggatac tgggctcgct atgtgtgtgg
38161   agccatccct tccttgcccc agccccacct ccctctcaaa ccctctctgg ctctttctga
```

-continued

```
38221  gcttcctttc ctgctcccca gcttgcccag tgctcagtgc cccacttggc tcttttgcta
38281  cttcgggtca ggtggagcct cttgggaatg tgaagtgcct tacagaaaga ttgcacttca
38341  agaggagagg ctgcaggag ccatcctaaa cccagaggcc tggagcttac tgtgtcactt
38401  tacttttgta cacagggtc tccttagtgc cctcgagaag gattcttggc cctgagcttc
38461  tactcctgag gccacctctg tgcagcccca gctccctcaa ctctaggctg tagtctcagt
38521  gggaaagcct ggcttggggg tctcctagga atgtccacct gaaggcacac ttgatagggg
38581  cttgcacaac ttatgtctgc caaggccacc tgaggaactc cctggtgcct ataagttcca
38641  ccttcccctt cctcttcctc gccccagcat ttttctgag taggggtgg aatgggcaaa
38701  gccattgtca taagcagttg caggtataac tttcactaga aaacctgaca ccttgtgttt
38761  tctttcaggc ttcccagagg tctgtgcgac taggtgagtc tggtctgggt ttgaagtcat
38821  tgcagacctg tttaggcctt accccaagc aagcccaagc ctgccatctg ctgtatatag
38881  ataagaacat catggtgcag taaagaagc ctggcctttg gagtcagaac agcagggtga
38941  cttggggtca gacccagagc accccatttc cttctctgta agatgaggat aataagagta
39001  acaacctttt agggttaagg tgagttttca gcttaggaag tctgggaata ttgcaaaggg
39061  cttggcagga acccatggtg aggatctagt tccaagttga taggtacaga aaaccagaac
39121  atcgggcctt gagtaaagag tgaagtttca caaccacaa agcacctgct atgtgcagga
39181  gagcatggca gaaggaggct gcttggccct ggtccttgag attctgacag tgtcctagac
39241  agacatgggg agatctgcac ctatttgacg ttaccaactt ctcttttca gcccctgtct
39301  atcaaaagtt attagagagg atgaagcatt agcttgaagc actacaggag gaatgcacca
39361  cggcagctct ccgccaattt ctctcagatt tccacagaga ctgtttgaat gttttcaaaa
39421  ccaagtatca cactttaatg tacatgggcc gcaccataat gagatgtgag ccttgtgcat
39481  gtgggggagg agggagagag atgtacttt taaatcatgt tcccctaaa catggctgtt
39541  aacccactgc atgcagaaac ttggatgtca ctgcctgaca ttcacttcca gagaggacct
39601  atcccaaatg tggaattgac tgcctatgcc aagtccctgg aaaaggagct tcagtattgt
39661  ggggctcata aaacatgaat caagcaatcc agcctcatgg gaagtcctgg cacagttttt
39721  gtaaagccct tgcacagctg gagaaatggc atcattataa gctatgagtt gaaatgttct
39781  gtcaaatgtg tctcacatct acacgtggct tggaggcttt tatggggccc tgtccaggta
39841  gaaaagaaat ggtatgtaga gcttagattt ccctattgtg acagagccat ggtgtgtttg
39901  taataataaa accaaagaaa catacgtcct gtgtgcatgg tacagtgtgc tgacctgagg
39961  ccgtcatgct cctccacacc tcaattctgc tctggagaag ctcagaaagg agccccgagg
40021  gatggttttg gggagattcc agcagccagc cctcagacag ccagacagct catgggggtt
40081  tgagcctgtc tttgccaaac aggttttat ttcaccctcc tccggtcctg gggtttcaag
40141  ttttcagtgt tgccttcacc ccgcacttta ttcctcttat tacttggaag taccttccct
40201  ccagcatggt gatccctgc ctgtgtgctg gacttttgag tcctcagcac caacctgtga
40261  agtggttgcc agcataatcc cattatgcag atgaggagac caaggcccag ggaagggaga
40321  accaccagca gcacgtaaaa tagctgagct gggactggaa ctcacacctc ctgactctca
40381  gtgaccacca ctgacaacag cataagtcca ggttttccag gcccatcccc tctgtgccaa
40441  cccacattca gattccttcc ccggctcccg taatctctgg catctagaat atcctcagga
```

```
40501    ctctgagagg tgatatcatg tggttgtggt gccattgccc cctacctgtg tggcctgggg
40561    ccagtcatgt gacctcccag ggtctcctct tctgtaatag ggagatgacc gtcacatcta
40621    cttcatgggt ccatcgtgag gatgaaatga gatgatctat ataaaatgct tggtacaaca
40681    ttaggtggcc ttatttttat cctgccgtct gggactgctc aggatcaatg cgccagagag
40741    cctttatttg tgtctttccc acaggtgggc tggcccactt tcctagagaa tgggacagac
40801    ctccttccca cccacaccca tctctgccaa ggctgattca ctccagcagg cggagctcat
40861    ttcacttcat ggaaccaatg acccaaagat atatccccag cactactgct ggtcagtcca
40921    ctgctgctgg gaatacagca atggtagtgg cagacagagg ccctctctta aatagcttcc
40981    agtctgagga aagagagata tgacatcaat ccattaaaat cattcatcca ttggttccac
41041    aaatatttgt tgagggctac ctatgtgcac ccccatgtta gaccctgggg aatagacatg
41101    tcattctcat gaggcttctc tactgatggg ggggaagaga attgtcaacc agataatggc
41161    actacagcct gtgtgttctt agtgactctg aggatagcac tgtggttctg tgacagataa
41221    tgaaggattt ggaagcagga atgcccagga gctcccagaa gtgggaagag atgagaggaa
41281    tggaaggaac ttacctgaag gtgaaggcat caggctaggg gaccaaggga gaaggtgtcc
41341    tgagaggtaa ggcttaacct tgggtgtgaa ttcagttccc gtcactctcc catagctctg
41401    tcctgctgtt cccacctccc ctgcagccat gcgggcttgg gcggctagtg agggccttgc
41461    tcatgctggg tatcctatgc tatgcttcac tttgagcacc taaaatacac acactgcact
41521    ttaccaagat gacctcggaa accaaagagg tgatcagcat aagtttaaa gaccccttaaa
41581    tttaaagtaa aaatcactac aggatccatt ataaatgcca aacactaaga tgtgtgtttc
41641    cagttctccc cttcatttgt ccctgccact ccctgccctg actttgcccc acccctagt
41701    aatgtgggct ccactctatg ctccaaactc tccctggaga gaaatcctcc ctgtggttga
41761    ggacaaggcg cagccttccc ctcccaccaa agaaggtcag attcccttt ttggttccta
41821    accatccata ccccttcttt tctcatgaag actcgggcta agcattcatt agggctgcca
41881    tctggaggat ggaccctag agctgagggg ccagcactgt gtgt
```

The following shows TGFBI gene protein product WIG-H3 protein sequence; NCBI Reference number NG_012646.1) (SEQ ID NO: 62).

MALFVRLLALALALALGPAATLAGPAKSPYQLVLQHSRLRGRQHGPN

VCAVQKVIGTNRKYFTNCKQWYQRKICGKSTVISYECCPGYEKVPGE

KGCPAALPLSNLYETLGVVGSTTTQLYTDRTEKLRPEMEGPGSFTIF

APSNEAWASLPAEVLDSLVSNVNIELLNALRYHMVGRRVLTDELKHG

MTLTSMYQNSNIQIHHYPNGIVTVNCARLLKADHHATNGVVHLIDKV

ISTITNNIQQIIEIEDTFETLRAAVAASGLNTMLEGNGQYTLLAPTN

EAFEKIPSETLNRILGDPEALRDLLNNHILKSAMCAEAIVAGLSVET

LEGTTLEVGCSGDMLTINGKAIISNKDILATNGVIHYIDELLIPDSA

KTLFELAAESDVSTAIDLFRQAGLGNHLSGSERLTLLAPLNSVFKDG

TPPIDAHTRNLLRNHIIKDQLASKYLYHGQTLETLGGKKLRVFVYRN

SLCIENSCIAAHDKRGRYGTLFTMDRVLTPPMGTVMDVLKGDNRFSM

LVAAIQSAGLTETLNREGVYTVFAPTNEAFRALPPRERSRLLGDAKE

LANILKYHIGDEILVSGGIGALVRLKSLQGDKLEVSLKNNVVSVNKE

PVAEPDIMATNGVVHVITNVLQPPANRPQERGDELADSALEIFKQAS

AFSRASQRSVRLAPVYQKLLERMKH

All headings and section designations are used for clarity and reference purposes only and are not to be considered limiting in any way. For example, those of skill in the art will appreciate the usefulness of combining various aspects from different headings as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed:

1. A method for detecting corneal dystrophy (CD) comprising:

(A-1) amplifying one or two DNA regions of interest from a biological sample from a subject using a reaction mixture comprising at least a first amplification primer pair to produce one or two amplified DNA regions of interest;

(B-1) hybridizing a first labeled TGFBI G623D mutant detection probe comprising the nucleotide sequence of SEQ ID NO: 36 and a second labeled TGFBI M502V mutant detection probe comprising the nucleotide sequence of SEQ ID NO: 30 to a first TGFBI gene sequence comprising a region encoding amino acid position 623 in the one or two amplified DNA regions of interest and a second TGFBI gene sequence comprising a region encoding amino acid position 502 in the one or two amplified DNA regions of interest, respectively;

and (C) detecting CD if the at least G623D and M502V mutations in the one or two amplified DNA regions of interest are detected.

2. The method according to claim 1, wherein the labeled detection probes are fluorescently labeled.

3. The method according to claim 1, wherein each of the labeled detection probes comprises a different probe and is independently labeled with VIC, FAM, ABY, or JUN.

4. The method according to claim 1, wherein the reaction mixture further comprises:

(a) one or more corresponding labeled detection probes, each of which comprises a normal nucleotide sequence selected from SEQ ID NO: 24 and 33;

(b) at least one corresponding forward primer comprising a nucleotide sequence selected from the group consisting of SEQ ID NO: 7-12 and 41; and (c) at least one corresponding reverse primer comprising a nucleotide sequence selected from the group consisting of SEQ ID NO: 13-18 and 47.

* * * * *